United States Patent
Tavazoie et al.

(10) Patent No.: US 12,162,942 B2
(45) Date of Patent: *Dec. 10, 2024

(54) ANTI-MERTK AGONISTIC ANTIBODIES AND USES THEREOF

(71) Applicants: The Rockefeller University, New York, NY (US); Inspirna, Inc., New York, NY (US)

(72) Inventors: Sohail F. Tavazoie, New York, NY (US); Masoud Tavazoie, New York, NY (US); Nils Henrik Halberg, Bergen (NO)

(73) Assignees: The Rockefeller University, New York, NY (US); Inspirna, Inc., Long Island City, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/062,355

(22) Filed: Dec. 6, 2022

(65) Prior Publication Data

US 2023/0146646 A1 May 11, 2023

Related U.S. Application Data

(62) Division of application No. 16/626,456, filed as application No. PCT/US2018/039445 on Jun. 26, 2018, now Pat. No. 11,613,588.

(60) Provisional application No. 62/525,993, filed on Jun. 28, 2017.

(51) Int. Cl.
| | | |
|---|---|---|
| *C07K 16/28* | (2006.01) | |
| *A61K 39/00* | (2006.01) | |
| *A61K 39/395* | (2006.01) | |
| *A61K 45/06* | (2006.01) | |
| *A61K 47/68* | (2017.01) | |
| *A61P 35/00* | (2006.01) | |
| *C07K 16/40* | (2006.01) | |

(52) U.S. Cl.
CPC .. *C07K 16/2863* (2013.01); *A61K 39/001154* (2018.08); *A61K 39/3955* (2013.01); *A61K 47/68031* (2023.08); *A61K 47/6817* (2017.08); *A61P 35/00* (2018.01); *C07K 16/40* (2013.01); *A61K 45/06* (2013.01)

(58) Field of Classification Search
CPC .......................... C07K 16/40; C07K 2317/33; C07K 2317/75; C07K 2317/92; C07K 16/2863; A61K 39/001154; A61K 39/3955; A61K 47/6803; A61K 47/6817; A61K 45/06; A61K 47/6849; A61K 2039/505; A61P 35/00

See application file for complete search history.

(56) References Cited

U.S. PATENT DOCUMENTS

| | | |
|---|---|---|
| 5,122,464 A | 6/1992 | Wilson et al. |
| 5,225,539 A | 7/1993 | Winter |
| 5,530,101 A | 6/1996 | Queen et al. |
| 5,565,332 A | 10/1996 | Hoogenboom et al. |
| 5,585,089 A | 12/1996 | Queen et al. |
| 5,766,886 A | 6/1998 | Studnicka et al. |
| 5,837,242 A | 11/1998 | Holliger et al. |
| 5,869,620 A | 2/1999 | Whitlow et al. |
| 5,989,830 A | 11/1999 | Davis et al. |
| 6,005,079 A | 12/1999 | Casterman et al. |
| 6,132,992 A | 10/2000 | Ledbetter et al. |
| 6,407,213 B1 | 6/2002 | Carter et al. |
| 7,183,076 B2 | 2/2007 | Arathoon et al. |
| 7,659,241 B2 | 2/2010 | Senter et al. |
| 7,829,531 B2 | 11/2010 | Senter et al. |
| 7,851,437 B2 | 12/2010 | Senter et al. |
| 7,951,917 B1 | 5/2011 | Arathoon et al. |
| 8,227,577 B2 | 7/2012 | Klein et al. |
| 8,541,178 B2 | 9/2013 | Kaur et al. |
| 8,586,713 B2 | 11/2013 | Davis et al. |
| 10,221,248 B2 * | 3/2019 | Tavazoie ................ C07K 16/40 |
| 11,225,524 B2 * | 1/2022 | Tavazoie ............ A61K 31/4535 |
| 11,242,407 B2 * | 2/2022 | Tavazoie ................ A61K 47/65 |

(Continued)

FOREIGN PATENT DOCUMENTS

| | | |
|---|---|---|
| EP | 519596 A1 | 12/1992 |
| EP | 592106 A1 | 4/1994 |

(Continued)

OTHER PUBLICATIONS

Lambert, et al., J. Med. Chem. 2014 57:6949 (Year: 2014).*

(Continued)

*Primary Examiner* — Julie Wu
*Assistant Examiner* — Sydney Van Druff
(74) *Attorney, Agent, or Firm* — Fox Rothschild LLP

(57) ABSTRACT

The present disclosure provides antibody-drug conjugates comprising (i) antibodies that specifically bind to Mer Tyrosine Kinase (MERTK) (e.g., human MERTK, or both human and mouse MERTK), and (ii) cytotoxic agents conjugated directly to the antibodies or conjugated to the antibodies via linkers, and compositions comprising such antibody-drug conjugates, wherein the antibodies contained in the antibody-drug conjugates agonize MERTK signaling of endothelial cells. The present disclosure also provides methods for treating cancer, by administering an antibody-drug conjugate that comprises (i) an antibody that specifically binds to MERTK and agonizes MERTK signaling of endothelial cells, and (ii) a cytotoxic agent conjugated directly to the antibody or conjugated to the antibody via a linker.

29 Claims, 12 Drawing Sheets

Figure 3:
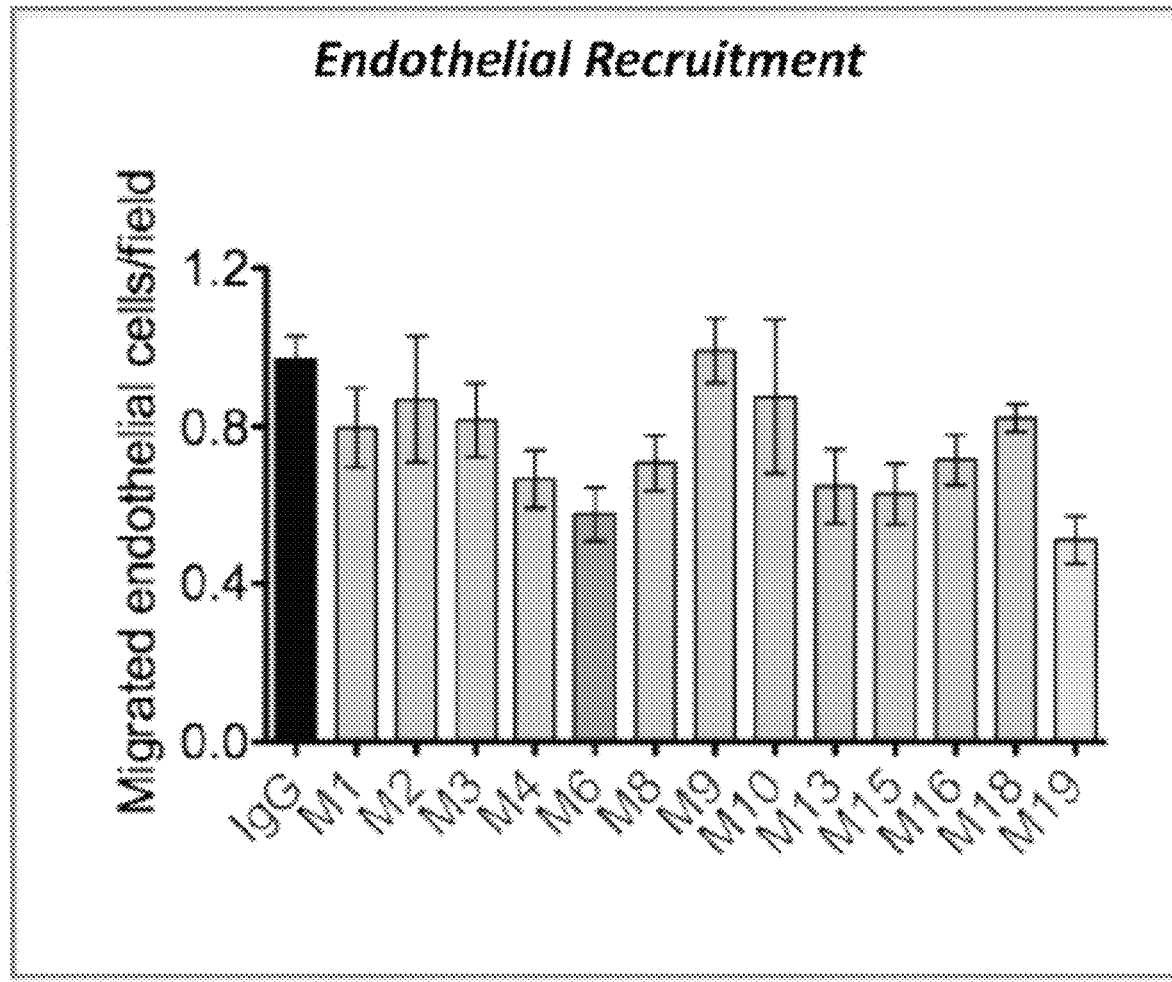

Specification includes a Sequence Listing.

(56) References Cited

U.S. PATENT DOCUMENTS

| | | |
|---|---|---|
| 2005/0042664 A1 | 2/2005 | Wu et al. |
| 2005/0048549 A1 | 3/2005 | Cao et al. |
| 2010/0266604 A1 | 10/2010 | Rothlin et al. |
| 2012/0135424 A1 | 5/2012 | Graham et al. |
| 2013/0309243 A1 | 11/2013 | Perreau et al. |
| 2015/0315552 A1 | 11/2015 | Giaccia et al. |
| 2018/0002444 A1 | 1/2018 | Tavazoie et al. |
| 2019/0241676 A1 | 8/2019 | Tavazoie et al. |
| 2020/0291135 A1 | 9/2020 | Tavazoie et al. |

FOREIGN PATENT DOCUMENTS

| | | |
|---|---|---|
| EP | 239400 | 8/1994 |
| JP | 2011514881 A | 5/2011 |
| JP | 2017-511376 A | 4/2017 |
| WO | 8605807 A1 | 10/1986 |
| WO | 8901036 A1 | 2/1989 |
| WO | 9109967 A1 | 7/1991 |
| WO | 9317105 A1 | 9/1993 |
| WO | 1994/04678 A1 | 3/1994 |
| WO | 1994/025591 | 11/1994 |
| WO | 0144301 A1 | 6/2001 |
| WO | 2010008411 A1 | 1/2010 |
| WO | 2014/093707 A1 | 6/2014 |
| WO | 2015143382 A1 | 9/2015 |
| WO | 2016106221 A1 | 6/2016 |
| WO | 2019005756 A1 | 1/2019 |

OTHER PUBLICATIONS

Nguyen, et al., J. Biol. Chem. 2014 37:25737 (Year: 2014).*
Von Minkwitz, et al., N. Engl. J. Med. 2012 366:299 (Year: 2012).*
Schlegel, et al., J. Clin. Invest. 2013 123:2257 (Year: 2013).*
Jiang, et al., PLOS One 2013 9(13): e11920 (Year: 2013).*
Casi, et al., J. Controlled Release 2012 161:422 (Year: 2012).*
Almagro & Fransson, Frontiers in Bioscience 2008; 13:1619-33.
Ausubel et al., eds, 1989, Current Protocols in Molecular Biology, vol. I, Green Publishing Associates, Inc. and John Wiley & Sons, Inc., New York:6.3.1-6.3.6 and 2.10.3.
Axelrod et al., "Axl as a mediator of cellular growth and survival," Oncotarget (2014); 5(19):8818-8852.
Baca et al., 1997, "Antibody Humanization Using Monovalent Phage Display", J Biol Chem, 272(16):10678-10684.
Beck et al., "Strategies and challenges for the next generation of antibody-drug conjugates", Nature Reviews Drug Discovery, vol. 16, No. 5, 2017, pp. 315-337.
Bosurgi et al., "Paradoxical role of the proto-oncogene Axl and Mer receptor tyrosine kinases in colon cancer," PNAS (Aug. 6, 2013); 110(32):13091-13096.
Caldas et al., 2000, "Design and synthesis of germline-based hemi-humanized single-chain Fv against the CD18 surface antigen", Protein Eng, 13(5):353-360.
Cannarile et al., "Colony-stimulating factor 1 receptor (CSF1R) inhibitors in cancer therapy," J Immunother Cancer. Jul. 18, 2017;5(1):53.
Cardillo et al., 2011, "Humanized Anti-Trop-2 IgG-SN-38 Conjugate for Effective Treatment of Diverse Epithelial Cancers: Preclinical Studies in Human Cancer Xenograft Models and Monkeys", Clin Cancer Res, 17(10):3157-3169.
Chen et al., "Identification of Gas6 as a ligand for Mer, a neural cell adhesion molecule related receptor tyrosine kinase implicated in cellular transformation," Oncogene (1997); 14:2033-2039.
Clackson et al., 1991, "Making antibody fragments using phage display libraries", Nature, 352(6336):624-628.
Cockett et al., 1990, "High Level Expression of Tissue Inhibitor of Metalloproteinases in Chinese Hamster Ovary Cells Using Glutamine Synthetase Gene Amplification", Biotechnology, 8(7):662-667.
Cook et al., 2013, "MerTK inhibition in tumor leukocytes decreases tumor growth and metastasis", J Clin Invest, 123 (8):3231-3242.
Couto et al., 1995, "Anti-BA46 Monoclonal Antibody Mc3: Humanization Using a Novel Positional Consensus and in Vivo and in Vitro Characterization", Cancer Res, 55(8):1717-1722.
Couto et al., 1995, "Designing Human Consensus Antibodies with Minimal Positional Templates", Cancer Res, 55(23 Suppl):5973s-5977s.
Crittenden et al., 2016, "Mertk on tumor macrophages is a therapeutic target to prevent tumor recurrence following radiation therapy", Oncotarget, 7(48):78653-78666.
Cummings et al., "Mer590, a novel monoconal antibody targeting MER receptor tyrosine kinase, decreases colony formation and increases chemosensitivity in no-small cell lung cancer," Oncotarget (2014); 5(21):10434-10445.
Cummings et al., 2013, "Molecular Pathways: MERTK Signaling in Cancer", Clin Cancer Res, 19(19):5275-5280.
Dondelinger et al., "Understanding the Significance and Implications of Antibody Numbering and Antigen-Binding Surface/Residue Definition", Frontiers in Immunology, vol. 9, 2018, pp. 1-15.
Edwards et al, J Mol Biol 2003 334: 103-118.
Fauvel et al., "Antibodies directed against receptor tyrosine kinases", MABS, vol. 6, No. 4, 2014, pp. 838-851.
Foecking and Hofstetter, 1986, "Powerful and versatile enhancer-promoter unit for mammalian expression vectors", Gene, 45(1):101-105.
Gallicchio et al., "Inhibition of vascular endothelial growth factor receptor 2-mediated endothelial cell activation by Axl tyrosine kinase receptor," Blood (Mar. 1, 2005); 105(5):1970-1976.
Goldenberg et al., 2018, "The emergence of trophoblast cell-surface antigen 2 (TROP-2) as a novel cancer target", Oncotarget, 9(48):28989-29006.
Jackson, 2016, "Processes for Constructing Homogeneous Antibody Drug Conjugates", Org Process Res Dev, 20 (5):852-866.
Japanese Office Action mailed Apr. 26, 2022 in Japanese Patent Application No. 2022-522279, 14 pages.
Kim and Hong, 2007, "Guided selection of human antibody light chains against TAG-72 using a phage display chain shuffling approach", J Microbiol, 45(6):572-577.
Kim et al., Biomol. Ther. 2015 23(6), pp. 493-509 (Year: 2015).
Kutmeier et al., 1994, "Assembly of humanized antibody genes from synthetic oligonucleotides using a single-round PCR", BioTechniques, 17(2):242-246.
Linger et al., "TAM Receptor Tyrosine Kinases: Biologic Functions, Signaling, and Potential Therapeutic Targeting in Human Cancer," Advances Cancer Research (2008); 100:35-83.
Linger et al., 2013, "Mer or Axl Receptor Tyrosine Kinase Inhibition Promotes Apoptosis, Blocks Growth, and Enhances Chemosensitivity of Human Non-Small Cell Lung Cancer", Oncogene, 32(29):3420-3431.
Liu et al., 2013, "UNC1062, a new and potent Mer inhibitor", Eur J Med Chem, 65:83-93.
Marchalonis et al., Dev & Comp Immunol 2006 30:223-247.
Mccombs and Owen, 2015, "Antibody Drug Conjugates: Design and Selection of Linker, Payload and Conjugation Chemistry", AAPS J, 17(2):339-351.
Meibohm (Pharmacokinetics and Pharmacodynamics of Biotech Drugs, Wiley-VHC, 2006, chapter 3, p. 45-91) (Year: 2006).
Miner et al., "The TAM receptor Mertk protects against neuroinvasive viral infection by maintaing blood-brain barrier integrity," Nature Medicine (Dec. 2015); 21(12):1464-1472.
Minn et al., 2005, "Genes That Mediate Breast Cancer Metastasis to Lung", Nature, 436(7050):518-524.
Morea et al., 2000, "Antibody modeling: Implications for engineering and design", Methods, 20(3):267-279.
Muyldermans, 2001, "Single Domain Camel Antibodies: Current Status", J Biotechnol, 74(4):277-302.
Nejadmoghaddam et al., "Antibody-Drug Conjugates: Possibilities and Challenges", Avicenna Journal of Medical Biotechnology, 2019, pp. 3-23.
Nuttall et al., 2000, "Immunoglobulin VH domains and beyond: design and selection of single-domain binding and targeting reagents", Curr Pharm Biotehnol, 1(3):253-263.

(56) References Cited

OTHER PUBLICATIONS

Padlan, 1991, "A Possible Procedure for Reducing the Immunogenicity of Antibody Variable Domains While Preserving Their Ligand-Binding Properties", Mol Immunol, 28(4/5):489-498.
Pedersen et al., 1994, "Comparison of Surface Accessible Residues in Human and Murine Immunoglobulin Fv Domains. Implication for Humanization of Murine Antibodies", J Mol Biol, 235(3):959-973.
Peters and Brown, 2015, "Antibody-drug conjugates as novel anti-cancer chemotherapeutics", Biosci Rep, 35(4):art: e00225.
Pietronave, S. et al., "Agonist monoclonal antibodies against HGF receptor protect cardiac muscle cells from apoptosis", Am. J. Physiol. Heart Circ. Physiol., (2010), vol. 298, pp. H1155-H1165.
Png et al., "A microRNA regulon that mediates endothelial recruitment and metastasis by cancer cells," Nature Jan. 12, 2012); 481:190-194.
Prat, M. et al., "Monoclonal Antibodies against the MET/HGF Receptor and Its Ligand: Multitask Tools with Applications from Basic Research to Therapy", Biomedicines, (Dec. 3, 2014, vol. 2, pp. 359-383.
Presta, L. G. et al., "Humanization of an Anti-Vascular Endothelial Growth Factor Monoclonal Antibody for the Therapy of Solid Tumors and Other Disorders", Cancer Res., (1997), vol. 57, pp. 4593-4599.
Qian, M. D. et al., "Novel Agonist Monoclonal Antibodies Activate TrkB Receptors and Demonstrate Potent Neurotrophic Activities", J. Neurosci. (2006), vol. 26, No. 37, pp. 93-9403.
Rader et al., 1998, "A phage display approach for rapid antibody humanization: Designed combinatorial V gene libraries", Proc Natl Acad Sci USA, 95(15):8910-8915.
Reichmann and Muyldermans, 1999, "Single Domain Antibodies: Comparison of Camel VH and Camelised Human VH Domains", J Immunol, 231:25-38.
Rogers, et al., Oncogene (2012) vol. 31, pp. 4171-4181.
Roguska et al., 1994, "Humanization of murine monoclonal antibodies through variable domain resurfacing", Proc Natl Acad Sci USA, 91(3):969-973.
Roguska et al., 1996, "A comparison of two murine monoclonal antibodies humanized by CDR-grafting and variable domain resurfacing", Protein Eng, 9(10):895-904.
Sandhu, 1994, "A rapid procedure for the humanization of monoclonal antibodies", Gene, 150(2):409-410.
Sather et al., "A soluble form of the Mer receptor tyrosine kinase inhibits macrophage clearance of apoptotic cells and platelet aggregation," Blook (Feb. 1, 2007); 109(3):1-17.
Shao et al., "A protective role of Mer receptor tyrosine kinase in nephrotoxic serum-induced nephritis," Clinical Immunology (2010); 135:236-244.
Studnicka et al., 1994, "Human-engineered monoclonal antibodies retain full specific binding activity by preserving non-CDR complementarity-modulating residues.", Prot Engineering, 7(6):805-814.
Tan et al., 2002, ""Superhumanized" Antibodies: Reduction of Immunogenic Potential by Complementarity-Determining Region Grafting with Human Germline Sequences: Application to an Anti-CD28", J Immunol, 169:1119-1125.
Verma et al., "Targeting Axl and Mer Kinases in Cancer," Mol. Cancer Ther. (Oct. 2011); 10(10):1763-1773 (Published Online Sep. 1, 2011).
Waterborg et al., "Protective Role of the MER Tyrosine Kinase via Efferocytosis in Rheumatoid Arthritis Models," Frontiners in Immunology (Apr. 13, 2018); vol. 9, Article 742: pp. 1-14.
White et al. (2001, Ann. Rev. Med., 2001, 52:125-145) (Year: 2001).
Zagorska et al., "Diversification of TAM receptor function," Nat Immunol. (Oct. 2014); 15(10):920-928.
Zizzo et al., 2012, "Efficient Clearance of Early Apoptotic Cells by Human Macrophages Requires M2c Polarization and MerTK Induction", J Immunology, 189(7):3508-3520.

* cited by examiner

Figure 1A

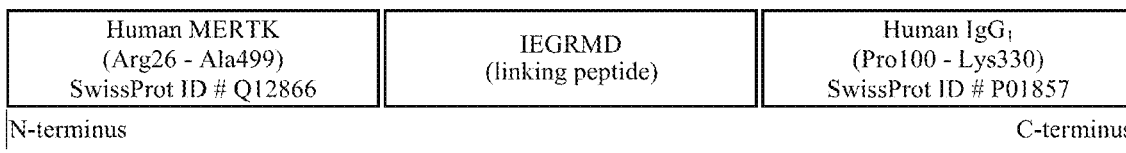

Figure 1B

```
1    mgpaplplll glflpalwrr aiteareeak pyplfpgpfp gslqtdhtpl
lslphasgyq         61   palmfsptqp grphtgnvai pqvtsveskp lpplafkhtv
ghiilsehkg vkfncsisvp         121 niyqdttisw wkdgkellga hhaitqfypd
devtaiiasf sitsvqrsdn gsyickmkin        181 neeivsdpiy ievqglphft
kqpesmnvtr ntafnltcqa vgppepvnif wvqnssrvne       241 qpekspsvlt
vpgltemavf sceahndkgl tvskgvqini kaipspptev sirnstahsi        301
liswvpgfdg yspfrncsiq vkeadplsng svmifntsal phlyqikqlq alanysigvs
361 cmneigwsav spwilastte gapsvaplnv tvflnessdn vdirwmkppt
kqqdgelvgy       421 rishvwqsag iskelleevg qngsrarisv qvhnatctvr
iaavtrggvg pfsdpvkifi         481 pahgwvdyap sstpapgnad pvliifgcfc
gfiligllly islairkrvq etkfgnafte        541 edselvvnyi akksfcrrai
eltlhslgvs eelqnkledv vidrnllilg kilgegefgs       601 vmegnlkqed
gtslkvavkt mkldnssqre ieeflseaac mkdfshpnvi rllgvciems        661
sqgipkpmvi lpfmkygdlh tyllysrlet gpkhiplqtl lkfmvdialg meylsnrnfl
721 hrdlaarncm lrddmtvcva dfglskkiys gdyyrqgria kmpvkwiaie
sladrvytsk         781 sdvwafgvtm weiatrgmtp ypgvqnhemy dyllhghrlk
qpedcldely eimyscwrtd         841 pldrptfsvl rlqleklles lpdvrnqadv
iyvntqlles seglaqgstl apldlnidpd        901 siiasctpra aisvvtaevh
dskphegryi lnggseewed ltsapsaavt aeknsvlpge       961 rlvrngvsws
hssmlplgss lpdellfadd ssegsevlm
```

MerTK monoclonal antibody screen

| Designator | O.D. by ELISA Vs. Mer | Blocking O.D. (Mer +Clone) |
|---|---|---|
| M1 | 1.307 | 2.922 |
| M2 | 0.746 | 2.744 |
| M3 | 0.949 | 2.718 |
| M4 | 4.000 | 2.842 |
| M5 | 1.377 | 2.508 |
| M6 | 4.000 | 2.048 |
| M7 | 1.304 | 2.735 |
| M8 | 3.764 | 2.729 |
| M9 | 1.006 | 2.715 |
| M10 | 3.160 | 2.699 |
| M11 | 4.000 | 1.809 |
| M12 | 4.000 | 1.840 |
| M13 | 4.000 | 1.759 |
| M14 | 4.000 | 1.806 |
| M15 | 3.705 | 1.448 |
| M16 | 3.777 | 1.557 |
| M17 | 4.000 | 1.639 |
| M18 | 4.000 | 1.567 |
| M19 | 4.000 | 1.517 |
| M20 | 4.000 | 1.726 |

Figure 2

| ER-M19 vs. hMer Affinity | | | | | |
|---|---|---|---|---|---|
| Concentration hMer (nM) | Response (nm) | $K_D$ (M) | $k_{on}$(1/Ms) | $k_{dis}$(1/s) | Full R^2 |
| 5 | 0.7942 | 2.46E-10 | 3.86E+06 | 9.51E-04 | 0.956793 |
| 2.5 | 0.5448 | 3.39E-10 | 2.65E+06 | 8.99E-04 | 0.983587 |
| 1.25 | 0.3565 | 2.97E-10 | 3.44E+06 | 1.02E-03 | 0.985297 |
| 0.625 | 0.2551 | 1.55E-10 | 5.11E+06 | 7.90E-04 | 0.984157 |
| 0.3125 | 0.1347 | 1.28E-10 | 7.57E+06 | 9.68E-04 | 0.985513 |
| 0.1563 | 0.0667 | 6.21E-10 | 1.53E+06 | 9.49E-04 | 0.993774 |
| 0.0781 | 0.0404 | 7.65E-11 | 1.22E+07 | 9.34E-04 | 0.973438 |
| GLOBAL FIT: | | 3.26E-10 | 3.08E+06 | 1.00E-03 | 0.99598 |

Abbreviations Key
Response Wavelength Shift calculated during the association step (nm)
$K_D$    Affinity Constant (M) = $K_{dis}/K_{on}$
$k_{on}$    Rate of Association (1/Ms)
$k_{dis}$    Rate of Dissociation (1/s)
Full $R^2$    Correlation Coefficient for Curve Fitting

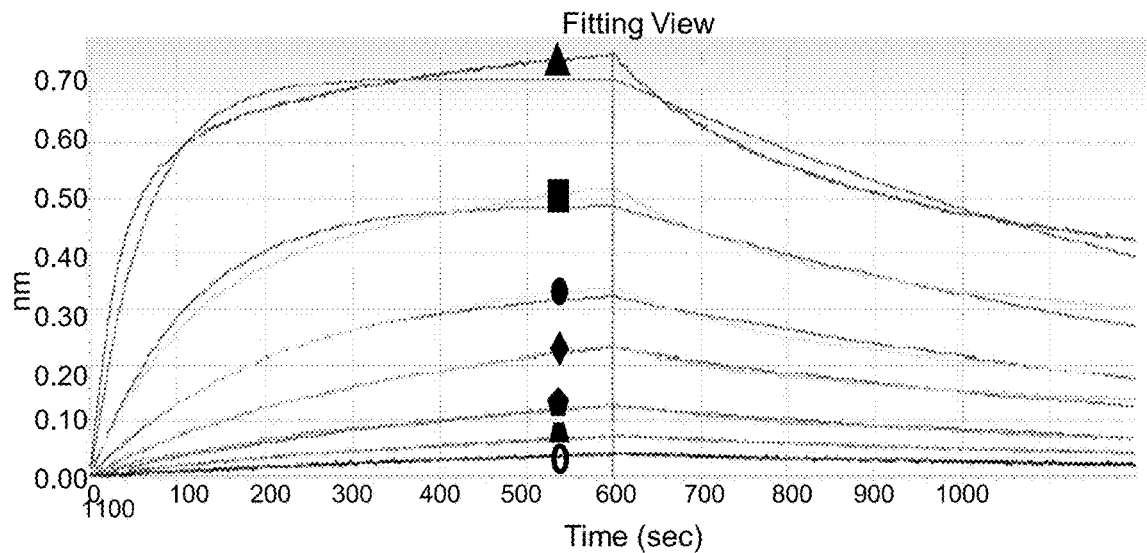

Figure Key Concentration (nM)
▲ 5
■ 2.5
● 1.25
◆ 0.625
⬟ 0.3125
▴ 0.15625
○ 0.078125

Figure 7

| MER-M19 vs. msMer Affinity | | | | | |
|---|---|---|---|---|---|
| Concentration msMer (nM) | Response (nm) | $K_D$ (M) | $k_{on}$ (1/Ms) | $k_{dis}$ (1/s) | Full R^2 |
| 5 | 0.4374 | 3.54E-10 | 3.77E+06 | 1.33E-03 | 0.968567 |
| 2.5 | 0.363 | 3.41E-10 | 4.66E+06 | 1.59E-03 | 0.982899 |
| 1.25 | 0.2775 | 2.82E-10 | 5.27E+06 | 1.49E-03 | 0.983871 |
| 0.625 | 0.214 | 1.98E-10 | 6.92E+06 | 1.37E-03 | 0.989074 |
| 0.3125 | 0.1427 | 1.15E-10 | 9.23E+06 | 1.06E-03 | 0.986706 |
| 0.1563 | 0.0795 | 1.17E-10 | 1.10E+07 | 1.29E-03 | 0.987989 |
| 0.0781 | 0.0428 | 4.72E-11 | 2.29E+07 | 1.08E-03 | 0.961076 |
| GLOBAL FIT: | | 3.05E-10 | 4.71E+06 | 1.44E-03 | 0.99318 |

Abbreviations Key
Response Wavelenth Shift calculated during the association step (nm)
$K_D$   Affinity Constant (M) = $k_{dis}/k_{on}$
$k_{on}$   Rate of Association (1/Ms)
$k_{dis}$   Rate of Dissociation (1/s)
Full $R^2$   Correlation Coefficient for Curve Fitting

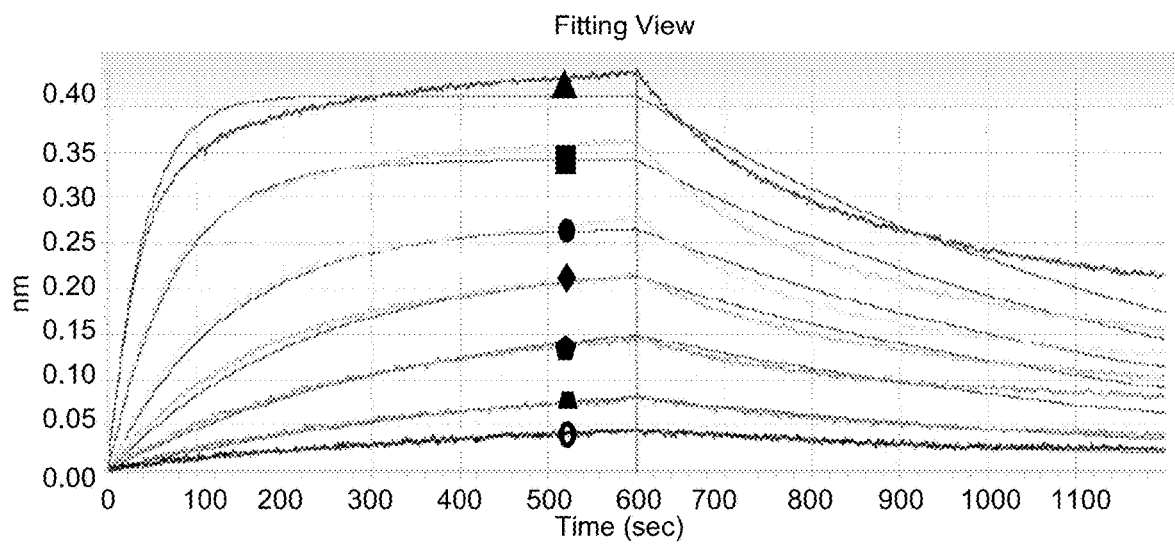

Fitting View

Figure Key
Concentration (nM)

▲ 5
■ 2.5
● 1.25
♦ 0.625
⬟ 0.3125
▬ 0.15625
○ 0.078125

Figure 8

| MER-M6 vs. hMer Affinity | | | | | |
|---|---|---|---|---|---|
| Concentration hMer (nM) | Response (nm) | $K_D$ (M) | $k_{on}$(1/Ms) | $k_{dis}$(1/s) | Full R^2 |
| 5 | 0.5449 | 6.34E-13 | 2.37E+06 | 1.50E-06 | 0.937992 |
| 2.5 | 0.3941 | 2.09E-12 | 2.13E+06 | 4.46E-06 | 0.986368 |
| 1.25 | 0.2669 | 4.98E-11 | 3.12E+06 | 1.56E-04 | 0.98301 |
| 0.625 | 0.1835 | 1.31E-14 | 5.57E+06 | 7.27E-08 | 0.872407 |
| 0.3125 | 0.1009 | 3.12E-15 | 1.06E+07 | 3.30E-08 | 0.834831 |
| 0.1563 | 0.0373 | 6.52E-14 | 1.41E+07 | 9.22E-07 | 0.800002 |
| 0.0781 | 0.0173 | 8.23E-13 | 3.03E+07 | 2.49E-05 | 0.816043 |
| GLOBAL FIT: | | 4.61E-12 | 2.07E+06 | 9.55E-06 | 0.997574 |

Abbreviations Key
Response Wavelenth Shift calculated during the association step (nm)
$K_D$    Affinity Constant (M) = $k_{dis}/k_{on}$
$k_{on}$    Rate of Association (1/Ms)
$k_{dis}$    Rate of Dissociation (1/s)
Full $R^2$    Correlation Coefficient for Curve Fitting

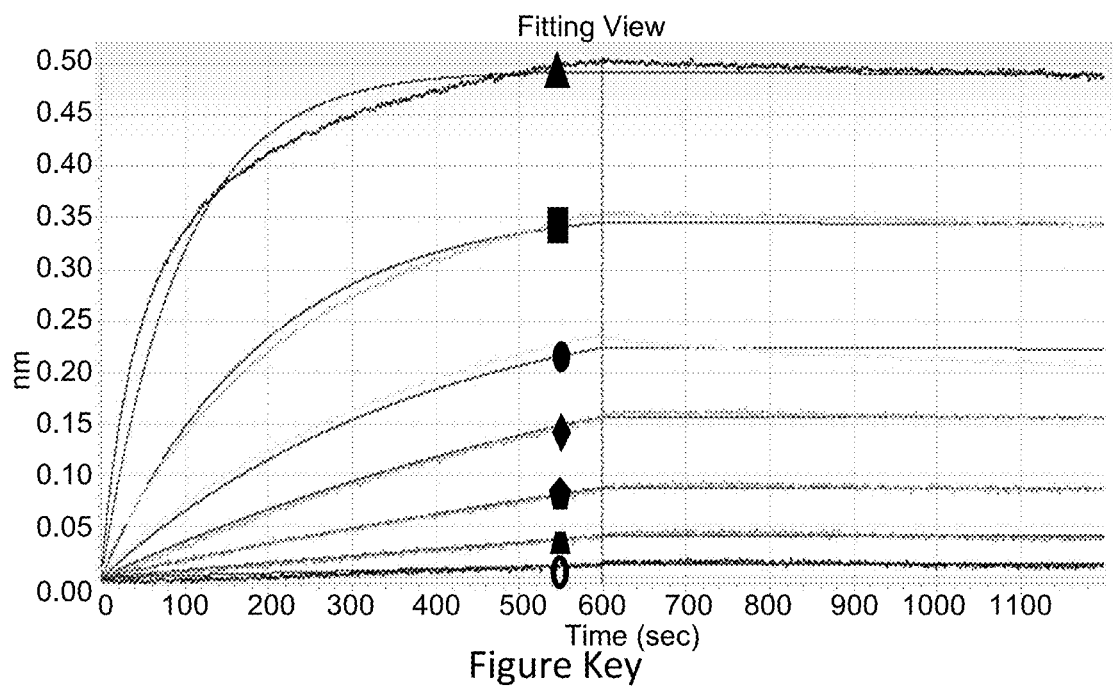

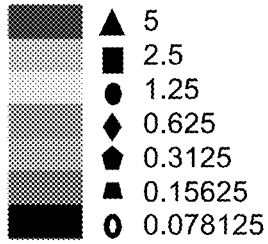

Figure 11

ANTI-MERTK AGONISTIC ANTIBODIES AND USES THEREOF

CROSS-REFERENCE TO RELATED APPLICATIONS

The present application is a Divisional of U.S. application Ser. No. 16/626,456, which is a National Stage Application under 35 U.S.C. § 371 of International Application No. PCT/US18/39445 filed Jun. 26, 2018, which claims priority under 35 U.S.C. § 119(e) to U.S. Provisional Patent Application No. 62/525,993, filed Jun. 28, 2017, the disclosures of all of which are incorporated herein by reference in their entireties.

PARTIES TO A JOINT RESEARCH AGREEMENT

The subject matter of this application was made as a result of activities undertaken within the scope of a joint research agreement between The Rockefeller University and Rgenix, Inc. (Rgenix, Inc. being now known as Inspirna, Inc.).

REFERENCE TO SEQUENCE LISTING SUBMITTED ELECTRONICALLY

This application incorporates by reference a Sequence Listing submitted with this application as a ST.26 xml file entitled "070413.20716.xml" created on Dec. 6, 2022 and having a size of 74 kilobytes.

1. FIELD

The present disclosure provides antibody-drug conjugates comprising (i) antibodies that specifically bind to Mer Tyrosine Kinase (MERTK) (e.g., human MERTK, or both human and mouse MERTK), and (ii) cytotoxic agents conjugated directly to the antibodies or conjugated to the antibodies via linkers, and compositions comprising such antibody-drug conjugates, wherein the antibodies contained in the antibody-drug conjugates agonize MERTK signaling of endothelial cells. The present disclosure also provides methods for treating cancer, by administering an antibody-drug conjugate that comprises (i) an antibody that specifically binds to MERTK and agonizes MERTK signaling of endothelial cells, and (ii) a cytotoxic agent conjugated directly to the antibody or conjugated to the antibody via a linker.

2. BACKGROUND

Mer Tyrosine Kinase (MERTK), also referred to as c-mer, MER, Proto-oncogene c-Mer, Receptor Tyrosine Kinase MerTK, Tyrosine-protein Kinase Mer, STK Kinase, RP38, or MGC133349, is a member of the TAM family of receptor tyrosine kinases, which also include AXL and TYRO3 kinases. MERTK transduces signals from the extracellular space via activation by binding of ligands, most notably Gas-6, a soluble protein. Gas-6 binding to MERTK induces autophosphorylation of MERTK on its intracellular domain, resulting in downstream signal activation (Cummings C T et al., (2013) Clin Cancer Res 19: 5275-5280; Verma A et al., (2011) Mol Cancer Ther 10: 1763-1773).

The MERTK receptor exists in both membrane bound and soluble forms. The extracellular domain can be cleaved to generate a soluble extracellular domain, which is hypothesized to act as a decoy receptor to negatively regulate MERTK receptor activation on cells by reducing the ability and/or availability of soluble Gas-6 ligand to bind membrane-bound MERTK (Sather S et al., (2007) Blood 109: 1026-1033). As a result, MERTK has dual roles related to cancer progression, angiogenesis, and metastasis. On the one hand, Gas-6 activation of MERTK on endothelial cells results in inhibition of endothelial cell recruitment by cancer cells in a co-culture system. Endothelial recruitment is a key feature of cancer cells that allows for tumor angiogenesis, tumor growth, and metastasis. However, on the other hand, MERTK plays an opposite role in cancer cells, where its over-expression leads to increased metastasis, likely by releasing cleaved MERTK to generate soluble MERTK extracellular domain protein as a decoy receptor. Thus, tumor cells secrete a soluble form of the extracellular MERTK receptor that acts as a decoy receptor to reduce the ability (and/or availability) of soluble Gas-6 ligand to activate MERTK on endothelial cells, ultimately leading to endothelial recruitment, angiogenesis, and cancer progression (Png K J et al., (2012) Nature 481: 190-194).

Historically, there have been efforts to generate inhibitors, but not activators, of MERTK for the treatment of cancer (e.g., compound UNC1062, a potent small molecule MERTK inhibitor developed as an anticancer compound), because MERTK was thought to solely function as an oncogene (Liu J et al., (2013) Eur J Med Chem 65: 83-93; Cummings C T et al., (2013) Clin Cancer Res 19: 5275-5280; Verma A et al., (2011) Mol Cancer Ther 10: 1763-1773). Given the dual role of MERTK in cancer cells and endothelial cells, treatment with a molecule that generally results in MERTK activation (e.g., on both endothelial cells and cancer cells) could result in increased endothelial cell recruitment and metastasis. However, a compound that activates MERTK signaling of endothelial cells but not cancer cells would potentially be an attractive therapeutic for tumor angiogenesis and metastasis.

Thus, there is a need for therapeutic options involving antibodies that specifically bind to MERTK and agonize MERTK signaling of endothelial cells.

In recent years, antibody-drug conjugates (ADCs) have become one of the fastest growing classes of cancer therapeutics (Beck A et al., (2017) Nat Rev Drug Discov 16: 315-337; Peters C and Brown S, (2015) Biosci Rep 35: art:e00225).

Citation of a reference herein shall not be construed as an admission that such is prior art to the present disclosure.

3. SUMMARY

The invention provides an antibody-drug conjugate comprising: (a) an antibody moiety that is an antibody or antigen-binding fragment thereof that specifically binds to MERTK (e.g., human MERTK, or both human and mouse MERTK) and agonizes human MERTK signaling of endothelial cells; (b) one or more drug moieties, each drug moiety being a cytotoxic agent; and (c) optionally a linker; wherein the cytotoxic agent is conjugated directly to the antibody moiety or is conjugated to the antibody moiety via the linker.

Non-limiting exemplary anti-MERTK antibodies or antigen-binding fragments thereof that can be the antibody moiety of the antibody-drug conjugates of the invention are described below.

In a specific embodiment, an anti-MERTK antibody or antigen-binding fragment thereof described herein specifically recognizes the extracellular domain of human MERTK. In another specific embodiment, an anti-MERTK antibody or antigen-binding fragment thereof described herein specifically recognizes the extracellular domain of mouse MERTK. In another particular embodiment, an anti-MERTK antibody or antigen-binding fragment thereof described herein competes with Gas-6 for binding to MERTK (e.g., human MERTK, or both human and mouse MERTK). In a particular embodiment, an anti-MERTK antibody or antigen-binding fragment described herein is monoclonal. In another particular embodiment, an anti-MERTK antibody or antigen-binding fragment thereof described herein is an immunoglobulin comprising two identical light chains and two identical heavy chains.

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
(SEQ ID NO: 1)
NYGMN;
and/or (b) a VH CDR2 of
(SEQ ID NO: 6)
WINTYTGEPTYADDFKG;
and/or (c) a VH CDR3 of
(SEQ ID NO: 11)
KSTVVSRYFDV.

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
(SEQ ID NO: 2)
GYTFTNY;
and/or (b) a VH CDR2 of;
(SEQ ID NO: 7)
and/or (c) a VH CDR3 of
(SEQ ID NO: 12)
STVVSRYFD.

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
(SEQ ID NO: 3)
GYTFTNYGMN;
and/or (b) a VH CDR2 of
(SEQ ID NO: 8)
WINTYTGEPT;
and/or (c) a VH CDR3 of
(SEQ ID NO: 11)
KSTVVSRYFDV In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
(SEQ ID NO: 4)
TNYGMN;
and/or (b) a VH CDR2 of
(SEQ ID NO: 9)
WMGWINTYTGEPT;
and/or (c) a VH CDR3 of
(SEQ ID NO: 13)
ARKSTVVSRYFD.

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
(SEQ ID NO: 5)
GYTFTNYG;
and/or (b) a VH CDR2 of
(SEQ ID NO: 10)
INTYTGEP;
and/or (c) a VH CDR3 of
(SEQ ID NO: 14)
ARKSTVVSRYFDV.

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
GYTFTNYGMN; (SEQ ID NO: 3)
and/or (b) a VH CDR2 of
WINTYTGEPTYADDFKG; (SEQ ID NO: 6)
and/or (c) a VH CDR3 of
KSTVVSRYFDV. (SEQ ID NO: 11)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of
KASQDVGDAVT; (SEQ ID NO: 15)
and/or (b) a VL CDR2 of
WASTRHT; (SEQ ID NO: 19)
and/or (c) a VL CDR3 of
QQYRSYPLT. (SEQ ID NO: 22)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of
SQDVGDA; (SEQ ID NO: 16)
and/or (b) a VL CDR2 of
WAS; (SEQ ID NO: 20)
and/or (c) a VL CDR3 of
YRSYPL. (SEQ ID NO: 23)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of
GDAVTWC; (SEQ ID NO: 17)
and/or (b) a VL CDR2 of
LLIYWASTRH; (SEQ ID NO: 21)
and/or (c) a VL CDR3 of
QQYRSYPL. (SEQ ID NO: 24)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of
QDVGDA; (SEQ ID NO: 18)
and/or (b) a VL CDR2 of
WAS; (SEQ ID NO: 20)
and/or (c) a VL CDR3 of
QQYRSYPLT. (SEQ ID NO: 22)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of
DYSMH; (SEQ ID NO: 25)
and/or (b) a VH CDR2 of
WINTDTGEPTYADDFKG; (SEQ ID NO: 30)
and/or (c) a VH CDR3 of
WFGAMDY. (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of
NYTFTDY; (SEQ ID NO: 26)
and/or (b) a VH CDR2 of
TDTG; (SEQ ID NO: 31)
and/or (c) a VH CDR3 of
FGAMD. (SEQ ID NO: 36)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of
        NYTFTDYSMH; (SEQ ID NO: 27)
and/or (b) a VH CDR2 of
        WINTDTGEPT; (SEQ ID NO: 32)
and/or (c) a VH CDR3 of
        WFGAMDY (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of
        TDYSMH; (SEQ ID NO: 28)
and/or (b) a VH CDR2 of
        WVGWINTDTGEPT; (SEQ ID NO: 33)
and/or (c) a VH CDR3 of
        ARWFGAMD. (SEQ ID NO: 37)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of
        NYTFTDYS; (SEQ ID NO: 29)
and/or (b) a VH CDR2 of
        INTDTGEP; (SEQ ID NO: 34)
and/or (c) a VH CDR3 of
        ARWFGAMDY. (SEQ ID NO: 38)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of
        NYTFTDYSMH; (SEQ ID NO: 27)
and/or (b) a VH CDR2 of
        WINTDTGEPTYADDFKG; (SEQ ID NO: 30)
and/or (c) a VH CDR3 of
        WFGAMDY. (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
        KASQDVTNVVA; (SEQ ID NO: 39)
and/or (b) a VL CDR2 of
        SASYRYT; (SEQ ID NO: 43)
and/or (c) a VL CDR3 of
        QQYYRTPRT. (SEQ ID NO: 46)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
        SQDVTNV; (SEQ ID NO: 40)
and/or (b) a VL CDR2 of
        SAS; (SEQ ID NO: 44)
and/or (c) a VL CDR3 of
        YYRTPR. (SEQ ID NO: 47)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
        TNVVAWY; (SEQ ID NO: 41)
and/or (b) a VL CDR2 of
        LLIYSASYRY; (SEQ ID NO: 45)
and/or (c) a VL CDR3 of
        QQYYRTPR. (SEQ ID NO: 48)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
                    (SEQ ID NO: 42)
QDVTNV;
and/or (b) a VL CDR2 of
                    (SEQ ID NO: 44)
SAS;
and/or (c) a VL CDR3 of
                    (SEQ ID NO: 46)
QQYYRTPRT.

In specific embodiments, the anti-MERTK antibody or antigen-binding fragment thereof comprises one, two, or all three of the VH CDRs above. In certain embodiments, the antibody or antigen-binding fragment thereof comprises a VH CDR1 in Table 1 or Table 3. In some embodiments, the anti-MERTK antibody or antigen-binding fragment thereof comprises a VH CDR2 in Table 1 or Table 3. In certain embodiments, the anti-MERTK antibody or antigen-binding fragment thereof comprises a VH CDR3 in Table 1 or Table 3. In certain embodiments, the anti-MERTK antibody or antigen-binding fragment thereof comprises a VH CDR1, a VH CDR2, and a VH CDR3 of the antibody M6 (Table 1). In certain embodiments, the anti-MERTK antibody or antigen-binding fragment thereof comprises a VH CDR1, a VH CDR2, and a VH CDR3 of the antibody M19 (Table 3).

In specific embodiments, the anti-MERTK antibody or antigen-binding fragment thereof comprises one, two, or all three of the VL CDRs above. In certain embodiments, the anti-MERTK antibody or antigen-binding fragment thereof comprises a VL CDR1 in Table 2 or Table 4. In some embodiments, the anti-MERTK antibody or antigen-binding fragment thereof comprises a VL CDR2 in Table 2 or Table 4. In certain embodiments, the anti-MERTK antibody or antigen-binding fragment thereof comprises a VL CDR3 in Table 2 or Table 4. In certain embodiments, the anti-MERTK antibody or antigen-binding fragment thereof comprises a VL CDR1, a VL CDR2, and a VL CDR3 of the antibody M6 (Table 2).

In certain embodiments, the anti-MERTK antibody or antigen-binding fragment thereof comprises a VL CDR1, a VL CDR2, and a VL CDR3 of the antibody M19 (Table 4).

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                    (SEQ ID NO: 1)
NYGMN;
and/or (b) a VH CDR2 of
                    (SEQ ID NO: 6)
WINTYTGEPTYADDFKG;
and/or (c) a VH CDR3 of
                    (SEQ ID NO: 11)
KSTVVSRYFDV;
and/or (d) a VL CDR1 of
                    (SEQ ID NO: 15)
KASQDVGDAVT;
and/or (e) a VL CDR2 of
                    (SEQ ID NO: 19)
WASTRHT;
and/or (f) a VL CDR3 of
                    (SEQ ID NO: 22)
QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                    (SEQ ID NO: 2)
GYTFTNY;
and/or (b) a VH CDR2 of
                    (SEQ ID NO: 7)
;
and/or (c) a VH CDR3 of
                    (SEQ ID NO: 12)
STVVSRYFD;
and/or (d) a VL CDR1 of
                    (SEQ ID NO: 16)
SQDVGDA;
and/or (e) a VL CDR2 of
                    (SEQ ID NO: 20)
WAS;
and/or (f) a VL CDR3 of
                    (SEQ ID NO: 23)
YRSYPL.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                    (SEQ ID NO: 3)
GYTFTNYGMN;
and/or (b) a VH CDR2 of
                    (SEQ ID NO: 8)
WINTYTGEPT;
and/or (c) a VH CDR3 of
                    (SEQ ID NO: 11)
KSTVVSRYFDV;
and/or (d) a VL CDR1 of
                    (SEQ ID NO: 15)
KASQDVGDAVT;
and/or -continued (e) a VL CDR2 of
                   (SEQ ID NO: 19)
    WASTRHT;
    and/or (f) a VL CDR3 of
                   (SEQ ID NO: 22)
    QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                   (SEQ ID NO: 4)
    TNYGMN;
    and/or (b) a VH CDR2 of
                   (SEQ ID NO: 9)
    WMGWINTYTGEPT;
    and/or (c) a VH CDR3 of
                   (SEQ ID NO: 13)
    ARKSTVVSRYFD;
    and/or (d) a VL CDR1 of
                   (SEQ ID NO: 17)
    GDAVTWC;
    and/or (e) a VL CDR2 of
                   (SEQ ID NO: 21)
    LLIYWASTRH;
    and/or (f) a VL CDR3 of
                   (SEQ ID NO: 24)
    QQYRSYPL.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                   (SEQ ID NO: 5)
    GYTFTNYG;
    and/or (b) a VH CDR2 of
                   (SEQ ID NO: 10)
    INTYTGEP;
    and/or (c) a VH CDR3 of
                   (SEQ ID NO: 14)
    ARKSTVVSRYFDV;
    and/or (d) a VL CDR1 of
                   (SEQ ID NO: 18)
    QDVGDA;
    and/or (e) a VL CDR2 comprising, of
                   (SEQ ID NO: 20)
    WAS;
    and/or (f) a VL CDR3 of
                   (SEQ ID NO: 22)
    QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                   (SEQ ID NO: 3)
    GYTFTNYGMN;
    and/or (b) a VH CDR2 of
                   (SEQ ID NO: 6)
    WINTYTGEPTYADDFKG;
    and/or (c) a VH CDR3 of
                   (SEQ ID NO: 11)
    KSTVVSRYFDV;
    and/or (d) a VL CDR1 of
                   (SEQ ID NO: 15)
    KASQDVGDAVT;
    and/or (e) a VL CDR2 of
                   (SEQ ID NO: 19)
    WASTRHT;
    and/or (f) a VL CDR3 of
                   (SEQ ID NO: 22)
    QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                   (SEQ ID NO: 25)
    DYSMH;
    and/or (b) a VH CDR2 of
                   (SEQ ID NO: 30)
    WINTDTGEPTYADDFKG;
    and/or (c) a VH CDR3 of
                   (SEQ ID NO: 35)
    WFGAMDY;
    and/or (d) a VL CDR1 of
                   (SEQ ID NO: 39)
    KASQDVTNVVA;
    and/or (e) a VL CDR2 of
                   (SEQ ID NO: 43)
    SASYRYT;
    and/or (f) a VL CDR3 of
                   (SEQ ID NO: 46)
    QQYYRTPRT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

```
(a) a VH CDR1 of
                (SEQ ID NO: 26)
    NYTFTDY;
    and/or (b) a VH CDR2 of
                (SEQ ID NO: 31)
    TDTG;
    and/or (c) a VH CDR3 of
                (SEQ ID NO: 36)
    FGAMD;
    and/or (d) a VL CDR1 of
                (SEQ ID NO: 40)
    SQDVTNV;
    and/or (e) a VL CDR2 of
                (SEQ ID NO: 44)
    SAS;
    and/or (f) a VL CDR3 of
                (SEQ ID NO: 47)
    YYRTPR.
```

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

```
(a) a VH CDR1 of
                (SEQ ID NO: 27)
    NYTFTDYSMH;
    and/or (b) a VH CDR2 of
                (SEQ ID NO: 32)
    WINTDTGEPT;
    and/or (c) a VH CDR3 of
                (SEQ ID NO: 35)
    WFGAMDY;
    and/or (d) a VL CDR1 of
                (SEQ ID NO: 39)
    KASQDVTNVVA;
    and/or (e) a VL CDR2 of
                (SEQ ID NO: 43)
    SASYRYT;
    and/or (f) a VL CDR3 of
                (SEQ ID NO: 46)
    QQYYRTPRT.
```

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

```
(a) a VH CDR1 of
                (SEQ ID NO: 28)
    TDYSMH;
    and/or (b) a VH CDR2 of
                (SEQ ID NO: 33)
    WVGWINTDTGEPT;
    and/or (c) a VH CDR3 of
                (SEQ ID NO: 37)
    ARWFGAMD;
    and/or (d) a VL CDR1 of
                (SEQ ID NO: 41)
    TNWAWY;
    and/or (e) a VL CDR2 of
                (SEQ ID NO: 45)
    LLIYSASYRY;
    and/or (f) a VL CDR3 of
                (SEQ ID NO: 48)
    QQYYRTPR.
```

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

```
(a) a VH CDR1 of
                (SEQ ID NO: 29)
    NYTFTDYS;
    and/or (b) a VH CDR2 of
                (SEQ ID NO: 34)
    INTDTGEP;
    and/or (c) a VH CDR3 of
                (SEQ ID NO: 38)
    ARWFGAMDY;
    and/or (d) a VL CDR1 of
                (SEQ ID NO: 42)
    QDVTNV;
    and/or (e) a VL CDR2 of
                (SEQ ID NO: 44)
    SAS;
    and/or (f) a VL CDR3 of
                (SEQ ID NO: 46)
    QQYYRTPRT.
```

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
                (SEQ ID NO: 27)
NYTFTDYSMH;
and/or (b) a VH CDR2 of
                (SEQ ID NO: 30)
WINTDTGEPTYADDFKG;
and/or (c) a VH CDR3 of
                (SEQ ID NO: 35)
WFGAMDY;
and/or (d) a VL CDR1 of
                (SEQ ID NO: 39)
KASQDVTNVVA;
and/or (e) a VL CDR2 of
                (SEQ ID NO: 43)
SASYRYT;
and/or (f) a VL CDR3 of
                (SEQ ID NO: 46)
QQYYRTPRT.

In a specific embodiment, an anti-MERTK antibody or antigen-binding fragment thereof that specifically binds to MERTK (e.g., human MERTK, or both human and mouse MERTK) and agonizes MERTK signaling of endothelial cells comprises a heavy chain variable region sequence comprising the amino acid sequence of SEQ ID NO: 49. In another specific embodiment, an anti-MERTK antibody or antigen-binding fragment thereof that specifically binds to MERTK (e.g., human MERTK, or both human and mouse MERTK) and agonizes MERTK signaling of endothelial cells comprises a heavy chain variable region sequence comprising the amino acid sequence of SEQ ID NO: 51.

In another embodiment, an anti-MERTK antibody or antigen-binding fragment thereof that specifically binds to MERTK (e.g., human MERTK, or both human and mouse MERTK) and agonizes MERTK signaling of endothelial cells comprises a light chain variable region sequence comprising the amino acid sequence of SEQ ID NO: 50. In another specific embodiment, an anti-MERTK antibody or antigen-binding fragment thereof that specifically binds to MERTK (e.g., human MERTK, or both human and mouse MERTK) and agonizes MERTK signaling of endothelial cells comprises a light chain variable region sequence comprising the amino acid sequence of SEQ ID NO: 52.

In another embodiment, an anti-MERTK antibody or antigen-binding fragment thereof that specifically binds to MERTK (e.g., human MERTK, or both human and mouse MERTK) and agonizes MERTK signaling of endothelial cells comprises (a) a heavy chain variable region comprising the amino acid sequence of SEQ ID NO: 49; and (b) a light chain variable region comprising the amino acid sequence of SEQ ID NO: 50. In another specific embodiment, an antibody or fragment thereof that specifically binds to MERTK (e.g., human MERTK, or both human and mouse MERTK) and agonizes MERTK signaling of endothelial cells comprises (a) a heavy chain variable region comprising the amino acid sequence of SEQ ID NO: 51; and (b) a light chain variable region comprising the amino acid sequence of SEQ ID NO: 52.

In certain embodiments, an antibody described herein, which specifically binds to MERTK (e.g., human MERTK, or both human and mouse MERTK) and agonizes MERTK signaling of endothelial cells, comprises heavy and/or light chain constant regions. In some embodiments, the heavy chain constant region is selected from the group of human immunoglobulins consisting of $IgG_1$, $IgG_2$, $IgG_3$, $IgG_4$, $IgA_1$, and $IgA_2$. In certain embodiments, the light chain constant region is selected from the group of human immunoglobulins consisting of IgGκ and IgGλ. In some embodiments, the antibody comprises a constant region having increased binding affinity to one or more human Fc gamma receptor(s). In some embodiments, the antibody comprises a constant region having decreased binding affinity to one or more human Fc gamma receptor(s).

In another embodiment, an anti-MERTK antibody or antigen-binding fragment thereof that specifically binds to MERTK (e.g., human MERTK, or both human and mouse MERTK) and agonizes MERTK signaling of endothelial cells is an anti-MERTK antibody or antigen-binding fragment thereof that binds to the same epitope of MERTK (e.g., human MERTK, or both human and mouse MERTK) as the antibody described herein. In another embodiment, an anti-MERTK antibody or antigen-binding fragment thereof that specifically binds to MERTK (e.g., human MERTK, or both human and mouse MERTK) and agonizes MERTK signaling of endothelial cells is an anti-MERTK antibody or antigen-binding fragment thereof that competes with an anti-MERTK antibody or an antigen-binding fragment thereof described herein for binding to MERTK (e.g., human MERTK, or both human and mouse MERTK). In another specific embodiment, an anti-MERTK antibody or antigen-binding fragment thereof that specifically binds to MERTK (e.g., human MERTK, or both human and mouse MERTK) and agonizes MERTK signaling of endothelial cells is a first anti-MERTK antibody or antigen-binding fragment thereof that competes with an anti-MERTK antibody or an antigen-binding fragment thereof described herein for binding to MERTK (e.g., human MERTK, or both human and mouse MERTK), wherein the competition is exhibited as reduced binding of the first anti-MERTK antibody or antigen-binding fragment thereof to MERTK (e.g., human MERTK, or both human and mouse MERTK) by more than 80% (e.g., 85%, 90%, 95%, or 98%, or between 80% to 85%, 80% to 90%, 85% to 90%, or 85% to 95%) in the presence of the anti-MERTK antibody or antigen-binding fragment thereof described herein.

In specific embodiments, an antibody described herein, which specifically binds to MERTK (e.g., human MERTK, or both human and mouse MERTK) and agonizes MERTK signaling of endothelial cells is a human antibody, humanized antibody, murine antibody or chimeric antibody. In certain embodiments, an antibody described herein, which specifically binds to MERTK (e.g., human MERTK, or both human and mouse MERTK) and agonizes MERTK signaling of endothelial cells binds to MERTK (e.g., human MERTK, or both human and mouse MERTK) with a $K_D$ in the range of about 3 pM to 400 pM. In specific embodiments, an antibody described herein is isolated. In specific embodiments, an antibody described herein is a monoclonal antibody.

In another embodiment, described herein are nucleic acid molecules encoding a heavy chain variable region and/or a light chain variable region, or a heavy chain and/or a light chain of an anti-MERTK antibody described herein. In a specific embodiment, the nucleic acid molecule encodes a heavy chain variable region comprising the nucleic acid sequence of SEQ ID NO: 53 or SEQ ID NO: 55. In another specific embodiment, the nucleic acid molecule encodes a light chain variable region comprising the nucleic acid sequence of SEQ ID NO: 54 or SEQ ID NO: 56. In specific embodiments, the nucleic acid molecule is isolated.

In certain embodiments, described herein is a vector (e.g., an isolated vector) comprises a polynucleotide encoding a heavy chain variable region and/or a light chain variable region, or a heavy chain and/or a light chain of an anti-MERTK antibody described herein. In certain embodiments, described herein is a host cell that comprises the polynucleotide or vector. Examples of host cells include *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cells, plant cells, insect cells, and human cells in tissue culture. In a specific embodiment, described herein is a method of producing an anti-MERTK antibody or antigen-binding fragment thereof that specifically binds to MERTK (e.g., human MERTK, or both human and mouse MERTK) and agonizes MERTK signaling of endothelial cells comprising culturing a host cell so that the polynucleotide is expressed and the antibody is produced.

In another embodiment, provided herein are pharmaceutical compositions comprising an antibody-drug conjugate described herein, and a pharmaceutically acceptable carrier. The pharmaceutical composition can be used to treat cancer.

In certain embodiments, provided herein is a method of treating cancer in a subject, comprising administering to the subject an effective amount of an antibody-drug conjugate described herein. In another embodiment, provided herein is a method for treating cancer in a subject comprising administering to the subject a pharmaceutical composition described herein. In certain embodiments, the method of treating cancer results in inhibition of the migration of endothelial cells, inhibition of angiogenesis, and/or inhibition of tumor progression.

In certain embodiments, the cancer treated by the methods provided herein is a cancer of the lung, breast, bone, ovary, stomach, pancreas, larynx, esophagus, testes, liver, parotid, biliary tract, colon, rectum, cervix, uterus, endometrium, kidney, bladder, prostate or thyroid. In some embodiments, the cancer treated is a sarcoma, squamous cell carcinoma, melanoma, glioma, glioblastoma, neuroblastoma or Kaposi's sarcomas.

In certain embodiments, the cancer treated by the methods provided herein is breast cancer. In a specific embodiment, the cancer treated by the methods provided herein is triple-negative breast cancer.

In certain embodiments, the method of treating cancer further comprises administering to the subject an additional therapeutic agent. Examples of additional therapeutic agents that can be administered to a subject in combination with an antibody-drug conjugate described herein or a pharmaceutical composition described herein are described in Sections 5.6 and 5.7, infra.

In specific embodiments, the additional therapeutic agents administered to a subject in combination with an antibody-drug conjugate described herein is an agent used to treat breast cancer, an agent used to treat melanoma, an immunotherapy, or an angiogenesis inhibitor.

In a specific embodiment, the additional therapeutic agent is an agent used to treat breast cancer that is selected from the group consisting of Tamoxifen, Raloxifene, Paclitaxel (TAXOL®), Cyclophosphamide, Docetaxel, Vinblastine, Fluorouracil, Everolimus, Trastuzumab, Trastuzumab-Emtansine, Pertuzumab, and Lapatinib Ditosylate.

In a specific embodiment, the additional therapeutic agent is an agent used to treat melanoma that is selected from the group consisting of a BRAF inhibitor, a MEK inhibitor, and Dacarbazine.

In a specific embodiment, the additional therapeutic agent is an antibody that is a CTLA-4 inhibitor, a PD-1 inhibitor, or a PD-L1 inhibitor.

In a specific embodiment, the additional therapeutic agent is an angiogenesis inhibitor that is selected from the group consisting of a VEGF inhibitor, a VEGFR2 inhibitor, Sunitinib, and Sorafenib.

In specific embodiments, the subject treated by the methods described herein is a human.

In one aspect, provided herein is an antibody-drug conjugate comprising: (a) an antibody moiety that is an antibody or an antigen-binding fragment thereof that specifically binds to human Mer Tyrosine Kinase (MERTK), wherein the antibody agonizes human MERTK signaling of endothelial cells; (b) one or more drug moieties, each drug moiety being a cytotoxic agent; and (c) optionally a linker; wherein the cytotoxic agent is conjugated directly to the antibody moiety or is conjugated to the antibody moiety via the linker.

In a specific embodiment of the preceding aspect, the antibody or antigen-binding fragment thereof further specifically binds to murine MERTK.

In a specific embodiment of any of the preceding aspects/embodiments, the antibody specifically recognizes the extracellular domain of human MERTK, and the extracellular domain comprises the amino acid sequence of SEQ ID NO: 58.

In a specific embodiment of any of the preceding aspects/embodiments, the antibody competes with Gas-6 for binding to human MERTK.

In a specific embodiment of any of the preceding aspects/embodiments, the antibody is a monoclonal antibody.

In a specific embodiment of any of the preceding aspects/embodiments, the antibody is an immunoglobulin comprising two identical light chains and two identical heavy chains.

In a specific embodiment of the embodiment wherein the antibody is an immunoglobulin comprising two identical light chains and two identical heavy chains, each of the heavy chains comprises a variable region (VH), which comprises a complementarity determining region (CDR) 1 of SEQ ID NO: 1, a CDR2 of SEQ ID NO: 6, and a CDR3 of SEQ ID NO: 11. In one further embodiment of such a specific embodiment, each of the light chains comprises a variable region (VL), which comprises a complementarity determining region (CDR) 1 of SEQ ID NO: 15, a CDR2 of SEQ ID NO: 19, and a CDR3 of SEQ ID NO: 22.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 2, a CDR2 of SEQ ID NO: 7, and a CDR3 of SEQ ID NO: 12. In one further embodiment of such a specific embodiment, each of the light chains comprises a variable region (VL) and the VL comprises a CDR1 of SEQ ID NO: 16, a CDR2 of SEQ ID NO: 20, and a CDR3 of SEQ ID NO: 23.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 3, a CDR2 of SEQ ID NO: 8, and a CDR3 of SEQ ID NO: 11. In one further embodiment of such a specific embodiment, each of the light chains comprises a variable region (VL), which comprises a complementarity determining region (CDR) 1 of SEQ ID NO: 15, a CDR2 of SEQ ID NO: 19, and a CDR3 of SEQ ID NO: 22.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 4, a CDR2 of SEQ ID NO: 9, and a CDR3 of SEQ ID NO: 13. In one further embodiment of such a specific embodiment, each of the light chains comprises a variable region (VL) and the VL comprises a CDR1 of SEQ ID NO: 17, a CDR2 of SEQ ID NO: 21, and a CDR3 of SEQ ID NO: 24.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 5, a CDR2 of SEQ ID NO: 10, and a CDR3 of SEQ ID NO: 14. In one further embodiment of such a specific embodiment, each of the light chains comprises a variable region (VL) and the VL comprises CDR1 of SEQ ID NO: 18, a CDR2 of SEQ ID NO: 20, and a CDR3 of SEQ ID NO: 22.

In a specific embodiment of the embodiment wherein the antibody is an immunoglobulin comprising two identical light chains and two identical heavy chains, each of the heavy chains comprises a variable region (VH) and the VH comprises CDR1 of SEQ ID NO: 3, a CDR2 of SEQ ID NO: 6, and a CDR3 of SEQ ID NO: 11. In one further embodiment of such a specific embodiment, each of the light chains comprises a variable region (VL), which comprises a complementarity determining region (CDR) 1 of SEQ ID NO: 15, a CDR2 of SEQ ID NO: 19, and a CDR3 of SEQ ID NO: 22.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 25, a CDR2 of SEQ ID NO: 30, and a CDR3 of SEQ ID NO: 35. In one further embodiment of such a specific embodiment, each of the light chains comprises a variable region (VL) and the VL comprises a CDR1 of SEQ ID NO: 39, a CDR2 of SEQ ID NO: 43, and a CDR3 of SEQ ID NO: 46.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 26, a CDR2 of SEQ ID NO: 31, and a CDR3 of SEQ ID NO: 36. In one further embodiment of such a specific embodiment, each of the light chains comprises a variable region (VL) and the VL comprises a CDR1 of SEQ ID NO: 40, a CDR2 of SEQ ID NO: 44, and a CDR3 of SEQ ID NO: 47.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 27, a CDR2 of SEQ ID NO: 32, and a CDR3 of SEQ ID NO: 35. In one further embodiment of such a specific embodiment, each of the light chains comprises a variable region (VL) and the VL comprises a CDR1 of SEQ ID NO: 39, a CDR2 of SEQ ID NO: 43, and a CDR3 of SEQ ID NO: 46.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 28, a CDR2 of SEQ ID NO: 33, and a CDR3 of SEQ ID NO: 37. In one further embodiment of such a specific embodiment, each of the light chains comprises a variable region (VL) and the VL comprises a CDR1 of SEQ ID NO: 41, a CDR2 of SEQ ID NO: 45, and a CDR3 of SEQ ID NO: 48.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 29, a CDR2 of SEQ ID NO: 34, and a CDR3 of SEQ ID NO: 38.

In a specific embodiment of the embodiment wherein the antibody is an immunoglobulin comprising two identical light chains and two identical heavy chains, each of the heavy chains comprises a variable region (VH) and the VH comprises a CDR1 of SEQ ID NO: 27, a CDR2 of SEQ ID NO: 30, and a CDR3 of SEQ ID NO: 35. In one further embodiment of such a specific embodiment, each of the light chains comprises a variable region (VL) and the VL comprises a CDR1 of SEQ ID NO: 39, a CDR2 of SEQ ID NO: 43, and a CDR3 of SEQ ID NO: 46. In another further embodiment of such a specific embodiment, each of the light chains comprises a variable region (VL) and the VL comprises a CDR1 of SEQ ID NO: 42, a CDR2 of SEQ ID NO: 44, and a CDR3 of SEQ ID NO: 46.

In a specific embodiment of the embodiment wherein the antibody is an immunoglobulin comprising two identical light chains and two identical heavy chains, each of the light chains comprises a variable region (VL), which comprises a complementarity determining region (CDR) 1 of SEQ ID NO: 15, a CDR2 of SEQ ID NO: 19, and a CDR3 of SEQ ID NO: 22.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 16, a CDR2 of SEQ ID NO: 20, and a CDR3 of SEQ ID NO: 23.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 17, a CDR2 of SEQ ID NO: 21, and a CDR3 of SEQ ID NO: 24.

In a specific embodiment of the embodiment wherein the antibody is an immunoglobulin comprising two identical light chains and two identical heavy chains, each of the light chains comprises a variable region (VL) and the VL comprises CDR1 of SEQ ID NO: 18, a CDR2 of SEQ ID NO: 20, and a CDR3 of SEQ ID NO: 22.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 39, a CDR2 of SEQ ID NO: 43, and a CDR3 of SEQ ID NO: 46.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 40, a CDR2 of SEQ ID NO: 44, and a CDR3 of SEQ ID NO: 47.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 41, a CDR2 of SEQ ID NO: 45, and a CDR3 of SEQ ID NO: 48.

In a specific embodiment of the embodiment wherein the antibody is an immunoglobulin comprising two identical light chains and two identical heavy chains, each of the light chains comprises a variable region (VL) and the VL comprises a CDR1 of SEQ ID NO: 42, a CDR2 of SEQ ID NO: 44, and a CDR3 of SEQ ID NO: 46.

In a specific embodiment of the embodiment wherein the antibody is an immunoglobulin comprising two identical light chains and two identical heavy chains, the heavy chain comprises a variable region (VH), which comprises SEQ ID NO: 49. In one further embodiment of such a specific embodiment, the light chain comprises a variable region (VL), which comprises SEQ ID NO: 50.

In a specific embodiment of the embodiment wherein the antibody is an immunoglobulin comprising two identical light chains and two identical heavy chains, the light chain comprises a variable region (VL), which comprises SEQ ID NO: 50.

In a specific embodiment of the embodiment wherein the antibody is an immunoglobulin comprising two identical light chains and two identical heavy chains, the heavy chain comprises a variable region (VH), which comprises SEQ ID NO: 51. In one further embodiment of such a specific embodiment, the light chain comprises a variable region (VL), which comprises SEQ ID NO: 52.

In a specific embodiment of the embodiment wherein the antibody is an immunoglobulin comprising two identical light chains and two identical heavy chains, the light chain comprises a variable region (VL), which comprises SEQ ID NO: 52.

In a specific embodiment of any of the preceding embodiments, wherein the antibody is an immunoglobulin comprising two identical light chains and two identical heavy chains, the antibody or antigen-binding fragment thereof comprises a human-derived constant region. In one further embodiment of such a specific embodiment, the heavy chain constant region has an isotype selected from the group consisting of gamma1, gamma2, gamma3, and gamma4.

In a specific embodiment of any of the preceding aspects/embodiments, the antibody or antigen-binding fragment thereof is humanized.

In a specific embodiment of any of the preceding aspects/embodiments, the antibody binds human MERTK with a dissociation constant ($K_D$) in the range of about 3 picomolar (pM) to 400 pM.

In a specific embodiment of any of the preceding aspects/embodiments, the antibody binds murine MERTK with a $K_D$ in the range of about 3 pM to 400 pM.

In a specific embodiment of any of the preceding aspects/embodiments, the antibody or antigen-binding fragment inhibits the migration of endothelial cells in vitro in the presence of breast cancer cells, wherein the migration is inhibited by more than 30% as compared to endothelial cells treated with a control antibody.

In a specific embodiment of any of the preceding aspects/embodiments, the antibody or antigen-binding fragment promotes the phosphorylation of MERTK of human vascular endothelial cells in vitro.

In a specific embodiment of any of the preceding aspects/embodiments, the antibody or antigen-binding fragment does not promote the phosphorylation of MERTK on cancer cells in vitro.

In a specific embodiment of any of the preceding aspects/embodiments, the antibody or antigen-binding fragment inhibits tumor angiogenesis in vivo.

In a specific embodiment of any of the preceding aspects/embodiments, the antibody or antigen-binding fragment does not inhibit the migration of glioblastoma multiforme cell line A172 in an in vitro trans-well migration assay in the absence of endothelial cells.

In a specific embodiment of any of the preceding aspects/embodiments, the antibody or antigen-binding fragment does not decrease the expression level of MERTK on the glioblastoma multiforme cell line A172.

In another aspect, provided herein is an antibody-drug conjugate comprising: (a) an antibody moiety that is an antibody or antigen-binding fragment thereof that specifically binds to human MERTK, the antibody or antigen-binding fragment comprising a heavy chain variable region (VH), wherein the VH comprises a complementarity determining region (CDR) 1 of SEQ ID NO: 1, a VH CDR2 of SEQ ID NO: 6, and a VH CDR3 of SEQ ID NO: 11; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a complementarity determining region (CDR) 1 of SEQ ID NO: 15, a CDR2 comprising the amino acid sequence of SEQ ID NO: 19, and a CDR3 comprising the amino acid sequence of SEQ ID NO: 22.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 2, a CDR2 of SEQ ID NO: 7, and a CDR3 of SEQ ID NO: 12; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 16, a CDR2 of SEQ ID NO: 20, and a CDR3 of SEQ ID NO: 23.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 3, a CDR2 of SEQ ID NO: 8, and a CDR3 of SEQ ID NO: 11; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a complementarity determining region (CDR) 1 of SEQ ID NO: 15, a CDR2 comprising the amino acid sequence of SEQ ID NO: 19, and a CDR3 comprising the amino acid sequence of SEQ ID NO: 22.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 4, a CDR2 of SEQ ID NO: 9, and a CDR3 of SEQ ID NO: 13; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 17, a CDR2 of SEQ ID NO: 21, and a CDR3 of SEQ ID NO: 24.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 5, a CDR2 of SEQ ID NO: 10, and a CDR3 of SEQ ID NO: 14; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises CDR1 of SEQ ID NO: 18, a CDR2 of SEQ ID NO: 20, and a CDR3 of SEQ ID NO: 22.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises CDR1 of SEQ ID NO: 3, a CDR2 of SEQ ID NO: 6, and a CDR3 of SEQ ID NO: 11; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a complementarity determining region (CDR) 1 of SEQ ID NO: 15, a CDR2 comprising the amino acid sequence of SEQ ID NO: 19, and a CDR3 comprising the amino acid sequence of SEQ ID NO: 22.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 25, a CDR2 of SEQ ID NO: 30, and a CDR3 of SEQ ID NO: 35; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 39, a CDR2 of SEQ ID NO: 43, and a CDR3 of SEQ ID NO: 46.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 26, a CDR2 of SEQ ID NO: 31, and a CDR3 of SEQ ID NO: 36; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 40, a CDR2 of SEQ ID NO: 44, and a CDR3 of SEQ ID NO: 47.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 27, a CDR2 of SEQ ID NO: 32, and a CDR3 of SEQ ID NO: 35; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 39, a CDR2 of SEQ ID NO: 43, and a CDR3 of SEQ ID NO: 46.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 28, a CDR2 of SEQ ID NO: 33, and a CDR3 of SEQ ID NO: 37; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 41, a CDR2 of SEQ ID NO: 45, and a CDR3 of SEQ ID NO: 48.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 29, a CDR2 of SEQ ID NO: 34, and a CDR3 of SEQ ID NO: 38; (b) one or more drug moieties, each drug moiety being a cytotoxic agent; and (c) optionally a linker; wherein the cytotoxic agent is conjugated directly to the antibody moiety or is conjugated to the antibody moiety via the linker.

In another aspect, provided herein is an antibody-drug conjugate comprising: (a) an antibody moiety that is an antibody or antigen-binding fragment thereof of that specifically binds to human MERTK, the antibody or antigen-binding fragment comprising a heavy chain variable region (VH), wherein the VH comprises a CDR1 of SEQ ID NO: 27, a CDR2 of SEQ ID NO: 30, and a CDR3 of SEQ ID NO: 35; (b) one or more drug moieties, each drug moiety being a cytotoxic agent; and (c) optionally a linker; wherein the cytotoxic agent is conjugated directly to the antibody moiety or is conjugated to the antibody moiety via the linker. In a specific embodiment of such an aspect, the antibody or antigen-binding fragment thereof of further comprises a light chain variable region (VL), wherein the VL comprises a CDR1 of SEQ ID NO: 39, a CDR2 of SEQ ID NO: 43, and a CDR3 of SEQ ID NO: 46. In another specific embodiment of such an aspect, the antibody or antigen-binding fragment thereof of further comprises a light chain variable region (VL), wherein the VL comprises a CDR1 of SEQ ID NO: 42, a CDR2 of SEQ ID NO: 44, and a CDR3 of SEQ ID NO: 46.

In a specific embodiment of any of the preceding aspects, the antibody is an immunoglobulin, and the antigen-binding fragment is a portion of an immunoglobulin.

In a specific embodiment of any of the preceding aspects, the antibody or antigen-binding fragment thereof is an immunoglobulin.

In a specific embodiment of any of the preceding aspects/embodiments, the antibody or antigen-binding fragment thereof is humanized.

In a specific embodiment of any of the preceding aspects/embodiments, the antibody or antigen-binding fragment thereof comprises a human-derived constant region. In one further embodiment of such a specific embodiment, the antibody or antigen-binding fragment thereof is a humanized immunoglobulin.

In a specific embodiment of any of the preceding aspects/embodiments, wherein the antibody is not a monoclonal antibody or an immunoglobulin comprising two identical light chains and two identical heavy chains, the antibody or antigen-binding fragment thereof is a bispecific antibody.

In another aspect, provided herein is an antibody-drug conjugate comprising: (A) an antibody moiety that is an immunoglobulin that specifically binds to human MERTK, the immunoglobulin comprising (i) a heavy chain variable region that comprises the amino acid sequence of SEQ ID NO: 51, and (ii) a light chain variable region that comprises the amino acid sequence of SEQ ID NO: 52; (B) one or more drug moieties, each drug moiety being a cytotoxic agent; and (C) optionally a linker; wherein the cytotoxic agent is conjugated directly to the antibody moiety or is conjugated to the antibody moiety via the linker.

In another aspect, provided herein is an antibody-drug conjugate comprising: (A) an antibody moiety that is an immunoglobulin that specifically binds to human MERTK, the immunoglobulin comprising (i) a heavy chain variable region that comprises the amino acid sequence of SEQ ID NO: 49, and (ii) a light chain variable region that comprises the amino acid sequence of SEQ ID NO: 50; (B) one or more drug moieties, each drug moiety being a cytotoxic agent; and (C) optionally a linker; wherein the cytotoxic agent is conjugated directly to the antibody moiety or is conjugated to the antibody moiety via the linker.

In another aspect, provided herein is an antibody drug conjugate comprising:
(I) an antibody moiety that is an immunoglobulin that specifically binds to human MERTK, the immunoglobulin comprising:
 (A) (i) a heavy chain variable region that comprises the amino acid sequence of SEQ ID NO: 51, and (ii) a light chain variable region that comprises the amino acid sequence of SEQ ID NO: 52; or
 (B) (i) a heavy chain variable region that comprises the amino acid sequence of SEQ ID NO: 49, and (ii) a light chain variable region that comprises the amino acid sequence of SEQ ID NO: 50;
(II) one or more drug moieties, each drug moiety being a cytotoxic agent; and
(III) optionally a linker;
wherein the cytotoxic agent is conjugated directly to the antibody moiety or is conjugated to the antibody moiety via the linker.

In another aspect, provided herein is an antibody-drug conjugate comprising:
(I) an antibody moiety that is an antibody which competes for binding to MERTK with a reference antibody selected from the group consisting of:
 (A) a first immunoglobulin comprising (i) a heavy chain variable region that comprises the amino acid sequence of SEQ ID NO: 51, and (ii) a light chain variable region that comprises the amino acid sequence of SEQ ID NO: 52; and
 (B) a second immunoglobulin comprising (i) a heavy chain variable region that comprises the amino acid sequence of SEQ ID NO: 49, and (ii) a light chain variable region that comprises the amino acid sequence of SEQ ID NO: 50;
(II) one or more drug moieties, each drug moiety being a cytotoxic agent; and
(III) optionally a linker;
wherein the cytotoxic agent is conjugated directly to the antibody moiety or is conjugated to the antibody moiety via the linker.

In a specific embodiment of any of the preceding aspects/embodiments, the molar ratio of the antibody moiety to the drug moiety is between 1:1 and 1:8.

In a specific embodiment of any of the preceding aspects/embodiments, the molar ratio of the antibody moiety to the drug moiety is between 1:3 and 1:5.

In a specific embodiment of any of the preceding aspects/embodiments, the antibody-drug conjugate comprises the linker and the linker is a cleavable linker.

In a specific embodiment of any of the preceding aspects/embodiments, the antibody-drug conjugate comprises the linker and the linker is a non-cleavable linker.

In a specific embodiment of any of the preceding aspects/embodiments, the cytotoxic agent is a small molecule, a nucleotide, a peptide, or a non-antibody protein. In one further embodiment of such a specific embodiment, the cytotoxic agent is a small molecule.

In a specific embodiment of any of the preceding aspects/embodiments, the cytotoxic agent is an auristatin, a maytansinoid, a pyrrolobenzodiazepine, an indolinobenzodiazepine, a calicheamicin, a camptothecin analogue, a duocarmycin, a tubulin inhibitor, a tubulysin or tubulysin analogue, amberstatin269, doxorubicin, an antibiotic, an anthracycline, a microtubule inhibitor, a spliceostatin, or a thailanstatin. In one further embodiment of such a specific embodiment, the cytotoxic agent is monomethyl auristatin E (MMAE) or monomethyl auristatin F (MMAF). In another further embodiment of such a specific embodiment, the cytotoxic agent is DM1 or DM4.

In another aspect, provided herein is a method of producing an antibody-drug conjugate described in any of the preceding aspects/embodiments wherein the linker is not present, the method comprising: (a) conjugating the cytotoxic agent directly to the antibody moiety to produce the antibody-drug conjugate; and (b) purifying the antibody-drug conjugate.

In another aspect, provided herein is a method of producing an antibody-drug conjugate described in any of the preceding aspects/embodiments wherein the antibody-drug conjugate comprises the linker, the method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

In another aspect, provided herein is a method of producing an antibody-drug conjugate described in any of the preceding aspects/embodiments wherein the antibody-drug conjugate comprises the linker, the method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate after (b).

In another aspect, provided herein is a pharmaceutical composition comprising a therapeutically effective amount of the antibody-drug conjugate described in any of the preceding aspects/embodiments; and a pharmaceutically acceptable carrier.

In another aspect, provided herein is a method of treating cancer in a subject in need thereof, comprising administering to the subject the pharmaceutical composition described in the preceding aspect.

In a specific embodiment of the preceding aspect of a method of treating cancer, the cancer is a cancer of the lung, breast, bone, ovary, stomach, pancreas, larynx, esophagus, testes, liver, parotid, biliary tract, colon, rectum, cervix, uterus, endometrium, kidney, bladder, prostate or thyroid. In a certain embodiment of such a specific embodiment, the cancer is breast cancer. In a further embodiment of such a certain embodiment, the cancer is triple-negative breast cancer.

In a specific embodiment of the preceding aspect of a method of treating cancer, the cancer is a sarcoma, squamous cell carcinoma, melanoma, glioma, glioblastoma, neuroblastoma or Kaposi's sarcomas.

In a specific embodiment of any of the preceding aspects/embodiments of a method of treating cancer, the method further comprises administering to the subject an additional therapeutic agent.

In a specific embodiment of the embodiment wherein the method further comprises administering to the subject an additional therapeutic agent, the additional therapeutic agent is for treating the cancer.

In a specific embodiment of the embodiment wherein the additional therapeutic agent is for treating the cancer, the additional therapeutic agent is an agent used to treat breast cancer, an agent used to treat melanoma, an immunotherapy, or an angiogenesis inhibitor. In one further embodiment of such a specific embodiment, the additional therapeutic agent is an agent used to treat breast cancer that is selected from the group consisting of Tamoxifen, Raloxifene, Paclitaxel, Cyclophosphamide, Docetaxel, Vinblastine, Fluorouracil, Everolimus, Trastuzumab, Trastuzumab-Emtansine, Pertuzumab, and Lapatinib Ditosylate. In another further embodiment of such a specific embodiment, the additional therapeutic agent is an agent used to treat melanoma that is selected from the group consisting of a BRAF inhibitor, a MEK inhibitor, and Dacarbazine. In another further embodiment of such a specific embodiment, the additional therapeutic agent is an antibody that is a CTLA-4 inhibitor, a PD-1 inhibitor, or a PD-L1 inhibitor. In another further embodiment of such a specific embodiment, the additional therapeutic agent is an angiogenesis inhibitor that is selected from the group consisting of a VEGF inhibitor, a VEGFR2 inhibitor, Sunitinib, and Sorafenib.

In a specific embodiment of any of the preceding aspects/embodiments of a method of treating cancer, the subject is a human.

4. BRIEF DESCRIPTIONS OF FIGURES

FIGS. 1A and 1B: MERTK sequences. A) A schematic of the recombinant MERTK peptide used to immunize mice for the production of antibodies. The peptide consists of the extracellular domain of MERTK (See FIG. 1B), a short linking peptide (IEGRMD), and a portion of human $IgG_1$. B) The sequence of full-length human MERTK (SEQ ID NO: 57) indicating the portion of MERTK used in the recombinant MERTK peptide described in FIG. 1A (bold and underlined sequence; SEQ ID NO: 58).

FIG. 2: MERTK monoclonal antibody screen. A diagram showing data from antibody capture ELISA assays used to characterize binding properties of MERTK-binding monoclonal antibodies recovered from single hybridoma clones. Antibody clones are arbitrarily designated M1 through M20 in the first column. Several of the MERTK binding monoclonal antibodies demonstrated high affinity binding to MERTK, as indicated by large (>3.5) O.D. values in the second column. Some of these antibodies also neutralized binding of MERTK to Gas-6, as indicated by a low (<2.5) blocking O.D. value in the third column.

FIG. 3: MERTK binding antibodies M19 and M6 inhibit endothelial recruitment. A diagram showing that physiological concentrations of either monoclonal antibody M6 or M19 is capable of significantly inhibiting endothelial recruitment by metastatic breast cancer cells. $2.5 \times 10^4$ MDA-MB-231 cells were seeded in quadruplicate. Trans-well migration of $5 \times 10^4$ HUVEC cells towards the cancer cells was assessed in the presence of 200 ng/mL control antibody (IgG) or MERTK binding antibodies isolated from the screen. Images of cells that migrated through the trans-well inserts were obtained and cells counted using ImageJ software. N=4. Monoclonal antibodies that significantly inhibit endothelial cell recruitment (M6 and M19) are labeled in red and green respectively. Error bars represent standard error of the mean.

Figures 4A, 4B, 4C:
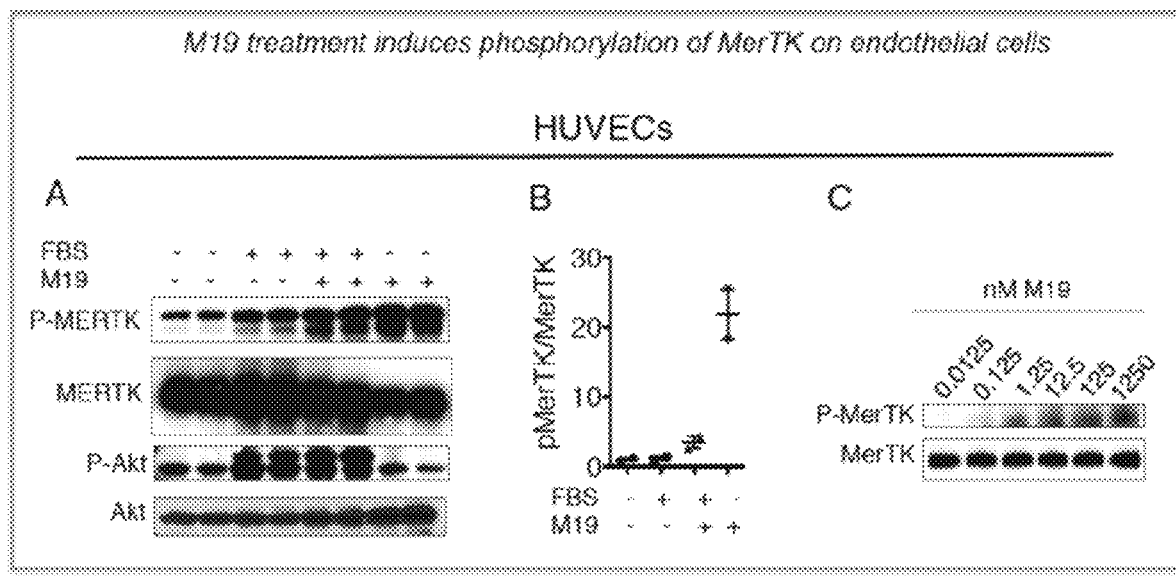

FIGS. 4A, 4B and 4C: MERTK-binding antibody M19 activates MERTK on endothelial cells. A) HUVEC cells were treated with either no FBS+no M19, 10% FBS+no M19, 10% FBS+25 µg/mL of M19, or no FBS+25 µg/mL of M19 for 16 hours prior to western blot analysis of activated (phosphorylated) MERTK (P-MERTK) and total levels of MERTK and AKT. As shown, treatment with M19 antibody increased levels of activated MERTK. B) Quantification of MERTK activation with M19 antibody treatment, calculated as a ratio of the protein expression levels of P-MERTK to MERTK, isolated from M19 treated and untreated HUVEC cells from the western blot data from FIG. 4A. C) HUVEC cells were treated with increasing concentrations of M19 antibody as indicated for 30 minutes prior to western blot analysis of P-MERTK. Note that increasing activation of MERTK was seen with increasing doses of M19 treatment.

Figures 5A, 5B:
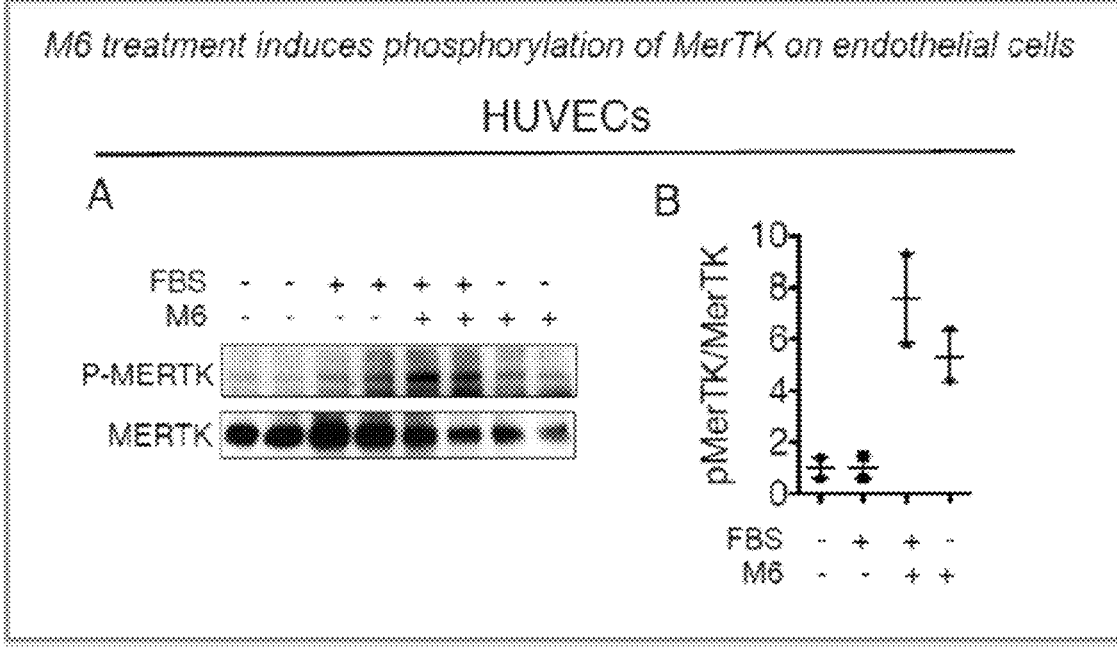

FIGS. 5A and 5B: MERTK binding antibody M6 activates MERTK on endothelial cells. A) HUVEC cells were treated with either no FBS+no M6, 10% FBS+no M6, 10% FBS+25 µg/mL of M6, or no FBS+25 µg/mL of M6 for 16 hours prior to western blot analysis of activated (phosphorylated) MERTK (P-MERTK) and total levels of MERTK. As shown, treatment with M6 antibody increased levels of activated MERTK. B) Quantification of MERTK activation with M6 antibody treatment, calculated as a ratio of the protein expression levels of P-MERTK to MERTK, isolated from M6 treated and untreated HUVEC cells from the western blot data from FIG. 5A.

Figure 6:
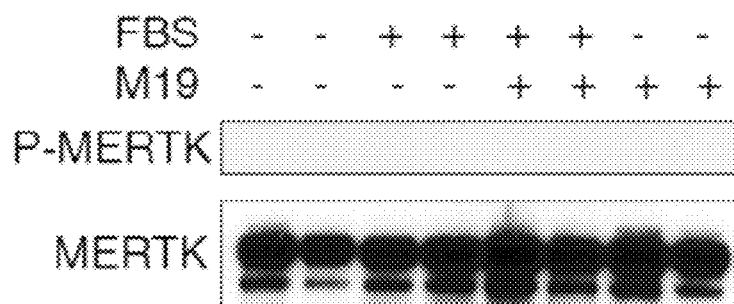

FIG. 6: MERTK binding antibody M19 does not activate MERTK on cancer cells. LM2 breast cancer cells were treated with either no FBS+no M19 antibody, 10% FBS+no M19 antibody, 10% FBS+25 µg/mL M19 antibody or no FBS+25 µg/mL M19 antibody for 16 hours prior to western blot analysis of activated MERTK (P-MERTK) and total levels of MERTK. As shown, no detectable levels of P-MERTK were induced in cancer cells treated with M19 antibody.

FIG. 7: M19 binds to human MERTK with high affinity. A diagram showing antibody binding kinetics for M19 (Mer-M19) against human MERTK (hMer) using biolayer interferometry. Purified M19 was loaded on an AMQ sensor at a concentration of 1 microgram/mL to test binding against analytes in solution. All analytes were prepared at 5 nM with a 2-fold dilution series for a total of 7 concentrations. Kinetic fits were calculated using a 1:1 model, with Local fits for each concentration as well as an overall global fit. The overall global fit calculated binding affinity ($K_D$) for M19 binding to human MERTK was 326 picomolar.

FIG. 8: M19 binds to murine MERTK with high affinity. A diagram showing antibody binding kinetics for M19 (Mer-M19) against murine MERTK (msMer) using biolayer interferometry. Purified M19 was loaded on an AMQ sensor at a concentration of 1 microgram/mL to test binding against analytes in solution. All analytes were prepared at 5 nM with a 2-fold dilution series for a total of 7 concentrations. Kinetic fits were calculated using a 1:1 model, with Local fits for each concentration as well as an overall Global fit. The overall calculated global fit binding affinity ($K_D$) for M19 binding to mouse MERTK was 305 picomolar.

Figures 9A, 9B:
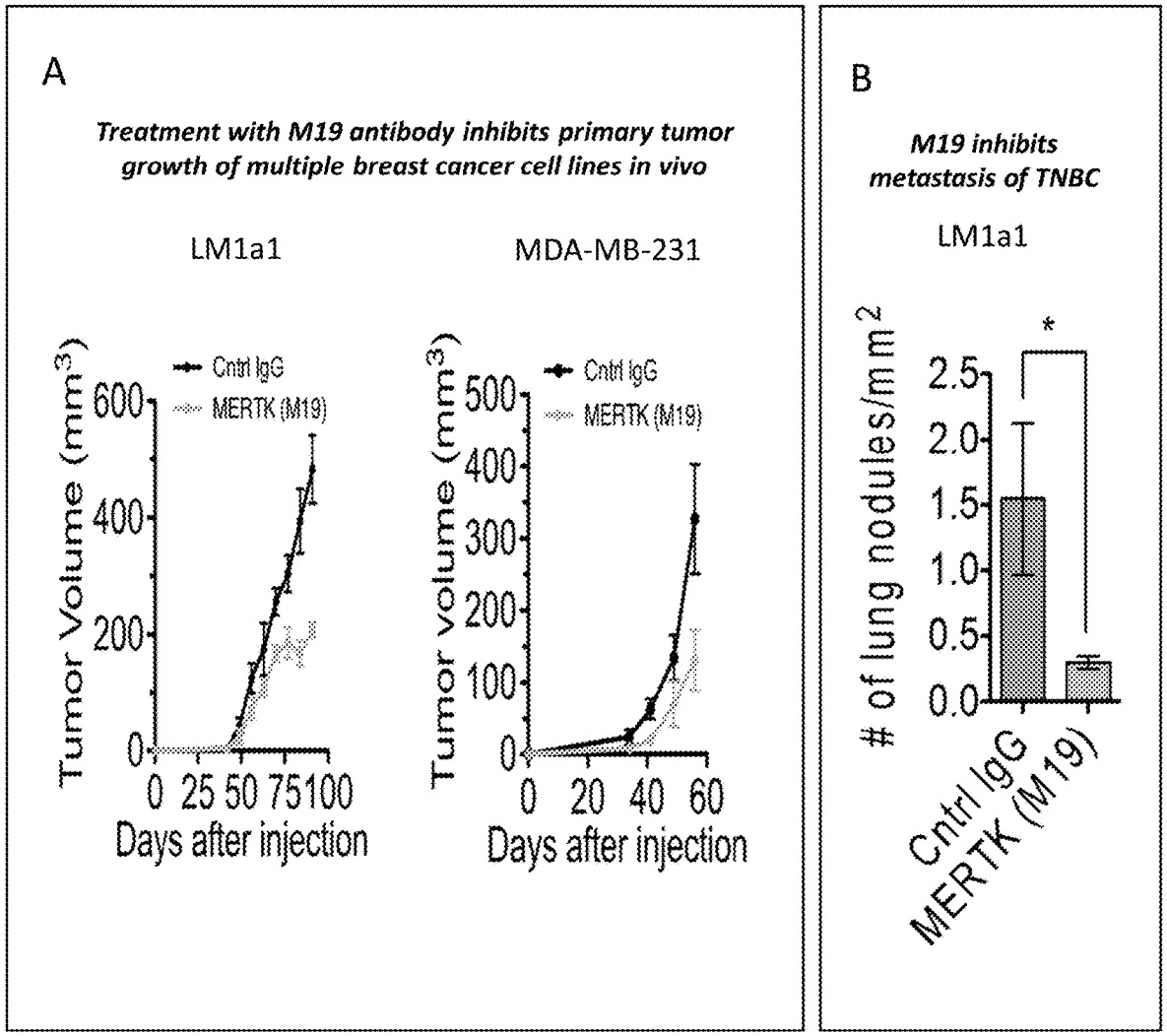

FIGS. 9A and 9B: Treatment with M19 inhibits primary tumor growth and metastasis of triple-negative breast cancer in vivo. A) Mammary fat pad tumor growth of 2000 MDA-MB-231 or 5000 Lm1a1 breast cancer cells in mice treated biweekly with 250 µg of either control antibody (IgG) or M19 antibody. B) Lm1a1 breast cancer cells were injected bilaterally in the mammary fat pad in mice treated biweekly with 250 µg of either control antibody (IgG) or M19 antibody. After 98 days the lungs were removed, processed for H&E staining, and the number of metastatic nodules were counted. N=4. Error bars represent standard error of the mean. P-values were obtained using student's T-test (*p<0.05)

Figure 10:
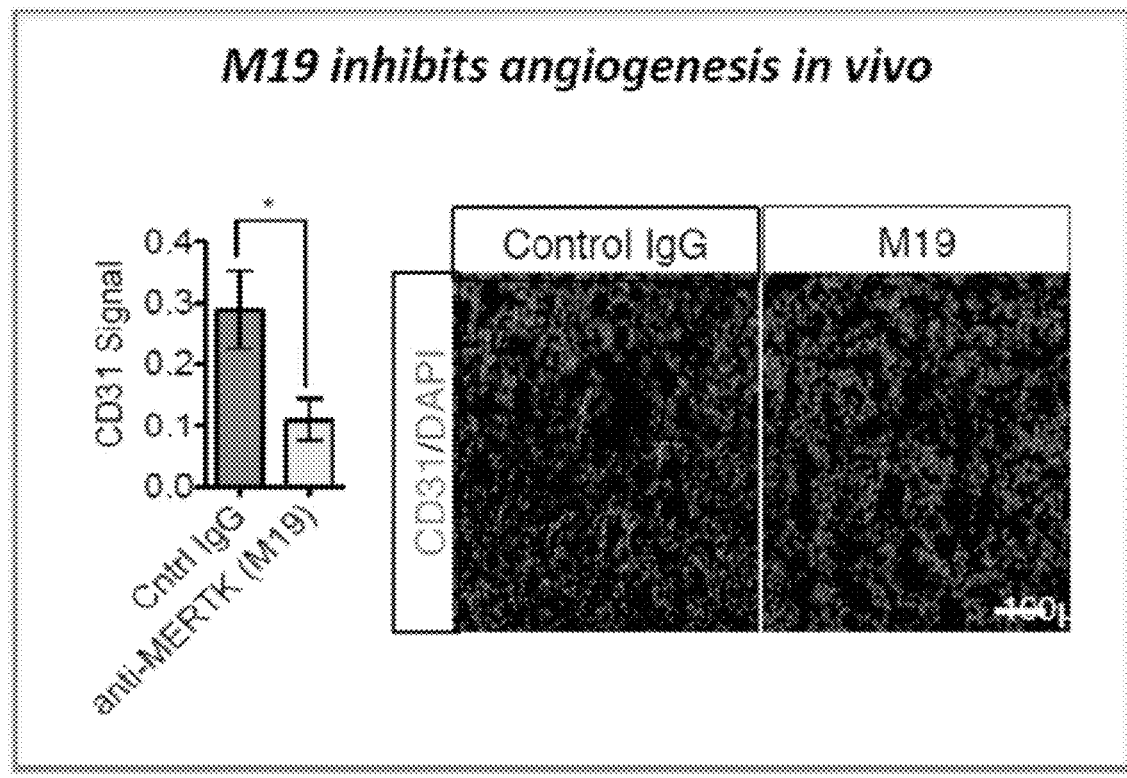

FIG. 10: Treatment with M19 inhibits angiogenesis in vivo. Mammary fat pad xenograft tumors that were grown for 58 days treated with 250 µg of either control antibody (IgG) or M19 antibody twice weekly were double stained for DAPI and CD31. The vessel density was quantified by using a thresholded CD31 signal. N=4. Error bars represent standard error of the mean. P-values were obtained using student's T-test (*p<0.05)

FIG. 11: M6 binds to MERTK with high affinity. M6 binds to human MERTK with high affinity. A diagram showing antibody binding kinetics for M6 (Mer-M6) against human MERTK (hMer) using biolayer interferometry. Purified M6 was loaded on an AMQ sensor at a concentration of 1 microgram/mL to test binding against analytes in solution. All analytes were prepared at 5 nM with a 2-fold dilution series for a total of 7 concentrations. Kinetic fits were calculated using a 1:1 model, with Local fits for each concentration as well as an overall Global fit. Overall calculated binding affinities ($K_D$) for M6 binding to human MERTK was 4.6 picomolar.

Figure 12:
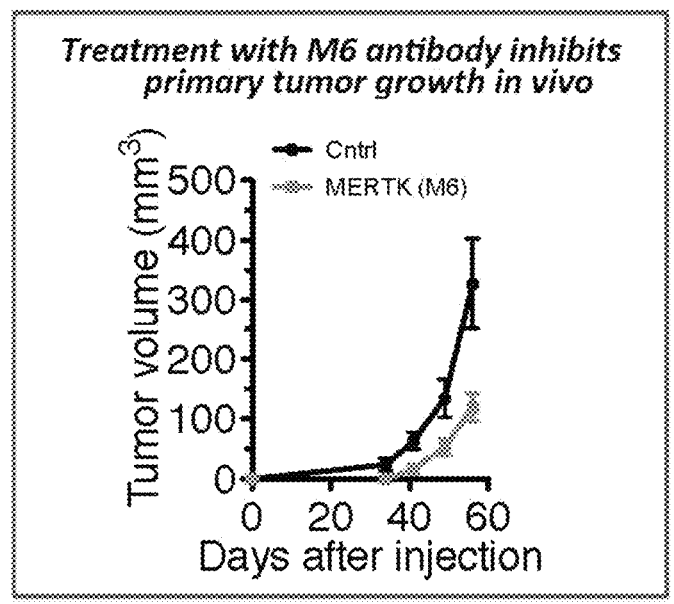

FIG. 12: Treatment with M6 inhibits primary tumor growth of triple-negative breast cancer in vivo. Mammary fat pad tumor growth by 2000 MDA-MB-231 in mice treated biweekly for 21 days with either 250 µg of control antibody or M6 antibody. N=4. Error bars represent standard error of the mean.

5. DETAILED DESCRIPTION

Provided herein are antibody-drug conjugates comprising: (a) an antibody moiety that is an anti-MERTK antibody (e.g., a monoclonal antibody) or an antigen-binding fragment thereof that specifically binds to MERTK (e.g., human MERTK, or both human and mouse MERTK) and agonizes MERTK signaling of endothelial cells; (b) one or more drug moieties, each drug moiety being a cytotoxic agent; and (c) optionally a linker; wherein the cytotoxic agent is conjugated directly to the antibody moiety or is conjugated to the antibody moiety via the linker. The term "conjugated" as used in this disclosure shall mean covalently bound, which can be directly or via an intervening covalently bound structure.

In certain embodiments, the antibody-drug conjugate provided herein has a molar ratio of the antibody moiety to the drug moiety that is between 1:1 and 1:20. In specific embodiments, the antibody-drug conjugate provided herein has a molar ratio of the antibody moiety to the drug moiety that is between 1:1 and 1:15. In specific embodiments, the antibody-drug conjugate provided herein has a molar ratio of the antibody moiety to the drug moiety that is between 1:1 and 1:12. In specific embodiments, the antibody-drug conjugate provided herein has a molar ratio of the antibody moiety to the drug moiety that is between 1:1 and 1:8. In preferred embodiments, the antibody-drug conjugate provided herein has a molar ratio of the antibody moiety to the drug moiety that is between 1:3 and 1:5. In a specific embodiment, the antibody-drug conjugate provided herein has a molar ratio of the antibody moiety to the drug moiety that is 1:3. In another specific embodiment, the antibody-drug conjugate provided herein has a molar ratio of the antibody moiety to the drug moiety that is 1:4. In another specific embodiment, the antibody-drug conjugate provided herein has a molar ratio of the antibody moiety to the drug moiety that is 1:5.

The drug moiety is conjugated to one or more chains of the antibody moiety. In some embodiments, the drug moiety is conjugated to one chain of the antibody moiety (for example, when the antibody moiety is a scFv, or when the antibody moiety is a multi-chain antibody, such as an immunoglobulin (which is a tetramer), or antigen-binding fragment thereof). In other embodiments, the drug moiety is conjugated to two or more chains of the antibody moiety (when the antibody moiety is a multi-chain antibody, such as an immunoglobulin, or antigen-binding fragment thereof). In a specific embodiment, the drug moiety is conjugated to two identical chains of an immunoglobulin, e.g., the heavy chains or the light chains. In other embodiments, the drug moiety is conjugated to all chains of the antibody moiety (when the antibody moiety is a multi-chain antibody, such as an immunoglobulin or antigen-binding fragment thereof).

In a specific embodiment, the drug moiety is conjugated to one or more sites in the constant region of an antibody. In a particular embodiment, the drug moiety is conjugated to the Fc region of an antibody that is an immunoglobulin.

In certain embodiments, an anti-MERTK antibody or antigen-binding fragment thereof described herein specifically recognizes the extracellular domain of MERTK (e.g., human MERTK, or both human and mouse MERTK). In a particular embodiment, an anti-MERTK antibody or antigen-binding fragment thereof described herein does not bind a 185 kilodalton (kD) MERTK glycoform expressed in Jurkat cells, a 205 kD MERTK glycoform in the monocytic cell line U937, 135-140 kD MERTK glycoforms expressed in human leukemia cells (e.g. human T-cell acute lymphoblastic leukemia) or 170-190 kD MERTK glycoforms expressed in human leukemia cells (e.g. human T-cell acute lymphoblastic leukemia). In certain embodiments, an anti-MERTK antibody or antigen-binding fragment thereof described herein does not decrease the expression level of MERTK on cancer cells. In a particular embodiment, an anti-MERTK antibody or antigen-binding fragment thereof described herein does not decrease the expression level of MERTK on the glioblastoma multiforme cell line A172. In specific embodiments, an anti-MERTK antibody or antigen-binding fragment thereof described herein is isolated. In a specific embodiment, an anti-MERTK antibody or antigen-binding fragment thereof described herein specifically binds to human MERTK protein comprising the amino acid sequence of SEQ ID NO: 57. In another specific embodiment, an anti-MERTK antibody or antigen-binding fragment thereof described herein specifically binds to the extracellular region of human MERTK, comprising the amino acid sequence of SEQ ID NO: 58. In another specific embodiment, an anti-MERTK antibody or antigen-binding fragment thereof described herein specifically binds to SEQ ID NO: 58. In a specific embodiment, an anti-MERTK antibody or antigen-binding fragment thereof described herein comprises two antigen-binding sites that bind to MERTK; in a particular embodiment, the two antigen-binding sites bind to the same epitope on MERTK; in a particular embodiment, the two-antigen binding sites comprise identical CDRs.

Antibodies can include, for example, monoclonal antibodies, polyclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, disulfide-linked Fvs (sdFv), and anti-idiotypic (anti-Id) antibodies (including, e.g., anti-anti-Id antibodies). In certain embodiments, antibodies described herein are polyclonal antibodies. In a preferred embodiment, the antibodies described herein are monoclonal antibodies. Antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class or subclass thereof. In a specific embodiment, the antibody is a humanized monoclonal antibody. In another specific embodiment, the antibody is a human monoclonal antibody, preferably that is an immunoglobulin.

As used herein, the terms "antigen-binding fragment", "antigen-binding region", and similar terms refer to a portion of an antibody molecule which comprises the amino acid residues that confer on the antibody molecule its specificity for the antigen (e.g., the complementarity determining regions (CDR)). The antigen-binding region can be derived from any animal species, such as rodents (e.g., mouse, rat or hamster) and humans. By way of example, antigen-binding fragments include Fab fragments, F(ab')$_2$ fragments, and antigen binding fragments of any of the antibodies described above.

As used herein, the terms "variable region" or "variable domain" are used interchangeably and are common in the art. The variable region typically refers to a portion of an antibody, generally, a portion of a light or heavy chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

CDRs are defined in various ways in the art, including the Kabat, Chothia, AbM, contact, IMGT, and Exemplary definitions. The Kabat definition is based on sequence variability and is the most commonly used definition to predict CDR regions (Kabat, Elvin A. et al., Sequences of Proteins of Immunological Interest. Bethesda: National Institutes of Health, 1983). The Chothia definition is based on the location of the structural loop regions (Chothia et al., (1987) J Mol Biol 196: 901-917). The AbM definition, a compromise between the Kabat and Chothia definitions, is an integral suite of programs for antibody structure modeling produced by the Oxford Molecular Group (bioinf.org.uk/abs) (Martin A C R et al., (1989) PNAS 86: 9268-9272). The contact definition is based on an analysis of the available complex crystal structures (bioinf.org.uk/abs) (see MacCallum R M et al., (1996) J Mol Biol 5: 732-745). The IMGT definition is from the IMGT ("IMGT®, the international ImMunoGeneTics Information System® website imgt.org, founder and director: Marie-Paule Lefranc, Montpellier, France). The Exemplary definition is a combination of AbM and Kabat (Presta et al., (1997) Cancer Res 57: 4593-4599).

Also described herein are isolated nucleic acids (polynucleotides), such as complementary DNA (cDNA), encoding such anti-MERTK antibodies, and antigen-binding fragments thereof. In the case where the cytotoxic agent is a peptide or protein, or where the cytotoxic agent and the linker (if there is one) are peptides or proteins, nucleic acids encoding the antibody-drug conjugates are also provided. Further described herein are vectors (e.g., expression vectors) and cells (e.g., host cells) comprising nucleic acids (polynucleotides) encoding such anti-MERTK antibodies or antigen-binding fragments thereof or antibody-drug conjugates. Also described herein are methods of making such antibodies or antibody-drug conjugates.

In other aspects, provided herein are methods of producing the antibody-drug conjugates that comprise (i) the anti-MERTK antibodies or antigen-binding fragments thereof, and (ii) cytotoxic agents conjugated directly to the anti- MERTK antibodies or antigen-binding fragments, or conjugated to the anti-MERTK antibodies or antigen-binding fragments via linkers.

In other aspects, provided herein are methods of treating cancer in a subject comprising administering to the subject an effective amount of the antibody-drug conjugate that comprises (i) the anti-MERTK antibody or antigen-binding fragment thereof, and (ii) cytotoxic agents conjugated directly to the anti-MERTK antibodies or antigen-binding fragments, or conjugated to the anti-MERTK antibodies or antigen-binding fragments via linkers. Related compositions (e.g., pharmaceutical compositions) and kits are also provided.

5.1. The Antibody Moiety

Non-limiting exemplary anti-MERTK antibodies or antigen-binding fragments thereof that can be the antibody moiety of the antibody-drug conjugates provided herein are presented below.

5.1.1. Sequences and Variants

In specific embodiments, an anti-MERTK antibody or antigen-binding fragment thereof described herein comprises the VH CDR1 of the antibody in Table 1 or 3 as defined by Kabat, Chothia, AbM, Contact, IMGT, or Exemplary. In some embodiments, an anti-MERTK antibody or antigen-binding fragment thereof described herein comprises the VH CDR2 of the antibody in Tables 1 or 3 as defined by Kabat, Chothia, AbM, Contact, IMGT, or Exemplary. In some embodiments, an anti-MERTK antibody or antigen-binding fragment thereof described herein comprises the VH CDR3 of the antibody in Tables 1 or 3 as defined by Kabat, Chothia, AbM, Contact, IMGT, or Exemplary. In some embodiments, an anti-MERTK antibody or antigen-binding fragment thereof described herein comprises one, two or all three of VH CDRs of an antibody in Table 1 or 3 (e.g., the VH CDRs in one row of Table 1, for example, all of the Kabat VH CDRs for antibody M6).

In specific embodiments, an anti-MERTK antibody or antigen-binding fragment thereof described herein comprises the VL CDR1 of the antibody in Table 2 or 4 as defined by Kabat, Chothia, AbM, Contact, IMGT, or Exemplary. In some embodiments, an anti-MERTK antibody or antigen-binding fragment thereof described herein comprises the VL CDR2 of the antibody in Tables 2 or 4 as defined by Kabat, Chothia, AbM, Contact, IMGT, or Exemplary. In some embodiments, an anti-MERTK antibody or antigen-binding fragment thereof described herein comprises the VL CDR3 of the antibody in Tables 2 or 4 as defined by Kabat, Chothia, AbM, Contact, IMGT, or Exemplary. In some embodiments, an anti-MERTK antibody or antigen-binding fragment thereof described herein comprises one, two or all three of VL CDRs of an antibody in Table 2 or 4 (e.g., the VL CDRs in one row of Table 2, for example, all of the Kabat VL CDRs for antibody M6).

TABLE 1

Antibody M6 VH CDR Amino Acid Sequences

| Definitions | VH CDR1 | VH CDR2 | VH CDR3 |
| --- | --- | --- | --- |
| Kabat | NYGMN (SEQ ID NO: 1) | WINTYTGEPTYADDFKG (SEQ ID NO: 6) | KSTVVSRYFDV (SEQ ID NO: 11) |
| Chothia | GYTFTNY (SEQ ID NO: 2) | TYTG (SEQ ID NO: 7) | STVVSRYFD (SEQ ID NO: 12) |
| AbM | GYTFTNYGMN (SEQ ID NO: 3) | WINTYTGEPT (SEQ ID NO: 8) | KSTVVSRYFDV (SEQ ID NO: 11) |
| Contact | TNYGMN (SEQ ID NO: 4) | WMGWINTYTGEPT (SEQ ID NO: 9) | ARKSTVVSRYFD (SEQ ID NO: 13) |
| IMGT | GYTFTNYG (SEQ ID NO: 5) | INTYTGEP (SEQ ID NO: 10) | ARKSTVVSRYFDV (SEQ ID NO: 14) |
| Exemplary | GYTFTNYGMN (SEQ ID NO: 3) | WINTYTGEPTYADDFKG (SEQ ID NO: 6) | KSTVVSRYFDV (SEQ ID NO: 11) |

TABLE 2

Antibody M6 VL CDR Amino Acid Sequences

| Definitions | VL CDR1 | VL CDR2 | VL CDR3 |
| --- | --- | --- | --- |
| Kabat | KASQDVGDAVT (SEQ ID NO: 15) | WASTRHT (SEQ ID NO: 19) | QQYRSYPLT (SEQ ID NO: 22) |
| Chothia | SQDVGDA (SEQ ID NO: 16) | WAS (SEQ ID NO: 20) | YRSYPL (SEQ ID NO: 23) |
| AbM | KASQDVGDAVT (SEQ ID NO: 15) | WASTRHT (SEQ ID NO: 19) | QQYRSYPLT (SEQ ID NO: 22) |
| Contact | GDAVTWC (SEQ ID NO: 17) | LLIYWASTRH (SEQ ID NO: 21) | QQYRSYPL (SEQ ID NO: 24) |

TABLE 2-continued

Antibody M6 VL CDR Amino Acid Sequences

| Definitions | VL CDR1 | VL CDR2 | VL CDR3 |
|---|---|---|---|
| IMGT | QDVGDA (SEQ ID NO: 18) | WAS (SEQ ID NO: 20) | QQYRSYPLT (SEQ ID NO: 22) |
| Exemplary | KASQDVGDAVT (SEQ ID NO: 15) | WASTRHT (SEQ ID NO: 19) | QQYRSYPLT (SEQ ID NO: 22) |

TABLE 3

Antibody M19 VH CDR Amino Acid Sequences

| Definitions | VH CDR1 | VH CDR2 | VH CDR3 |
|---|---|---|---|
| Kabat | DYSMH (SEQ ID NO: 25) | WINTDTGEPTYADDFKG (SEQ ID NO: 30) | WFGAMDY (SEQ ID NO: 35) |
| Chothia | NYTFTDY (SEQ ID NO: 26) | TDTG (SEQ ID NO: 31) | FGAMD (SEQ ID NO: 36) |
| AbM | NYTFTDYSMH (SEQ ID NO: 27) | WINTDTGEPT (SEQ ID NO: 32) | WFGAMDY (SEQ ID NO: 35) |
| Contact | TDYSMH (SEQ ID NO: 28) | WVGWINTDTGEPT (SEQ ID NO: 33) | ARWFGAMD (SEQ ID NO: 37) |
| IMGT | NYTFTDYS (SEQ ID NO: 29) | INTDTGEP (SEQ ID NO: 34) | ARWFGAMDY (SEQ ID NO: 38) |
| Exemplary | NYTFTDYSMH (SEQ ID NO: 27) | WINTDTGEPTYADDFKG (SEQ ID NO: 30) | WFGAMDY (SEQ ID NO: 35) |

TABLE 4

Antibody M19 VL CDR Amino Acid Sequences

| Definitions | VL CDR1 | VL CDR2 | VL CDR3 |
|---|---|---|---|
| Kabat | KASQDVTNVVA (SEQ ID NO: 39) | SASYRYT (SEQ ID NO: 43) | QQYYRTPRT (SEQ ID NO: 46) |
| Chothia | SQDVTNV (SEQ ID NO: 40) | SAS (SEQ ID NO: 44) | YYRTPR (SEQ ID NO: 47) |
| AbM | KASQDVTNVVA (SEQ ID NO: 39) | SASYRYT (SEQ ID NO: 43) | QQYYRTPRT (SEQ ID NO: 46) |
| Contact | TNVVAWY (SEQ ID NO: 41) | LLIYSASYRY (SEQ ID NO: 45) | QQYYRTPR (SEQ ID NO: 48) |
| IMGT | QDVTNV (SEQ ID NO: 42) | SAS (SEQ ID NO: 44) | QQYYRTPRT (SEQ ID NO: 46) |
| Exemplary | KASQDVTNVVA (SEQ ID NO: 39) | SASYRYT (SEQ ID NO: 43) | QQYYRTPRT (SEQ ID NO: 46) |

TABLE 5

Antibody M6 Variable Region Amino Acid Sequences

VH QVKLEESGPELKKPGETVKISCKASGYTFTNYGMNWVKQAPGKGLK
WMGWINTYTGEPTYADDFKGRFVFSLETSASTAYLQINNLKNEDMA
TYFCARKSTVVSRYFDVWGAGTTVTVSS
(SEQ ID NO: 49)

VL DIVLTQTHKFMSTSVGDRVSITCKASQDVGDAVTWCQQKPGQPPKL
LIYWASTRHTGVPDRFTGSGSGTDFTLTINNVQSEDLADYFCQQYR
SYPLTFGAGTKLELKR
(SEQ ID NO: 50)

TABLE 6

Antibody M19 Variable Region Amino Acid Sequences

VH EVQLEESGPDLKKPGETVKISCKASNYTFTDYSMHWVKQAPGKGLKW
VGWINTDTGEPTYADDFKGRFAFSLETSASTAYLQINNLKNEDTATY
FCARWFGAMDYWGQGTSVTVSS
(SEQ ID NO: 51)

VL DIVITQSHKFMSTSVGDRVSITCKASQDVTNVVAWYQQKPGQSPKLL
IYSASYRYTGVPDRFTGSGSGTDFTFTISSVQAEDLAVYYCQQYYRT
PRTFGGGTKLEIKR
(SEQ ID NO: 52)

TABLE 7

Antibody M6 Variable Region DNA Sequences

VH CAGGTTAAGCTGGAGGAGTCTGGACCTGAGCTGAAGAAGCCTGGAGA
GACAGTCAAGATCTCCTGCAAGGCTTCTGGATATACCTTCACAAACT
ATGGAATGAACTGGGTGAAGCAGGCTCCAGGAAAGGGTTTAAAGTGG
ATGGGCTGGATAAACACCTACACTGGAGAGCCAACATATGCTGATGA
CTTCAAGGGACGGTTTGTCTTCTCTTTGGAAACCTCTGCCAGCACTG
CCTACTTGCAGATCAACAACCTCAAAAATGAGGACATGGCCACATAT
TTCTGTGCAAGAAAAAGTACGGTAGTAAGTAGGTACTTCGATGTCTG
GGGCGCAGGGACCACGGTCACCGTCTCCTCA
(SEQ ID NO: 53)

VL GGGATATTGTGCTGACACAGACTCACAAATTCATGTCCACATCAGTA
GGAGACAGGGTCAGCATCACCTGCAAGGCCAGTCAGGATGTGGGTGA
TGCTGTAACCTGGTGTCAACAGAAACCAGGTCAACCTCCTAAACTAC
TGATTTACTGGGCATCCACCCGGCACACTGGAGTCCCTGATCGCTTC
ACAGGCAGTGGGTCTGGGACAGATTTCACTCTCACCATTAACAATGT
GCAGTCTGAAGACTTGGCAGATTATTTCTGTCAGCAATATCGCAGCT
ATCCTCTCACGTTCGGTGCTGGGACCAAGCTGGAGCTG
(SEQ ID NO: 54)

TABLE 8

Antibody M19 Variable Region DNA Sequences

VH GAGGTCCAGCTGGAGGAGTCTGGACCTGACCTGAAGAAGCCTGGAGAG
ACAGTCAAGATCTCCTGCAAGGCTTCTAATTATACCTTCACAGACTAT
TCAATGCACTGGGTGAAGCAGGCTCCAGGAAAGGGTTTAAAGTGGGTG
GGCTGGATAAACACTGACACTGGTGAGCCAACATATGCAGATGACTTC
AAGGGACGCTTTGCCTTCTCTTTGGAAACCTCTGCCAGCACTGCCTAT
TTACAGATCAACAACCTCAAAAATGAGGACACGGCTACATATTTCTGT
GCTAGATGGTTTGGTGCTATGGACTACTGGGGTCAAGGAACCTCAGTC
ACCGTCTCCTCAGCCAAAACGACACCCCCATCTGTCTATTCC
(SEQ ID NO: 55)

VL GGGATATTGTGATCACACAGTCTCACAAATTCATGTCCACATCAGTAG
GAGACAGGGTCAGCATCACCTGCAAGGCCAGTCAGGATGTGACTAATG
TTGTAGCCTGGTATCAACAGAAACCAGGACAATCTCCTAAACTACTGA
TTTATTCGGCATCCTACCGGTACACTGGAGTCCCTGATCGCTTCACTG
GCAGTGGATCTGGGACGGATTTCACTTTCACCATCAGCAGTGTGCAGG
CTGAAGACCTGGCAGTTTATTACTGTCAGCAATATTATCGTACTCCTC
GGACGTTCGGTGGAGGCACCAAGCTGGAAATCAACGG
(SEQ ID NO: 56)

TABLE 9

MERTK Protein Sequences

Full-Length Human MERTK (Swiss-Prot ID: Q12866.2)

MGPAPLPLLLGLFLPALWRRAITEAREEAKPYPLFPG
PFPGSLQTDHTPLLSLPHASGYQPALMFSPTQPGRPH
TGNVAIPQVTSVESKPLPPLAFKHTVGHIILSEHKGV
KFNCSISVPNIYQDTTISWWKDGKELLGAHHAITQFY
PDDEVTAIIASFSITSVQRSDNGSYICKMKINNEEIV
SDPIYIEVQGLPHFTKQPESMNVTRNTAFNLTCQAVG
PPEPVNIFWVQNSSRVNEQPEKSPSVLTVPGLTEMAV
FSCEAHNDKGLTVSKGVQINIKAIPSPPTEVSIRNST
AHSILISWVPGFDGYSPFRNCSIQVKEADPLSNGSVM
IFNTSALPHLYQIKQLQALANYSIGVSCMNEIGWSAV
SPWILASTTEGAPSVAPLNVTVFLNESSDNVDIRWMK
PPTKQQDGELVGYRISHVWQSAGISKELLEEVGQNGS
RARISVQVHNATCTVRIAAVTRGGVGPFSDPVKIFIP
AHGWVDYAPSSTPAPGNADPVLIIFGCFCGFILIGLI
LYISLAIRKRVQETKFGNAFTEEDSELVVNYIAKKSF
CRRAIELTLHSLGVSEELQNKLEDVVIDRNLLILGKI
LGEGEFGSVMEGNLKQEDGTSLKVAVKTMKLDNSSQR
EIEEFLSEAACMKDFSHPNVIRLLGVCIEMSSQGIPK
PMVILPFMKYGDLHTYLLYSRLETGPKHIPLQTLLKF
MVDIALGMEYLSNRNFLHRDLAARNCMLRDDMTVCVA
DFGLSKKIYSGDYYRQGRIAKMPVKWIAIESLADRVY
TSKSDVWAFGVTMWEIATRGMTPYPGVQNHEMYDYLL
HGHRLKQPEDCLDELYEIMYSCWRTDPLDRPTFSVLR
LQLEKLLESLPDVRNQADVIYVNTQLLESSEGLAQGS
TLAPLDLNIDPDSIIASCTPRAAISVVTAEVHDSKPH
EGRYILNGGSEEWEDLTSAPSAAVTAEKNSVLPGERL
VRNGVSWSHSSMLPLGSSLPDELLFADDSSEGSEVLM
(SEQ ID NO: 57)

Extracellular Doman of MERTK Used for Immunization

REEAKPYPLFPGPFPGSLQTDHTPLLSLPHASGYQPA
LMFSPTQPGRPHTGNVAIPQVTSVESKPLPPLAFKHT
VGHIILSEHKGVKFNCSISVPNIYQDTTISWWKDGKE
LLGAHHAITQFYPDDEVTAIIASFSITSVQRSDNGSY
ICKMKINNEEIVSDPIYIEVQGLPHFTKQPESMNVTR
NTAFNLTCQAVGPPEPVNIFWVQNSSRVNEQPEKSPS
VLTVPGLTEMAVFSCEAHNDKGLTVSKGVQINIKAIP
SPPTEVSIRNSTAHSILISWVPGFDGYSPFRNCSIQV
KEADPLSNGSVMIFNTSALPHLYQIKQLQALANYSIG
VSCMNEIGWSAVSPWILASTTEGAPSVAPLNVTVFLN
ESSDNVDIRWMKPPTKQQDGELVGYRISHVWQSAGIS
KELLEEVGQNGSRARISVQVHNATCTVRIAAVTRGGV
GPFSDPVKIFIPAHGWVDYAPSSTPAPGNA
(SEQ ID NO: 58)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of NYGMN; (SEQ ID NO: 1)
and/or (b) a VH CDR2 of WINTYTGEPTYADDFKG; (SEQ ID NO: 6)
and/or (c) a VH CDR3 of KSTVVSRYFDV. (SEQ ID NO: 11)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of GYTFTNY; (SEQ ID NO: 2)
and/or (b) a VH CDR2 of TYTG; (SEQ ID NO: 7)
and/or (c) a VH CDR3 of STVVSRYFD. (SEQ ID NO: 12)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of GYTFTNYGMN; (SEQ ID NO: 3)
and/or (b) a VH CDR2 of WINTYTGEPT; (SEQ ID NO: 8)
and/or (c) a VH CDR3 of KSTVVSRYFDV (SEQ ID NO: 11)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of TNYGMN; (SEQ ID NO: 4)
and/or (b) a VH CDR2 of WMGWINTYTGEPT; (SEQ ID NO: 9)
and/or (c) a VH CDR3 of ARKSTVVSRYFD. (SEQ ID NO: 13)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of GYTFTNYG; (SEQ ID NO: 5)
and/or (b) a VH CDR2 of INTYTGEP; (SEQ ID NO: 10)
and/or (c) a VH CDR3 of ARKSTVVSRYFDV. (SEQ ID NO: 14)

In a particular embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a heavy chain variable region (VH) comprising:

(a) a VH CDR1 of GYTFTNYGMN; (SEQ ID NO: 3)
and/or (b) a VH CDR2 of WINTYTGEPTYADDFKG; (SEQ ID NO: 6)
and/or (c) a VH CDR3 of KSTVVSRYFDV. (SEQ ID NO: 11)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of KASQDVGDAVT; (SEQ ID NO: 15)
and/or (b) a VL CDR2 of WASTRHT; (SEQ ID NO: 19)
and/or (c) a VL CDR3 of QQYRSYPLT. (SEQ ID NO: 22)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of SQDVGDA; (SEQ ID NO: 16)
and/or (b) a VL CDR2 of WAS; (SEQ ID NO: 20)
and/or (c) a VL CDR3 of YRSYPL. (SEQ ID NO: 23)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of GDAVTWC; (SEQ ID NO: 17)
and/or (b) a VL CDR2 of LLIYWASTRH; (SEQ ID NO: 21)
and/or (c) a VL CDR3 of QQYRSYPL. (SEQ ID NO: 24)

In another embodiment, an anti-MERTK antibody or an antigen-binding fragment thereof described herein, which specifically binds to MERTK (e.g., human MERTK, or both human and mouse MERTK) and agonizes MERTK signaling of endothelial cells, comprises a light chain variable region (VL) comprising:

(a) a VL CDR1 of QDVGDA; (SEQ ID NO: 18) and/or (b) a VL CDR2 comprising, of WAS; (SEQ ID NO: 20) and/or (c) a VL CDR3 of QQYRSYPLT. (SEQ ID NO: 22)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of DYSMH; (SEQ ID NO: 25) and/or (b) a VH CDR2 of WINTDTGEPTYADDFKG; (SEQ ID NO: 30) and/or (c) a VH CDR3 of WFGAMDY. (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of NYTFTDY; (SEQ ID NO: 26) and/or (b) a VH CDR2 of TDTG; (SEQ ID NO: 31) and/or (c) a VH CDR3 of FGAMD. (SEQ ID NO: 36)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of NYTFTDYSMH; (SEQ ID NO: 27) and/or (b) a VH CDR2 of WINTDTGEPT; (SEQ ID NO: 32) and/or (c) a VH CDR3 of WFGAMDY. (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of TDYSMH; (SEQ ID NO: 28) and/or (b) a VH CDR2 of WVGWINTDTGEPT; (SEQ ID NO: 33) and/or (c) a VH CDR3 of ARWFGAMD. (SEQ ID NO: 37)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of NYTFTDYS; (SEQ ID NO: 29) and/or (b) a VH CDR2 of INTDTGEP; (SEQ ID NO: 34) and/or (c) a VH CDR3 of ARWFGAMDY. (SEQ ID NO: 38)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region (VH) comprising:

(a) a VH CDR1 of NYTFTDYSMH; (SEQ ID NO: 27) and/or (b) a VH CDR2 of WINTDTGEPTYADDFKG; (SEQ ID NO: 30) and/or (c) a VH CDR3 of WFGAMDY. (SEQ ID NO: 35)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
KASQDVTNVVA; (SEQ ID NO: 39)
and/or (b) a VL CDR2 of
SASYRYT; (SEQ ID NO: 43)
and/or (c) a VL CDR3 of
QQYYRTPRT. (SEQ ID NO: 46)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
SQDVTNV; (SEQ ID NO: 40)
and/or (b) a VL CDR2 of
SAS; (SEQ ID NO: 44)
and/or (c) a VL CDR3 of
YYRTPR. (SEQ ID NO: 47)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
TNVVAWY; (SEQ ID NO: 41)
and/or (b) a VL CDR2 of
LLIYSASYRY; (SEQ ID NO: 45)
and/or (c) a VL CDR3 of
QQYYRTPR. (SEQ ID NO: 48)

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a light chain variable region (VL) comprising:

(a) a VL CDR1 of
QDVTNV; (SEQ ID NO: 42)
and/or (b) a VL CDR2 of
(SEQ ID NO: 44)

SAS;
and/or (c) a VL CDR3 of
QQYYRTPRT. (SEQ ID NO: 46)

In specific embodiments, the antibody or antigen-binding fragment thereof comprises one, two, or all three of the VH CDRs above. In certain embodiments, the antibody or antigen-binding fragment thereof comprises a VH CDR1 in Table 1 or Table 3. In some embodiments, the antibody or antigen-binding fragment thereof comprises a VH CDR2 in Table 1 or Table 3. In certain embodiments, the antibody or antigen-binding fragment thereof comprises a VH CDR3 in Table 1 or Table 3. In certain embodiments, the antibody or antigen-binding fragment thereof comprises a VH CDR1, a VH CDR2, and a VH CDR3 of the antibody M6 (Table 1). In certain embodiments, the antibody or antigen-binding fragment thereof comprises a VH CDR1, a VH CDR2, and a VH CDR3 of the antibody M19 (Table 3).

In specific embodiments, the antibody or antigen-binding fragment thereof comprises one, two, or all three of the VL CDRs above. In certain embodiments, the antibody or antigen-binding fragment thereof comprises a VL CDR1 in Table 2 or Table 4. In some embodiments, the antibody or antigen-binding fragment thereof comprises a VL CDR2 in Table 2 or Table 4. In certain embodiments, the antibody or antigen-binding fragment thereof comprises a VL CDR3 in Table 2 or Table 4. In certain embodiments, the antibody or antigen-binding fragment thereof comprises a VL CDR1, a VL CDR2, and a VL CDR3 of the antibody M6 (Table 2). In certain embodiments, the antibody or antigen-binding fragment thereof comprises a VL CDR1, a VL CDR2, and a VL CDR3 of the antibody M19 (Table 4).

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
NYGMN; (SEQ ID NO: 1)
and/or (b) a VH CDR2 of
WINTYTGEPTYADDFKG; (SEQ ID NO: 6)
and/or (c) a VH CDR3 of
KSTVVSRYFDV; (SEQ ID NO: 11)
and/or (d) a VL CDR1 of
KASQDVGDAVT; (SEQ ID NO: 15)
and/or (e) a VL CDR2 of
WASTRHT; (SEQ ID NO: 19)
and/or (f) a VL CDR3 of
QQYRSYPLT. (SEQ ID NO: 22)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
(SEQ ID NO: 2)
GYTFTNY;
and/or (b) a VH CDR2 of
(SEQ ID NO: 7)
TYTG;
and/or (c) a VH CDR3 of
(SEQ ID NO: 12)
STVVSRYFD;
and/or (d) a VL CDR1 of
(SEQ ID NO: 16)
SQDVGDA;
and/or (e) a VL CDR2 of
(SEQ ID NO: 20)
WAS;
and/or (f) a VL CDR3 of
(SEQ ID NO: 23)
YRSYPL.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
(SEQ ID NO: 3)
GYTFTNYGMN;
and/or (b) a VH CDR2 of
(SEQ ID NO: 8)
WINTYTGEPT;
and/or (c) a VH CDR3 of
(SEQ ID NO: 11)
KSTVVSRYFDV;
and/or (d) a VL CDR1 of
(SEQ ID NO: 15)
KASQDVGDAVT;
and/or (e) a VL CDR2 of
(SEQ ID NO: 19)
WASTRHT;
and/or (f) a VL CDR3 of
(SEQ ID NO: 22)
QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
(SEQ ID NO: 4)
TNYGMN;
and/or (b) a VH CDR2 of
(SEQ ID NO: 9)
WMGWINTYTGEPT;
and/or (c) a VH CDR3 of
(SEQ ID NO: 13)
ARKSTVVSRYFD;
and/or (d) a VL CDR1 of
(SEQ ID NO: 17)
GDAVTWC;
and/or (e) a VL CDR2 of
(SEQ ID NO: 21)
LLIYWASTRH;
and/or (f) a VL CDR3 of
(SEQ ID NO: 24)
QQYRSYPL.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
(SEQ ID NO: 5)
GYTFTNYG;
and/or (b) a VH CDR2 of
(SEQ ID NO: 10)
INTYTGEP;
and/or (c) a VH CDR3 of
(SEQ ID NO: 14)
ARKSTVVSRYFDV;
and/or (d) a VL CDR1 of
(SEQ ID NO: 18)
QDVGDA;
and/or (e) a VL CDR2 comprising, of
(SEQ ID NO: 20)
WAS;
and/or (f) a VL CDR3 of
(SEQ ID NO: 22)
QQYRSYPLT.

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
GYTFTNYGMN; (SEQ ID NO: 3)
and/or (b) a VH CDR2 of
WINTYTGEPTYADDFKG; (SEQ ID NO: 6)
and/or (c) a VH CDR3 of
KSTVVSRYFDV; (SEQ ID NO: 11)
and/or (d) a VL CDR1 of
KASQDVGDAVT; (SEQ ID NO: 15)
and/or (e) a VL CDR2 of
WASTRHT; (SEQ ID NO: 19)
and/or (f) a VL CDR3 of
QQYRSYPLT. (SEQ ID NO: 22)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
DYSMH; (SEQ ID NO: 25)
and/or (b) a VH CDR2 of
WINTDTGEPTYADDFKG; (SEQ ID NO: 30)
and/or (c) a VH CDR3 of
WFGAMDY; (SEQ ID NO: 35)
and/or (d) a VL CDR1 of
KASQDVTNVVA; (SEQ ID NO: 39)
and/or (e) a VL CDR2 of
SASYRYT; (SEQ ID NO: 43)
and/or (f) a VL CDR3 of
QQYYRTPRT. (SEQ ID NO: 46)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
NYTFTDY; (SEQ ID NO: 26)
and/or (b) a VH CDR2 of
TDTG; (SEQ ID NO: 31)
and/or (c) a VH CDR3 of
FGAMD; (SEQ ID NO: 36)
and/or (d) a VL CDR1 of
SQDVTNV; (SEQ ID NO: 40)
and/or (e) a VL CDR2 of
SAS; (SEQ ID NO: 44)
and/or (f) a VL CDR3 of
YYRTPR. (SEQ ID NO: 47)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
NYTFTDYSMH; (SEQ ID NO: 27)
and/or (b) a VH CDR2 of
WINTDTGEPT; (SEQ ID NO: 32)
and/or (c) a VH CDR3 of
WFGAMDY; (SEQ ID NO: 35)
and/or (d) a VL CDR1 of
KASQDVTNVVA; (SEQ ID NO: 39)
and/or (e) a VL CDR2 of
SASYRYT; (SEQ ID NO: 43)
and/or (f) a VL CDR3 of
QQYYRTPRT. (SEQ ID NO: 46)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
TDYSMH; (SEQ ID NO: 28)
and/or (b) a VH CDR2 of
WVGWINTDTGEPT; (SEQ ID NO: 33)
and/or (c) a VH CDR3 of
ARWFGAMD;                                         (SEQ ID NO: 37)
and/or (d) a VL CDR1 of
TNWAWY;                                           (SEQ ID NO: 41)
and/or (e) a VL CDR2 of
LLIYSASYRY;                                       (SEQ ID NO: 45)
and/or (f) a VL CDR3 of
QQYYRTPR.                                         (SEQ ID NO: 48)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
NYTFTDYS;                                         (SEQ ID NO: 29)
and/or (b) a VH CDR2 of
INTDTGEP;                                         (SEQ ID NO: 34)
and/or (c) a VH CDR3 of
ARWFGAMDY;                                        (SEQ ID NO: 38)
and/or (d) a VL CDR1 of
QDVTNV;                                           (SEQ ID NO: 42)
and/or (e) a VL CDR2 of
SAS;                                              (SEQ ID NO: 44)
and/or (f) a VL CDR3 of
QQYYRTPRT.                                        (SEQ ID NO: 46)

In a particular embodiment, an anti-MERTK antibody or antigen-binding fragment thereof, which specifically binds to MERTK (e.g., human MERTK, or both human and mouse MERTK) and agonizes MERTK signaling of endothelial cells, comprises:

(a) a VH CDR1 of
NYTFTDYSMH;                                       (SEQ ID NO: 27)
and/or (b) a VH CDR2 of
WINTDTGEPTYADDFKG;                                (SEQ ID NO: 30)
and/or (c) a VH CDR3 of
WFGAMDY;                                          (SEQ ID NO: 35)
and/or (d) a VL CDR1 of
KASQDVTNVVA;                                      (SEQ ID NO: 39)
and/or (e) a VL CDR2 of
SASYRYT;                                          (SEQ ID NO: 43)
and/or (f) a VL CDR3 of
QQYYRTPRT.                                        (SEQ ID NO: 46)

In specific embodiments, the antibody or antigen-binding fragment thereof comprises one, two, three, four, five or all six of the CDRs above. In certain embodiments, the antibody or antigen-binding fragment thereof comprises a VH CDR1 in Table 1 or Table 3. In some embodiments, the antibody or antigen-binding fragment thereof comprises a VH CDR2 in Table 1 or Table 3. In certain embodiments, the antibody or antigen-binding fragment thereof comprises a VH CDR3 in Table 1 or Table 3. In some embodiments, the antibody or antigen-binding fragment thereof comprises a VL CDR1 in Table 2 or Table 4. In some embodiments, the antibody or antigen-binding fragment thereof comprises a VL CDR2 in Table 2 or Table 4. In certain embodiments, the antibody or antigen-binding fragment thereof comprises a VL CDR3 in Table 2 or Table 4. In some embodiments, the antibody or antigen-binding fragment thereof comprises a VH CDR1, a VH CDR2, and a VH CDR3 of the antibody M6 (Table 1). In certain embodiments, the antibody or antigen-binding fragment thereof comprises a VH CDR1, a VH CDR2, and a VH CDR3 of the antibody M19 (Table 3). In certain embodiments, the antibody or antigen-binding fragment thereof comprises a VL CDR1, a VL CDR2, and a VL CDR3 of the antibody M6 (Table 2). In certain embodiments, the antibody or antigen-binding fragment thereof comprises a VL CDR1, a VL CDR2, and a VL CDR3 of the antibody M19 (Table 4). In certain embodiments, the antibody or antigen-binding fragment thereof comprises a VL CDR1, a VL CDR2, a VL CDR3, a VH CDR1, a VH CDR2, and a VH CDR3 of the antibody M6 (Tables 1 and 2). In certain embodiments, the antibody or antigen-binding fragment thereof comprises a VL CDR1, a VL CDR2, a VL CDR3, a VH CDR1, a VH CDR2, and a VH CDR3 of the antibody M19 (Tables 3 and 4).

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

(a) a VH CDR1 of
DYSMH;                                            (SEQ ID NO: 25)
and/or (b) a VH CDR2 of
WINTDTGEPTYADDFKG;                                (SEQ ID NO: 30)
and/or (c) a VH CDR3 of
WFGAMDY;                                          (SEQ ID NO: 35)

and
(ii) the VL comprises:

```
                              (SEQ ID NO: 39)
    (a) a VL CDR1 of
KASQDVTNVVA
and/or;

(SEQ ID NO: 43)
    (b) a VL CDR2 of
SASYRYT
and/or;

(SEQ ID NO: 46)
    (c) a VL CDR3 of
QQYYRTPRT.
```

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

```
                              (SEQ ID NO: 26)
    (a) a VH CDR1 of
NYTFTDY;
and/or (SEQ ID NO: 31)
    (b) a VH CDR2 of
TDTG;
and/or (SEQ ID NO: 36)
    (c) a VH CDR3 of
FGAMD;
``` and
(ii) the VL comprises:

```
                              (SEQ ID NO: 40)
    (a) a VL CDR1 of
SQDVTNV;
and/or (SEQ ID NO: 44)
    (b) a VL CDR2 of
SAS;
and/or (SEQ ID NO: 47)
    (c) a VL CDR3 of
YYRTPR.
```

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

```
                              (SEQ ID NO: 1)
    (a) a VH CDR1 of
NYGMN;
and/or (SEQ ID NO: 6)
    (b) a VH CDR2 of
WINTYTGEPTYADDFKG;
``` and/or

```
                              (SEQ ID NO: 11)
    (c) a VH CDR3 of
KSTVVSRYFDV;
``` and
(ii) the VL comprises:

```
                              (SEQ ID NO: 15)
    (a) a VL CDR1 of
KASQDVGDAVT;
and/or (SEQ ID NO: 19)
    (b) a VL CDR2 of
WASTRHT;
and/or (SEQ ID NO: 22)
    (c) a VL CDR3 of
QQYRSYPLT.
```

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

```
                              (SEQ ID NO: 2)
    (a) a VH CDR1 of
GYTFTNY;
and/or (SEQ ID NO: 7)
    (b) a VH CDR2 of
TYTG;
and/or (SEQ ID NO: 12)
    (c) a VH CDR3 of
STVVSRYFD;
``` and
(ii) the VL comprises:

```
                              (SEQ ID NO: 16)
    (a) a VL CDR1 of
SQDVGDA;
and/or (SEQ ID NO: 20)
    (b) a VL CDR2 of
WAS;
and/or (SEQ ID NO: 23)
    (c) a VL CDR3 of
YRSYPL.
```

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein (i) the VH comprises:

(a) a VH CDR1 of
GYTFTNYGMN; (SEQ ID NO: 3)
and/or (b) a VH CDR2 of
WINTYTGEPT; (SEQ ID NO: 8)
and/or (c) a VH CDR3 of
KSTVVSRYFDV; (SEQ ID NO: 11)

and
(ii) the VL comprises:

(a) a VL CDR1 of
KASQDVGDAVT; (SEQ ID NO: 15)
and/or (b) a VL CDR2 of
WASTRHT; (SEQ ID NO: 19)
and/or (c) a VL CDR3 of
QQYRSYPLT. (SEQ ID NO: 22)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

(a) a VH CDR1 of
TNYGMN; (SEQ ID NO: 4)
and/or (b) a VH CDR2 of
WMGWINTYTGEPT; (SEQ ID NO: 9)
and/or (c) a VH CDR3 of
ARKSTVVSRYFD; (SEQ ID NO: 13)

and
(ii) the VL comprises:

(a) a VL CDR1 of
GDAVTWC; (SEQ ID NO: 17)
and/or (b) a VL CDR2 of
LLIYWASTRH; (SEQ ID NO: 21)
and/or (c) a VL CDR3 of
QQYRSYPL. (SEQ ID NO: 24)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

(a) a VH CDR1 of
GYTFTNYG; (SEQ ID NO: 5)
and/or (b) a VH CDR2 of
INTYTGEP; (SEQ ID NO: 10)
and/or (c) a VH CDR3 of
ARKSTVVSRYFDV; (SEQ ID NO: 14)

and
(ii) the VL comprises:

(a) a VL CDR1 of
QDVGDA; (SEQ ID NO: 18)
and/or (b) a VL CDR2 comprising, of
WAS; (SEQ ID NO: 20)
and/or (c) a VL CDR3 of
QQYRSYPLT. (SEQ ID NO: 22)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein
(i) the VH comprises:

(a) a VH CDR1 of
GYTFTNYGMN; (SEQ ID NO: 3)
and/or (b) a VH CDR2 of
WINTYTGEPTYADDFKG; (SEQ ID NO: 6)
and/or (c) a VH CDR3 of
KSTVVSRYFDV; (SEQ ID NO: 11)

and
(ii) the VL comprises:

(a) a VL CDR1 of
KASQDVGDAVT; (SEQ ID NO: 15)
and/or (b) a VL CDR2 of
WASTRHT; (SEQ ID NO: 19)
and/or -continued (c) a VL CDR3 of

QQYRSYPLT. (SEQ ID NO: 22)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein (i) the VH comprises:

(a) a VH CDR1 of

NYTFTDYSMH; (SEQ ID NO: 27)
and/or (b) a VH CDR2 of

WINTDTGEPT; (SEQ ID NO: 32)
and/or (c) a VH CDR3 of

WFGAMDY; (SEQ ID NO: 35)

and (ii) the VL comprises:

(a) a VL CDR1 of

KASQDVTNVVA (SEQ ID NO: 39)
and/or;

(b) a VL CDR2 of

SASYRYT; (SEQ ID NO: 43)
and/or (c) a VL CDR3 of

QQYYRTPRT. (SEQ ID NO: 46)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein (i) the VH comprises:

(a) a VH CDR1 of

TDYSMH; (SEQ ID NO: 28)
and/or (b) a VH CDR2 of

WVGWINTDTGEPT; (SEQ ID NO: 33)
and/or (c) a VH CDR3 of

ARWFGAMD; (SEQ ID NO: 37)

and (ii) the VL comprises:

(a) a VL CDR1 of

TNVVAWY; (SEQ ID NO: 41)
and/or (b) a VL CDR2 of

LLIYSASYRY; (SEQ ID NO: 45)
and/or (c) a VL CDR3 of

QQYYRTPR. (SEQ ID NO: 48)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein (i) the VH comprises:

(a) a VH CDR1 of

NYTFTDYS; (SEQ ID NO: 29)
and/or (b) a VH CDR2 of

INTDTGEP; (SEQ ID NO: 34)
and/or (c) a VH CDR3 of

ARWFGAMDY; (SEQ ID NO: 38)

and (ii) the VL comprises:

(a) a VL CDR1 of

QDVTNV; (SEQ ID NO: 42)
and/or (b) a VL CDR2 of

SAS; (SEQ ID NO: 44)
and/or (c) a VL CDR3 of

QQYYRTPRT. (SEQ ID NO: 46)

In another embodiment, an anti-MERTK antibody or antigen-binding fragment thereof, which specifically binds to MERTK (e.g., human MERTK, or both human and mouse MERTK) and agonizes MERTK signaling of endothelial cells, comprises a heavy chain variable region (VH) and a light chain variable region (VL), wherein (i) the VH comprises:

(a) a VH CDR1 of

NYTFTDYSMH; (SEQ ID NO: 27)
and/or (b) a VH CDR2 of

WINTDTGEPTYADDFKG; (SEQ ID NO: 30)

and/or (c) a VH CDR3 of

WFGAMDY; (SEQ ID NO: 35)

and (ii) the VL comprises:

(a) a VL CDR1 of

KASQDVTNVVA; (SEQ ID NO: 39)
and/or (b) a VL CDR2 of

SASYRYT; (SEQ ID NO: 43)
and/or (c) a VL CDR3 of

QQYYRTPRT. (SEQ ID NO: 46)

In specific embodiments, the VH comprises two or all three of the VH CDRs above and/or the VL comprises two or all three of the VL CDRs above. In certain embodiments, the VH comprises a VH CDR1 of one of the antibodies in Table 1 or Table 3. In some embodiments, the VH comprises a VH CDR2 of one of the antibodies in Table 1 or Table 3. In certain embodiments, the VH comprises a VH CDR3 of one of the antibodies in Table 1 or Table 3. In some embodiments, the VL comprises a VL CDR1 of one of the antibodies in Table 2 or Table 4. In some embodiments, the VL comprises a VL CDR2 of one of the antibodies in Table 2 or Table 4. In certain embodiments, the VL comprises a VL CDR3 of one of the antibodies in Table 2 or Table 4. In some embodiments, the VH comprises a VH CDR1, a VH CDR2, and a VH CDR3 of the antibody M6 (Table 1). In certain embodiments, the VH comprises a VH CDR1, a VH CDR2, and a VH CDR3 of the antibody M19 (Table 3). In certain embodiments, the VL comprises a VL CDR1, a VL CDR2, and a VL CDR3 of the antibody M6 (Table 2). In certain embodiments, the VL comprises a VL CDR1, a VL CDR2, and a VL CDR3 of the VL CDRs of the antibody M19 (Table 4). In some embodiments, an anti-MERTK antibody or antigen-binding fragment thereof comprises a VH and a VL, wherein the VH comprises a VH CDR1, a VH CDR2, and a VH CDR3 of the antibody M19 (Table 3) and VL comprise a VL CDR1, a VL CDR2, and a VL CDR3 of the VL CDRs of the antibody M19 (Table 4). In some embodiments, an anti-MERTK antibody or antigen-binding fragment thereof comprises a VH and a VL, wherein the VH comprises a VH CDR1, a VH CDR2, and a VH CDR3 of the antibody M6 (Table 1) and VL comprise a VL CDR1, a VL CDR2, and a VL CDR3 of the VL CDRs of the antibody M6 (Table 2).

In a specific embodiment, an anti-MERTK antibody described herein, or an antigen-binding fragment thereof, which specifically binds to MERTK (e.g., human MERTK, or both human and mouse MERTK) and agonizes MERTK signaling of endothelial cells, comprises a heavy chain variable region sequence comprising the amino acid sequence of SEQ ID NO: 49 (Table 5) (e.g., the VH of antibody M6). In another specific embodiment, an antibody described herein, or an antigen-binding fragment thereof, which specifically binds to MERTK (e.g., human MERTK, or both human and mouse MERTK) and agonizes MERTK signaling of endothelial cells, comprises a heavy chain variable region sequence comprising the amino acid sequence of SEQ ID NO: 51 (Table 6) (e.g., the VH of antibody M19).

In another embodiment, an antibody described herein, or an antigen-binding fragment thereof, which specifically binds to MERTK (e.g., human MERTK, or both human and mouse MERTK) and agonizes MERTK signaling of endothelial cells, comprises a light chain variable region sequence comprising the amino acid sequence of SEQ ID NO: 50 (Table 5) (e.g., the VL of antibody M6). In another specific embodiment, an antibody described herein, or an antigen-binding fragment thereof, which specifically binds to MERTK (e.g., human MERTK, or both human and mouse MERTK) and agonizes MERTK signaling of endothelial cells, comprises a light chain variable region sequence comprising the amino acid sequence of SEQ ID NO: 52 (Table 6) (e.g., the VL of antibody M19).

In one specific embodiment, an antibody described herein, or an antigen-binding fragment thereof, which specifically binds to MERTK (e.g., human MERTK, or both human and mouse MERTK) and agonizes MERTK signaling of endothelial cells, comprises (a) a heavy chain variable region comprising the amino acid sequence of SEQ ID NO: 49; and (b) a light chain variable region comprising the amino acid sequence of SEQ ID NO: 50 (e.g., the VH and VL of antibody M6). In another specific embodiment, an antibody described herein, or an antigen-binding fragment thereof, which specifically binds to MERTK (e.g., human MERTK, or both human and mouse MERTK) and agonizes MERTK signaling of endothelial cells, comprises (a) a heavy chain variable region comprising the amino acid sequence of SEQ ID NO: 50; and (b) a light chain variable region comprising the amino acid sequence of SEQ ID NO: 52 (e.g., the VH and VL of antibody M19).

In a preferred embodiment, the antibody is a humanized antibody, or a humanized antigen-binding fragment thereof, that specifically binds to MERTK (e.g., human MERTK, or both human and mouse MERTK) and comprises: (A) a VH CDR1 of SEQ ID NO: 1, a VH CDR2 of SEQ ID NO: 6, a VH CDR3 of SEQ ID NO: 11, a VL CDR1 of SEQ ID NO: 15, a VL CDR2 of SEQ ID NO: 19, and a VL CDR3 of SEQ ID NO: 22; (B) a VH CDR1 of SEQ ID NO: 2, a VH CDR2 of SEQ ID NO: 7, a VH CDR3 of SEQ ID NO: 12, a VL CDR1 of SEQ ID NO: 16, a VL CDR2 of SEQ ID NO: 20, and a VL CDR3 of SEQ ID NO: 23; (C) a VH CDR1 of SEQ ID NO: 3, a VH CDR2 of SEQ ID NO: 8, a VH CDR3 of SEQ ID NO: 11, a VL CDR1 of SEQ ID NO: 15, a VL CDR2 of SEQ ID NO: 19, and a VL CDR3 of SEQ ID NO: 22; (D) a VH CDR1 of SEQ ID NO: 4, a VH CDR2 of SEQ ID NO: 9, a VH CDR3 of SEQ ID NO: 13, a VL CDR1 of SEQ ID NO: 17, a VL CDR2 of SEQ ID NO: 21, and a VL CDR3 of SEQ ID NO: 24; (E) a VH CDR1 of SEQ ID NO: 5, a VH CDR2 of SEQ ID NO: 10, a VH CDR3 of SEQ ID NO: 14, a VL CDR1 of SEQ ID NO: 18, a VL CDR2 of SEQ ID NO: 20, and a VL CDR3 of SEQ ID NO: 22; or (F) a VH CDR1 of SEQ ID NO: 3, a VH CDR2 of SEQ ID NO: 6, a VH CDR3 of SEQ ID NO: 11, a VL CDR1 of SEQ ID NO: 15, a VL CDR2 of SEQ ID NO: 19, and a VL CDR3 of SEQ ID NO: 22.

In certain aspects, an antibody described herein may be described by its VH domain alone, or its VL domain alone, or by its three VH CDRs alone, or its three VL CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson T et al., (1991) Nature 352: 624-628, which is incorporated herein by reference in its entirety, describing methods of producing antibodies that bind a specific antigen by using a specific VH domain (or VL domain) and screening a library for the complementary variable domains. See also, Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as immunospecific binding to MERTK (e.g., human MERTK, or both human and mouse MERTK) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, six or more amino acids, so long as immunospecific binding to MERTK (e.g., human MERTK, or both human and mouse MERTK) is maintained (e.g., substantially maintained, for example, at least 50%, at least 60%, at least 70%, at least 80%, at least 90%, at least 95%). In another embodiment, the amino terminus and/or the carboxy terminus of a VH CDR1, VH CDR2, VH CDR3, VL CDR1, VL CDR2, and/or VL CDR3 described herein may be extended or shortened by one, two, three, four, five or more amino acids compared to one or more of the CDRs described herein so long as immunospecific binding to MERTK (e.g., human MERTK, or both human and mouse MERTK) is maintained (e.g., substantially maintained, for example, at least 50%, at least 60%, at least 70%, at least 80%, at least 90%, at least 95%). As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens. Any method known in the art can be used to ascertain whether immunospecific binding to MERTK (e.g., human MERTK, or both human and mouse MERTK) is maintained, for example, the binding assays and conditions described in Example 4 and Example 7 (Section 6) provided herein, infra.

In specific aspects, described herein is an anti-MERTK antibody or antigen-binding fragment thereof comprising an antibody heavy chain and/or light chain, e.g., a heavy chain alone, a light chain alone, or both a heavy chain and a light chain. With respect to the light chain, in a specific embodiment, the light chain of an anti-MERTK antibody or an antigen-binding fragment thereof described herein is a kappa light chain. In another specific embodiment, the light chain of an anti-MERTK antibody or an antigen-binding fragment thereof described herein is a lambda light chain. In yet another specific embodiment, the light chain of an anti-MERTK antibody or an antigen-binding fragment thereof described herein is a human kappa light chain or a human lambda light chain.

In a particular embodiment, an anti-MERTK antibody or an antigen-binding fragment thereof described herein, which immunospecifically binds to MERTK (e.g., human MERTK, or both human and mouse MERTK) comprises a light chain wherein the amino acid sequence of the variable region of the light chain comprises a VL CDR1, VL CDR2, and VL CDR3 having the amino acid sequences of antibody M6 or antibody M19 VL CDRs (i.e., those listed in Table 2 and Table 4), and wherein the constant region of the light chain comprises the amino acid sequence of a kappa light chain constant region. In another particular embodiment, an anti-MERTK antibody or an antigen-binding fragment thereof described herein, which immunospecifically binds to MERTK (e.g., human MERTK, or both human and mouse MERTK) comprises a light chain wherein the amino acid sequence of the variable region of the light chain comprises the amino acid sequence of SEQ ID NO: 50 or SEQ ID NO: 52, and wherein the constant region of the light chain comprises the amino acid sequence of a kappa light chain constant region. As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In specific embodiments, the antibody or antigen-binding fragment thereof agonizes MERTK signaling.

In another particular embodiment, an anti-MERTK antibody or an antigen-binding fragment thereof described herein, which immunospecifically binds to MERTK (e.g., human MERTK, or both human and mouse MERTK) comprises a light chain wherein the amino acid sequence of the variable region of the light chain comprises a VL CDR1, VL CDR2, and VL CDR3 having the amino acid sequences of antibody M6 or antibody M19 VL CDRs (i.e., those listed in Table 2 and Table 4), and wherein the constant region of the light chain comprises the amino acid sequence of a lambda light chain constant region. In another particular embodiment, an anti-MERTK antibody or an antigen-binding fragment thereof described herein, which immunospecifically binds to MERTK (e.g., human MERTK, or both human and mouse MERTK) comprises a light chain wherein the amino acid sequence of the variable region of the light chain comprise the amino acid sequence of SEQ ID NO: 50 or SEQ ID NO: 52, and wherein the constant region of the light chain comprises the amino acid sequence of a lambda light chain constant region. In specific embodiments, the antibody or antigen-binding fragment thereof agonizes MERTK signaling.

In another particular embodiment, an anti-MERTK antibody or an antigen-binding fragment thereof described herein, which immunospecifically binds to MERTK (e.g., human MERTK, or both human and mouse MERTK) comprises a light chain wherein the amino acid sequence of the variable region of the light chain comprises a VL CDR1, VL CDR2, and VL CDR3 having the amino acid sequences of antibody M6 or antibody M19 VL CDRs (i.e., those listed in Table 2 and Table 4), and wherein the constant region of the light chain comprises the amino acid sequence of a human kappa or lambda light chain constant region. In a specific embodiment, an anti-MERTK antibody or an antigen-binding fragment thereof described herein, which immunospecifically binds to MERTK (e.g., human MERTK, or both human and mouse MERTK) comprises a light chain wherein the amino acid of the variable region of the light chain comprises the amino acid sequence of SEQ ID NO: 50 or SEQ ID NO: 52, and wherein the constant region of the light chain comprises the amino acid sequence of a human kappa or lambda light chain constant region. In specific embodiments, the antibody or antigen-binding fragment thereof agonizes MERTK signaling. Non-limiting examples of human constant region sequences have been described in the art, e.g., see Kabat E A et al., (1991).

With respect to the heavy chain, in a specific embodiment, the heavy chain of an anti-MERTK antibody or an antigen-binding fragment thereof described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain.

In a particular embodiment, an anti-MERTK antibody or an antigen-binding fragment thereof described herein, which immunospecifically binds to MERTK (e.g., human MERTK, or both human and mouse MERTK) comprises a heavy chain wherein the amino acid sequence of the variable region of the heavy chain comprises a VH CDR1, VH CDR2, and VH CDR3 having the amino acid sequences of antibody M6 or antibody M19 VH CDRs (i.e., those listed in Table 1 and Table 3), and wherein the constant region of the heavy chain comprises the amino acid sequence of a human gamma (γ) heavy chain constant region. In another particular embodiment, an anti-MERTK antibody or an antigen-binding fragment thereof described herein, which immunospecifically binds to MERTK (e.g., human MERTK, or both human and mouse MERTK) comprises a heavy chain wherein the amino acid sequence of the variable region of the heavy chain comprises the amino acid sequence of SEQ ID NO: 49 or SEQ ID NO: 51, and wherein the constant region of the heavy chain comprises the amino acid sequence of a human gamma (γ) heavy chain constant region. In specific embodiments, the antibody or antigen-binding fragment thereof agonizes MERTK signaling.

In a specific embodiment, an anti-MERTK antibody or an antigen-binding fragment thereof described herein, which immunospecifically binds to MERTK (e.g., human MERTK, or both human and mouse MERTK) comprises a heavy chain wherein the amino acid sequence of the variable region of the heavy chain comprises a VH CDR1, VH CDR2, and VH CDR3 having the amino acid sequences of antibody M6 or antibody M19 VH CDRs (i.e., those listed in Table 1 and Table 3), and wherein the constant region of the heavy chain comprises the amino acid of a human heavy chain described herein or known in the art. In a specific embodiment, an anti-MERTK antibody or an antigen-binding fragment thereof described herein, which specifically binds to MERTK (e.g., human MERTK, or both human and mouse MERTK) comprises a heavy chain wherein the amino acid sequence of the variable region of the heavy chain comprises the amino acid sequence of SEQ ID NO: 49 or SEQ ID NO: 51, and wherein the constant region of the heavy chain comprises the amino acid sequence of a human heavy chain described herein or known in the art. In specific embodiments, the antibody or antigen-binding fragment thereof agonizes MERTK signaling. Non-limiting examples of human constant region sequences have been described in the art, e.g., see Kabat E A et al., (1991) supra.

In a specific embodiment, an anti-MERTK antibody or antigen-binding fragment thereof described herein, which immunospecifically binds to MERTK (e.g., human MERTK, or both human and mouse MERTK) comprises a heavy chain variable region (VH) and a light chain variable region (VL) comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an anti-MERTK antibody or antigen-binding fragment thereof described herein, which immunospecifically binds to MERTK (e.g., human MERTK, or both human and mouse MERTK) comprises a VH and a VL comprising any amino acid sequences described herein, and wherein the constant regions comprise the amino acid sequences of the constant regions of an IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_2a$ and $IgG_2b$) of immunoglobulin molecule. In a particular embodiment, the constant regions comprise the amino acid sequences of the constant regions of a human IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_2a$ and $IgG_2b$) of immunoglobulin molecule.

In certain embodiments, one, two or more mutations (e.g., amino acid substitutions) are introduced into the Fc region of an anti-MERTK antibody or an antigen-binding fragment thereof described herein to alter one or more functional properties of the antibody.

In some embodiments, one, two or more mutations (e.g., amino acid substitutions) are introduced into the Fc region of an anti-MERTK antibody or an antigen-binding fragment thereof described herein (e.g., CH2 domain (residues 231-340 of human $IgG_1$) and/or CH3 domain (residues 341-447 of human $IgG_1$) and/or the hinge region, with numbering according to the Kabat numbering system (e.g., the EU index in Kabat)) to increase or decrease the affinity of the antibody or an antigen-binding fragment thereof for an Fc receptor (e.g., an activated Fc receptor) on the surface of an effector cell. Mutations in the Fc region of an anti-MERTK antibody or antigen-binding fragment thereof that decrease or increase the affinity of an antibody for an Fc receptor and techniques for introducing such mutations into the Fc receptor or fragment thereof are known to one of skill in the art. Examples of mutations in the Fc receptor of an anti-MERTK antibody or antigen-binding fragment thereof that can be made to alter the affinity of the antibody or an antigen-binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, the antibody or antigen-binding fragment thereof comprises a glycosylated constant region. In some embodiments, the antibody or antigen-binding fragment thereof comprises a non-glycosylated constant region. Antibodies with reduced fucose content have been reported to have an increased affinity for Fc receptors, such as, e.g., FcγRIIIa. Accordingly, in certain embodiments, the antibodies or antigen-binding fragments thereof described herein have reduced fucose content or no fucose content. Such antibodies or antigen-binding fragments thereof can be produced using techniques known to one skilled in the art. For example, the antibodies or antigen-binding fragments thereof can be expressed in cells deficient or lacking the ability of fucosylation. In a specific example, cell lines with a knockout of both alleles of a1,6-fucosyltransferase can be used to produce antibodies with reduced fucose content. The Potelligent® system (Lonza) is an example of such a system that can be used to produce antibodies or antigen-binding fragments thereof with reduced fucose content. Alternatively, antibodies or antigen-binding fragments with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies or antigen-binding fragments thereof with no fucose content or reduced fucose content.

In another particular embodiment, an anti-MERTK antibody or an antigen-binding fragment thereof described herein, which immunospecifically binds to MERTK (e.g., human MERTK, or both human and mouse MERTK) and agonizes MERTK signaling of endothelial cells, comprises a heavy chain and/or a light chain, wherein (i) the heavy chain comprises (a) a variable region comprising a VH CDR1, VH CDR2, and VH CDR3 having the amino acid sequences of antibody M6 or antibody M19 VH CDRs (i.e., those listed in Table 1 and Table 3) and (b) comprises a constant heavy chain domain comprising the amino acid sequence of the constant domain of a human IgG heavy chain; and/or (ii) the light chain comprises (a) a variable region comprising a VL CDR1, VL CDR2, and VL CDR3 having the amino acid sequences of antibody M6 or antibody M19 VL CDRs (i.e., those listed in Table 2 and Table 4) and (b) a constant light chain domain comprising the amino acid sequence of the constant domain of a human IgG.

In another particular embodiment, an anti-MERTK antibody or an antigen-binding fragment thereof described herein, which immunospecifically binds to MERTK (e.g., human MERTK, or both human and mouse MERTK) and agonizes MERTK signaling of endothelial cells, comprises a heavy chain and/or a light chain, wherein (i) the heavy chain comprises (a) a variable region comprising the amino acid sequence of SEQ ID NO: 49 or SEQ ID NO: 51 and (b) a constant heavy chain domain comprising the amino acid sequence of the constant domain of a human IgG; and/or (ii) the light chain comprises a variable region comprising the amino acid sequence of SEQ ID NO: 50 or SEQ ID NO: 52 (b) a constant light chain domain comprising the amino acid sequence of the constant domain of a human kappa light chain.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises a VH having at least 80%, at least 85%, at least 90%, at least 95%, or at least 98% sequence identity to the amino acid sequence of the VH of SEQ ID NO: 49 or SEQ ID NO: 51. In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises a VH domain having at least 80%, at least 85%, at least 90%, at least 95%, or at least 98% sequence identity to the amino acid sequence of the VH of SEQ ID NO: 49 or SEQ ID NO: 51, wherein the antibody or antigen-binding fragment comprises CDRs (e.g., VH CDRs and/or VL CDRs) that are identical to the CDRs (e.g., VH CDRs and/or VL CDRs) set forth in Tables 1 to 4.

In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises a VL having at least 80%, at least 85%, at least 90%, at least 95%, or at least 98% sequence identity to the amino acid sequence of the VL of SEQ ID NO: 50 or SEQ ID NO: 52. In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises a VL having at least 80%, at least 85%, at least 90%, at least 95%, or at least 98% sequence identity to the amino acid sequence of the VL of SEQ ID NO: 50 or SEQ ID NO: 52, wherein the antibody or antigen-binding fragment comprises CDRs (e.g., VH CDRs and/or VL CDRs) that are identical to the CDRs (e.g., VH CDRs and/or VL CDRs) set forth in Tables 1 to 4.

In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises: (i) a VH domain having at least 80%, at least 85%, at least 90%, at least 95%, or at least 98% sequence identity to the amino acid sequence of the VH domain of SEQ ID NO: 49 or SEQ ID NO: 51; and (ii) a VL domain having at least 80%, at least 85%, at least 90%, at least 95%, or at least 98% sequence identity to the amino acid sequence of the VL domain of SEQ ID NO: 50 or SEQ ID NO: 52. In certain embodiments, an anti-MERTK antibody or antigen-binding fragment thereof, which immunospecifically binds to MERTK (e.g., human MERTK, or both human and mouse MERTK) and agonizes MERTK signaling of endothelial cells, comprises: (i) a VH domain having at least 80%, at least 85%, at least 90%, at least 95%, or at least 98% sequence identity to the amino acid sequence of the VH domain of SEQ ID NO: 49 or SEQ ID NO: 51; and (ii) a VL domain having at least 80%, at least 85%, at least 90%, at least 95%, or at least 98% sequence identity to the amino acid sequence of the VL domain of SEQ ID NO: 50 or SEQ ID NO: 52, wherein the antibody or antigen-binding fragment comprises CDRs (e.g., VH CDRs and/or VL CDRs) that are identical to the CDRs (e.g., VH CDRs and/or VL CDRs) set forth in Tables 1 to 4.

In another aspect, described herein are antibodies that bind the same or an overlapping epitope of MERTK (e.g., an epitope of human MERTK, or both human and mouse MERTK) as an antibody described herein (e.g., antibody M6 or M19). As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope of an antibody can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) and Cunningham B C & Wells J A (1989) for a description of mutagenesis techniques, including alanine scanning mutagenesis techniques. In addition, antibodies that recognize and bind to the same or overlapping epitopes of MERTK (e.g., human MERTK, or both human and mouse MERTK) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as MERTK. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., MERTK such as human MERTK) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g., antibody M6 or M19).

In another aspect, described herein are antibodies that compete (e.g., in a dose dependent manner) for binding to MERTK (e.g., human MERTK, or both human and mouse MERTK) with an antibody described herein (e.g., M6 or M19), and agonizes MERTK signaling of endothelial cells, as determined using assays known to one of skill in the art or described herein (e.g., ELISA competitive assays or surface plasmon resonance). In another aspect, described herein are antibodies that competitively inhibit (e.g., in a dose dependent manner) an antibody described herein (e.g., M6 or M19) from binding to MERTK (e.g., human MERTK, or both human and mouse MERTK), as determined using assays known to one of skill in the art or described herein (e.g., ELISA competitive assays, or suspension array or surface plasmon resonance).

In certain embodiments, described herein is an antibody that competes with an antibody described herein for binding to MERTK (e.g., human MERTK, or both human and mouse MERTK) to the same extent that the antibody described herein self-competes for binding to MERTK (e.g., human MERTK, or both human and mouse MERTK). In certain embodiments, described herein is a first antibody that competes with an antibody described herein for binding to MERTK (e.g., human MERTK, or both human and mouse MERTK), wherein the competition is exhibited as reduced binding of the first antibody to MERTK by more than 80% (e.g., 85%, 90%, 95%, or 98%, or between 80% to 85%, 80% to 90%, 85% to 90%, or 85% to 95%).

In specific aspects, described herein is an antibody which competes (e.g., in a dose dependent manner) for specific binding to MERTK (e.g., human MERTK, or both human and mouse MERTK), with an antibody comprising a VH domain having the amino acid sequence of SEQ ID NO: 49 or SEQ ID NO: 51, and a VL domain having the amino acid sequence of SEQ ID NO: 50 or SEQ ID NO: 52.

In specific aspects, described herein is an antibody which competes (e.g., in a dose dependent manner) for specific binding to MERTK (e.g., human MERTK, or both human and mouse MERTK), with an antibody comprising (i) a VH domain comprising a VH CDR1, VH CDR2, and VH CDR3 having the amino acid sequences of the CDRs of an antibody listed in Table 1 or Table 3; and (ii) a VL domain comprising a VL CDR1, VL CDR2, and VL CDR3 having the amino acid sequences of the VL CDRs of an antibody listed in Table 2 or Table 4.

In a particular embodiment, described herein is an antibody that competes (e.g., in a dose-dependent manner), for specific binding to MERTK (e.g., human MERTK, or both human and mouse MERTK), with an antibody comprising the VH and VL CDRs of antibody M6 (Table 1 and Table 2).

In a particular embodiment, described herein is an antibody that competes (e.g., in a dose-dependent manner), for specific binding to MERTK (e.g., human MERTK, or both human and mouse MERTK), with an antibody comprising the VH and VL CDRs of antibody M19 (Table 3 and Table 4).

In another specific embodiment, an anti-MERTK antibody or an antigen-binding fragment thereof described herein immunospecifically binds to the same or an overlapping epitope of antibody comprising (i) a VH domain comprising a VH CDR1, VH CDR2, and VH CDR3 having the amino acid sequences of the CDRs of antibody listed in Table 1 or Table 3, and (ii) a VL domain comprising a VL CDR1, VL CDR2, and VL CDR3 having the amino acid sequences of the CDRs of antibody listed in Table 2 or Table 4.

In a specific embodiment, an anti-MERTK antibody or an antigen-binding fragment thereof described herein immunospecifically binds to the same or an overlapping epitope of antibody M6, comprising a VH domain having an amino acid sequence of SEQ ID NO: 49, and a VL domain having an amino acid sequence of SEQ ID NO: 50. In another specific embodiment, an anti-MERTK antibody or an antigen-binding fragment thereof described herein immunospecifically binds to the same or an overlapping epitope of antibody M19, comprising a VH domain having an amino acid sequence of SEQ ID NO: 51, and a VL domain having an amino acid sequence of SEQ ID NO: 52. Assays known to one of skill in the art or described herein (e.g., X-ray crystallography, ELISA assays, etc.) can be used to determine if two antibodies bind to the same epitope.

Affinity can be measured and/or expressed in a number of ways known in the art, including, but not limited to, equilibrium dissociation constant ($K_D$), and equilibrium association constant ($K_A$). The $K_D$ can be determined by techniques known to one of ordinary skill in the art, such as biolayer interferometry. In a specific embodiment, the $K_D$ is determined as set forth in Example 4 or Example 7 in Section 6, infra.

In certain embodiments, an anti-MERTK antibody or an antigen-binding fragment thereof described herein, an anti-MERTK antibody or antigen-binding fragment thereof that competes with an antibody described herein for binding to MERTK, or an anti-MERTK antibody or antigen-binding fragment thereof that binds to the same or an overlapping epitope of an antibody described herein, binds to MERTK (e.g., human MERTK, or both human and mouse MERTK) with a $K_D$ of less than 7 nM, 6 nM, 5 nM, 4.5 nM, 4 nM, 3.5 nM, 3 nM, 2.5 nM, 2 nM, 1.5 nM, 1 nM, 0.75 nM, 0.5 nM, 0.25 nM, 0.1 nM, 0.05 nM, 0.025 nM, 0.01 nM, or 0.005 nM. In some embodiments, an anti-MERTK antibody or an antigen-binding fragment thereof described herein, an anti-MERTK antibody or antigen-binding fragment thereof that competes with an antibody described herein for binding to MERTK, or an anti-MERTK antibody or antigen-binding fragment thereof that binds to the same or an overlapping epitope of an antibody described herein, binds to MERTK (e.g., human MERTK, or both human and mouse MERTK) with a $K_D$ of about 7 nM, 6 nM, 5 nM, 4.5 nM, 4 nM, 3.5 nM, 3 nM, 2.5 nM, 2 nM, 1.5 nM, 1 nM, 0.75 nM, 0.5 nM, 0.25 nM, 0.1 nM, 0.05 nM, 0.025 nM, 0.01 nM, or 0.005 nM. In some embodiments, an anti-MERTK antibody or an antigen-binding fragment thereof described herein, an anti-MERTK antibody or antigen-binding fragment thereof that competes with an antibody described herein for binding to MERTK, or an anti-MERTK antibody or antigen-binding fragment thereof that binds to the same or an overlapping epitope of an antibody described herein, binds to MERTK (e.g., human MERTK, or both human and mouse MERTK) with a $K_D$ of about 3 pM to 400 pM. In a specific embodiment, an anti-MERTK antibody or an antigen-binding fragment thereof described herein binds to MERTK (e.g., human MERTK, or both human and mouse MERTK) with a $K_D$ of about 0.3 nM. In another specific embodiment, an anti-MERTK antibody or an antigen-binding fragment thereof described herein binds to MERTK (e.g., human MERTK, or both human and mouse MERTK) with a $K_D$ of about 4.6 pM. As used herein, the terms "about" when used to modify a numeric value or numeric range, indicate that deviations of 5% to 10% above and 5% to 10% below the value or range remain within the intended meaning of the recited value or range.

In certain embodiments, the epitope of an antibody described herein is used as an immunogen to produce antibodies. See, e.g., Section 5.2 infra for methods for producing antibodies.

In specific embodiments, the anti-MERTK antibody or an antigen-binding fragment thereof described herein is engineered or modified by a method known in the art to facilitate conjugation with the drug moiety(ies), in particular to facilitate site-specific conjugation with the drug moiety(ies), for example, by a method described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; or Olivier K J and Hurvitz S A ed., (2016) Antibody-Drug Conjugates: Fundamentals, Drug Development, and Clinical, Wiley. Non-limiting exemplary methods that can be used (see Beck A et al., (2017) Nat Rev Drug Discov 16: 315-337) to engineer or modify an anti-MERTK antibody or an antigen-binding fragment thereof to facilitate conjugation with the drug moiety(ies) include adding one or more additional cysteines or selenocysteines, unnatural amino acid engineering, adding one or more amino acid tags recognizable by certain enzymes that can assist with the conjugation, glycan remodeling, adding an amino-terminal serine, and native cysteine bridging.

5.1.2. Functional Characteristics of the Antibody Moiety

In some aspects, an anti-MERTK antibody or an antigen-binding fragment thereof described herein, which immunospecifically binds to MERTK (e.g., human MERTK, or both human and mouse MERTK) and agonizes MERTK signaling of endothelial cells, increases MERTK (e.g., human MERTK, or both human and mouse MERTK) activity on endothelial cells at least about 2 fold, 3 fold, 4 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold. The MERTK activity can be assessed by methods described herein or known to one of skill in the art, e.g., by measuring the amount of MERTK phosphorylation. In another specific embodiment, the increase in MERTK activity as measured by an increase in phosphorylation of MERTK is at least 3 fold, 4 fold, 5 fold, 6 fold, 7 fold, 8 fold, 9 fold, 10 fold, 15 fold, 20 fold, or 30 fold, relative to MERTK activity (e.g., human MERTK, or both human and mouse MERTK activity) on endothelial cells without any antibody or with an unrelated antibody (e.g., an antibody that does not immunospecifically bind to MERTK). In specific embodiments, the increase in MERTK activity is at least 50%, 60%, 70%, 80%, 90%, or 100%. In specific embodiments, an increase in MERTK activity is assessed as described in Example 3, infra.

In certain embodiments, an anti-MERTK antibody or antigen-binding fragment thereof described herein, which immunospecifically binds to MERTK (e.g., human MERTK, or both human and mouse MERTK) and agonizes MERTK signaling of endothelial cells competes with Gas-6 (e.g., human Gas-6) for binding to MERTK. In some embodiments, the antibody or antigen-binding fragment thereof described herein inhibits (e.g., completely inhibits or only partially inhibits) Gas-6 from binding to MERTK (e.g., human MERTK, or both human and mouse MERTK). In some embodiments, an anti-MERTK antibody or an antigen-binding fragment thereof described herein, which immunospecifically binds to MERTK (e.g., human MERTK, or both human and mouse MERTK) and agonizes MERTK signaling of endothelial cells inhibits the binding of Gas-6 (e.g., human or mouse Gas-6) to MERTK (e.g., human MERTK, or both human and mouse MERTK) on endothelial cells by more than 85%, 80%, 75%, 70%, 65%, 60%, 55%, 50%, 45%, 40%, 35%, 30%, 25%, 20% or 10% as assessed by an assay known to one of skill in the art or described herein. In a specific embodiment, the assay that is used to assess inhibition of binding of Gas-6 (e.g., human Gas-6) to MERTK (e.g., human MERTK, or both human and mouse MERTK) in the presence of an anti-MERTK antibody or antigen-binding fragment thereof described herein is antibody capture ELISA as described in Example 1, infra.

In a specific embodiment, the level of MERTK phosphorylation in endothelial cells is measured by phospho-MERTK-specific Western blotting as described in Example 3, infra.

In specific embodiments, an anti-MERTK antibody or an antigen-binding fragment thereof described herein, which promotes (i.e., increases) the level of MERTK phosphorylation on endothelial cells, does not promote (i.e., increase) MERTK phosphorylation on cancer cells (e.g., breast cancer cells) in vitro. In a specific embodiment, the level of MERTK phosphorylation in cancer cells is measured by phospho-MERTK-specific Western blotting as described in Example 3, infra.

In certain embodiments, an anti-MERTK antibody or an antigen-binding fragment thereof described herein, which immunospecifically binds to MERTK (e.g., human MERTK, or both human and mouse MERTK) and agonizes MERTK signaling of endothelial cells, inhibits the migration of MERTK-expressing endothelial cells in vitro in the presence of cancer cells (e.g., breast cancer cells). In some specific embodiments, the migration of the endothelial cells is inhibited by at least 10%, 20%, 30%, 35%, 40%, 50%, or 60% as assessed by methods described herein and/or known to one of skill in the art. In some specific embodiments, the migration of the endothelial cells is inhibited by at least 40%, 45%, 50%, 55%, or 60% as assessed by methods described herein and/or known to one of skill in the art. The extent of migration can be assessed by methods described herein and/or known to one of skill in the art. The inhibition can be relative to the extent of migration of the MERTK-expressing endothelial cells without any antibody or with an unrelated antibody (e.g., an antibody that does not immunospecifically bind to MERTK). In a specific embodiment, the assay that is used to assess endothelial cell migration is a transwell migration assay as described in Example 2, infra.

In particular embodiments, the antibody or antigen-binding fragment thereof described herein, which immunospecifically binds to MERTK (e.g., human MERTK, or both human and mouse MERTK) and agonizes MERTK signaling of endothelial cells, does not inhibit the migration of glioblastoma multiforme cell line A172 in an in vitro trans-well migration assay in the absence of endothelial cells.

In specific embodiments, an anti-MERTK antibody or an antigen-binding fragment thereof described herein, which immunospecifically binds to MERTK (e.g., human MERTK, or both human and mouse MERTK) and agonizes MERTK signaling of endothelial cells, inhibits angiogenesis within tumors. In some embodiments, the inhibition of angiogenesis is by at least 10%, 20%, 30%, 40%, 50%, 55, 60%, 65%, 70%, or 75%. In a specific embodiment, the inhibition of angiogenesis is at least 50%, 55%, 60%, 65%, or 70%. Inhibition of angiogenesis can be assessed by methods described herein and/or known to one of skill in the art. The inhibition can be relative to the level of angiogenesis without any antibody or with an unrelated antibody (e.g., an antibody that does not immunospecifically bind to MERTK). In a specific embodiment, the assay that is used to assess angiogenesis in vivo is as described in Example 6, infra.

In certain embodiments, an anti-MERTK antibody or an antigen-binding fragment thereof described herein, which immunospecifically binds to MERTK (e.g., human MERTK, or both human and mouse MERTK) and agonizes MERTK signaling of endothelial cells, inhibits tumor (e.g., human breast cancer tumor) progression. The inhibition of tumor progression by at least 10%, 20%, 30%, 40%, 50%, 60%, 70%, or 80%. Tumor progression can be assessed by methods described herein and/or known to one of skill in the art.

The tumor progression can be relative to the cancer status without any antibody or with an unrelated antibody (e.g., an antibody that does not immunospecifically bind to MERTK). In a specific embodiment, the assay that is used to assess tumor progression is a murine tumor transplantation model as described in Examples 5 and 8, infra.

5.2. Antibody Production

5.2.1. Producing and Screening Antibodies

Also described herein are methods of producing antibodies or antigen-binding fragments thereof that specifically bind to MERTK (e.g., human MERTK, or both human and mouse MERTK) and agonize MERTK signaling of endothelial cells.

The antibodies or antigen-binding fragments thereof described herein can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences that are encoded by DNA sequences that do not naturally exist within the antibody germline repertoire of an animal or mammal (e.g., human) in vivo. In a specific embodiment, an antibody described herein is made by a method comprising using human MERTK (SEQ ID NO: 57) or the extracellular domain thereof (SEQ ID NO: 58) as an immunogen.

In a certain aspect, described herein is a method of making an anti-MERTK antibody or antigen-binding fragment thereof which immunospecifically binds to MERTK (e.g., human MERTK, or both human and mouse MERTK) and agonizes MERTK signaling of endothelial cells comprising culturing a cell or host cell described herein. In a certain aspect, described herein is a method of making an anti-MERTK antibody or antigen-binding fragment thereof which immunospecifically binds to MERTK (e.g., human MERTK, or both human and mouse MERTK) and agonizes MERTK signaling of endothelial cells comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

The term "monoclonal antibody" as used herein is not limited to antibodies produced through hybridoma technology. Monoclonal antibodies can be prepared using a wide variety of techniques known in the art including the use of hybridoma, recombinant, and phage display technologies, or a combination thereof. For example, monoclonal antibodies can be produced recombinantly from host cells exogenously expressing an antibody described herein or a fragment thereof, for example, a light chain and/or heavy chain of such antibody. Methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra). For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, NY, 1981); and Kohler G & Milstein C (1975) Nature 256: 495. Methods for producing and screening for specific antibodies using hybridoma technology are routine and well known in the art. In some embodiments, mice (or other animals, such as rats, monkeys, donkeys, pigs, sheep, hamster, or dogs) can be immunized with an antigen (e.g., MERTK (e.g., human MERTK, or both human and mouse MERTK)) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, VA), to form hybridomas. Hybridomas are selected and cloned by limited dilution. The hybridoma cells thus prepared are seeded and grown in a suitable culture medium that preferably contains one or more substances that inhibit the growth or survival of the unfused, parental myeloma cells. Culture medium in which hybridoma cells are growing is assayed for production of monoclonal antibodies directed against MERTK (e.g., human MERTK, or both human and mouse MERTK). After hybridoma cells are identified that produce antibodies of the desired specificity, affinity, and/or activity, the clones may be subcloned, grown, and separated from the culture medium by standard methods (Goding J W (Ed), Monoclonal Antibodies: Principles and Practice, supra). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

In specific embodiments, disclosed herein are monoclonal antibodies that are produced by a single cell (e.g., hybridoma or host cell producing a recombinant antibody), wherein the antibody immunospecifically binds to MERTK (e.g., human MERTK, or both human and mouse MERTK) as determined, e.g., by ELISA or other antigen-binding or competitive binding assay known in the art or as described in Example 1 provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

Antibodies described herein include antibody fragments which recognize MERTK (e.g., human MERTK, or both human and mouse MERTK) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat.

Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that immunospecifically bind to a MERTK antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody described herein, which binds to the same or an overlapping epitope of MERTK (e.g., human MERTK, or both human and mouse MERTK) as a MERTK agonistic antibody described herein, is a human anti-MERTK antibody or antigen-binding fragment thereof. In particular embodiments, an antibody described herein, which competitively blocks (e.g., in a dose-dependent manner) any one of the antibodies described herein, (e.g., M6 or M19) from binding to MERTK (e.g., human MERTK, or both human and mouse MERTK), is a human anti-MERTK antibody or antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., MERTK). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to MERTK (e.g., human MERTK, or both human and mouse MERTK) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., MERTK (e.g., human MERTK, or both human and mouse MERTK)). Such methods are known and are described in the art, see, e.g., Shinmoto H et al., (2004) Cytotechnology 46: 19-23; Naganawa Y et al., (2005) Human Antibodies 14: 27-31.

In specific embodiments, the methods of producing antibodies or antigen-binding fragments thereof that specifically bind to MERTK (e.g., human MERTK, or both human and mouse MERTK) and agonize MERTK signaling of endothelial cells are as described in Example 1, infra.

In specific embodiments, the methods of screening and selecting antibodies or antigen-binding fragments thereof that specifically bind to MERTK (e.g., human MERTK, or both human and mouse MERTK) and agonize MERTK signaling of endothelial cells are as described in Example 1, infra.

Once an anti-MERTK antibody or an antigen-binding fragment thereof described herein has been produced, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an anti-MERTK antibody or an antigen-binding fragment thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.2.2. Polynucleotides

Also described herein are polynucleotides comprising a nucleotide sequence encoding an antibody described herein or an antigen-binding fragment thereof (e.g., a variable light chain region and/or variable heavy chain region) that immunospecifically binds to a MERTK (e.g., human MERTK, or both human and mouse MERTK) antigen, and vectors, e.g., vectors comprising such polynucleotides for their efficient expression in host cells (e.g., *E. coli* and mammalian cells). In some embodiments, a polynucleotide is isolated or purified.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% of other material, e.g., cellular material, culture medium, other nucleic acid molecules, chemical precursors and/or other chemicals.

In particular aspects, described herein are polynucleotides comprising nucleotide sequences encoding antibodies or antigen-binding fragments thereof, which immunospecifically bind to a MERTK polypeptide (e.g., human MERTK) and comprises an amino acid sequence as described herein, as well as antibodies which compete with such antibodies for binding to a MERTK polypeptide (e.g., in a dose-dependent manner), or which binds to the same or an overlapping epitope as that of such antibodies.

In certain aspects, described herein are polynucleotides comprising a nucleotide sequence encoding the light chain or heavy chain of an antibody described herein. The polynucleotides can comprise nucleotide sequences encoding a heavy chain comprising the VH CDRs described herein (see, e.g., Tables 1 and 3). The polynucleotides can comprise nucleotide sequences encoding a light chain comprising the VL CDRs described herein (see, e.g., Tables 2 and 4).

In particular embodiments, described herein are polynucleotides comprising a nucleotide sequence encoding a MERTK agonistic antibody comprising three VH chain CDRs, e.g., containing VH CDR1, VH CDR2, and VH CDR3 as described in Table 1 or Table 3. In specific embodiments, described herein are polynucleotides comprising a nucleotide sequence encoding a MERTK agonistic antibody comprising three VL chain CDRs, e.g., containing VL CDR1, VL CDR2, and VL CDR3 as described in Table 2 or Table 4. In specific embodiments, described herein are polynucleotides comprising a nucleotide sequence encoding a MERTK agonistic antibody comprising three VH chain CDRs, e.g., containing VH CDR1, VH CDR2, and VH CDR3 as described in Table 1 or Table 3, and three VL chain CDRs, e.g., containing VL CDR1, VL CDR2, and VL CDR3 as described in Table 2 or Table 4. In specific embodiments, a polynucleotide described herein encodes a VH CDR1, a VH CDR2, and a VH CDR3 of M6 (i.e., SEQ ID NOs: 1, 6, and 11; SEQ ID NOs: 2, 7, and 12; SEQ ID NOs: 3, 8, and 11; SEQ ID NOs: 4, 9, and 13; SEQ ID NOs: 5, 10, and 14; or SEQ ID NOs: 3, 6, and 11). In specific embodiments, a polynucleotide described herein encodes a VL CDR1, a VL CDR2, and a VL CDR3 of M6 (i.e., SEQ ID NOs: 15, 19, and 22; SEQ ID NOs: 16, 20, and 23; SEQ ID NOs: 17, 21, and 24; or SEQ ID NOs: 18, 20, and 22). In specific embodiments, a polynucleotide described herein encodes the a VH CDR1, a VH CDR2, and a VH CDR3 of M6 (i.e., SEQ ID NOs: 1, 6, and 11; SEQ ID NOs: 2, 7, and 12; SEQ ID NOs: 3, 8, and 11; SEQ ID NOs: 4, 9, and 13; SEQ ID NOs: 5, 10, or 14; or SEQ ID NOs: 3, 6, and 11), and the three VL CDRs of M6 (i.e., SEQ ID NOs: 15, 19, and 22; SEQ ID NOs: 16, 20, and 23; SEQ ID NOs: 17, 21, and 24; or SEQ ID NOs: 18, 20, and 22).

In specific embodiments, a polynucleotide described herein encodes a VH CDR1, a VH CDR2, and a VH CDR3 of M19 (i.e., SEQ ID NOs: 25, 30, and 35; SEQ ID NOs: 26, 31, and 36; SEQ ID NOs: 27, 32, and 35; SEQ ID NOs: 28, 33, and 37; SEQ ID NOs: 29, 34, and 38; or SEQ ID NOs: 27, 30, and 35). In specific embodiments, a polynucleotide described herein encodes a VL CDR1, a VL CDR2, and a VL CDR3 of M19 (e.g., SEQ ID NOs: 39, 43, and 46; SEQ ID NOs: 40, 44, and 47; SEQ ID NOs: 41, 45, and 48; or SEQ ID NOs: 42, 44, and 46). In specific embodiments, a polynucleotide described herein encodes the three VH CDRs of M19 (i.e., SEQ ID NOs: 25, 30, and 35; SEQ ID NOs: 26, 31, and 36; SEQ ID NOs: 27, 32, and 35; SEQ ID NOs: 28, 33, or 37; SEQ ID NOs: 29, 34, and 38; or SEQ ID NOs: 27, 30, and 35), and the three VL CDRs of M19 (i.e., SEQ ID NOs: 39, 43, and 46; SEQ ID NOs: 40, 44, and 47; SEQ ID NOs: 41, 45, and 48; or SEQ ID NOs: 42, 44, and 46).

In certain embodiments, a polynucleotide described herein comprises a nucleotide sequence encoding an anti-MERTK antibody described herein comprising a heavy chain variable region that comprises an amino acid sequence described herein (SEQ ID NO: 49 or 51), wherein the antibody immunospecifically binds to MERTK (e.g., human MERTK, or both human and mouse MERTK). In certain embodiments, a polynucleotide described herein comprises a nucleotide sequence encoding an anti-MERTK antibody described herein comprising a light chain variable region that comprises an amino acid sequence described herein (SEQ ID NOs: 50 or 52), wherein the antibody immunospecifically binds to MERTK (e.g., human MERTK, or both human and mouse MERTK). In certain embodiments, a polynucleotide described herein comprises a nucleotide sequence encoding an anti-MERTK antibody described herein comprising a heavy chain variable region that comprises the amino acid sequence of SEQ ID NO: 49, and a light chain variable region that comprises the amino acid sequence of SEQ ID NO: 50, wherein the antibody immunospecifically binds to MERTK (e.g., human MERTK, or both human and mouse MERTK). In certain embodiments, a polynucleotide described herein comprises a nucleotide sequence encoding an anti-MERTK antibody described herein comprising a heavy chain variable region that comprises the amino acid sequence of SEQ ID NO: 51, and a light chain variable region that comprises the amino acid sequence of SEQ ID NO: 52, wherein the antibody immunospecifically binds to MERTK (e.g., human MERTK, or both human and mouse MERTK).

In certain embodiments, a polynucleotide described herein encodes a VH comprising a nucleic acid sequence of SEQ ID NO: 53 or SEQ ID NO: 55. In certain embodiment, a polynucleotide described herein encodes a VL comprising a nucleic acid sequence of SEQ ID NO: 54 or SEQ ID NO: 56. In a specific embodiment, a polynucleotide described herein encodes a VH comprising a nucleic acid sequence of SEQ ID NO: 53, and a VL comprising the nucleic acid sequence of SEQ ID NO: 54 (e.g., M6). In another specific embodiment, a polynucleotide described herein encodes a VH comprising a nucleic acid sequence of SEQ ID NO: 55, and a VL comprising the nucleic acid sequence of SEQ ID NO: 56 (e.g., M19).

In specific aspects, described herein is a polynucleotide comprising a nucleotide sequence encoding an antibody comprising a light chain and a heavy chain, e.g., a separate light chain and heavy chain. With respect to the light chain, in a specific embodiment, a polynucleotide described herein comprises a nucleotide sequence encoding a kappa light chain. In another specific embodiment, a polynucleotide described herein comprises a nucleotide sequence encoding a lambda light chain. In yet another specific embodiment, a polynucleotide described herein comprises a nucleotide sequence encoding an antibody described herein comprising a human kappa light chain or a human lambda light chain. In a particular embodiment, a polynucleotide described herein comprises a nucleotide sequence encoding an antibody described herein, which immunospecifically binds to MERTK (e.g., human MERTK, or both human and mouse MERTK) and agonizes MERTK signaling of endothelial cells wherein the antibody comprises a light chain, and wherein the amino acid sequence of the variable region of the light chain can comprise any amino acid sequence of SEQ ID NO: 50 or SEQ ID NO: 52, and wherein the constant region of the light chain comprises the amino acid sequence of a human kappa light chain constant region. In another particular embodiment, a polynucleotide described herein comprises a nucleotide sequence encoding an antibody described herein, which immunospecifically binds to MERTK (e.g., human MERTK, or both human and mouse MERTK) and agonizes MERTK signaling of endothelial cells and comprise a light chain, wherein the amino acid sequence of the variable region of the light chain can comprise any amino acid sequence of SEQ ID NO: 50 or SEQ ID NO: 52, and wherein the constant region of the light chain comprises the amino acid sequence of a human lambda light chain constant region.

In certain embodiments, an optimized polynucleotide sequence encoding an MERTK agonistic antibody described herein or an antigen-binding fragment thereof (e.g., VH domain and/or VL domain) can hybridize to an antisense (e.g., complementary) polynucleotide of an unoptimized polynucleotide sequence encoding an MERTK agonistic antibody described herein or an antigen-binding fragment thereof (e.g., VH domain and/or VL domain). In specific embodiments, an optimized nucleotide sequence encoding an MERTK agonistic antibody described herein or an antigen-binding fragment hybridizes under high stringency conditions to antisense polynucleotide of an unoptimized polynucleotide sequence encoding an MERTK agonistic antibody described herein or an antigen-binding fragment thereof. In a specific embodiment, an optimized nucleotide sequence encoding a MERTK agonistic antibody described herein or an antigen-binding fragment thereof hybridizes under high stringency, intermediate or lower stringency hybridization conditions to an antisense polynucleotide of an unoptimized nucleotide sequence encoding an MERTK agonistic antibody described herein or an antigen-binding fragment thereof. In a specific embodiment, a polynucleotide described herein is codon optimized. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding MERTK agonistic antibodies described herein can be readily isolated and sequenced using conventional procedures (e.g., by using oligonucleotide probes that are capable of binding specifically to genes encoding the heavy and light chains of the MERTK agonistic antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of MERTK agonistic antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise a promoter, a secretion signal, a cloning site for the variable domain, constant domains, and a selection marker. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also described are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH (SEQ ID NO: 49 or 51) and/or VL (SEQ ID NO: 50 or 52) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In specific embodiments, the drug moiety is a peptide or protein fused to the N-terminus or C-terminus of one or more chains of the antibody moiety (directly or via a linker that is a peptide or protein). For example, when the antibody moiety is an scFv, the drug moiety can be fused at the N- or C-terminus of the scFv (directly or via a linker that is a peptide or protein). In a specific embodiment, when the antibody moiety is a multi-chain antibody or antigen-binding fragment thereof, the drug moiety can be fused to one of the chains of the antibody moiety (directly or via a linker that is a peptide or protein). In the case of an antibody that is an immunoglobulin, in a specific embodiment, both heavy chains can be fused to the drug moiety (directly or via a linker that is a peptide or protein), and/or both light chains can be fused to the linker drug moiety (directly or via a linker that is a peptide or protein). In such specific embodiments, provided herein are polynucleotides comprising a nucleotide sequence encoding a fusion protein composed of the drug moiety and the antibody moiety or a chain thereof, and the linker (if there is one) between the drug moiety and the antibody moiety. Such polynucleotides can be generated and isolated using the same methods as described above for anti-MERTK antibodies.

5.2.3. Cells and Vectors

Also described herein are vectors (e.g., expression vectors) comprising polynucleotides comprising nucleotide sequences encoding MERTK agonistic antibodies or an antigen-binding fragment thereof for recombinant expression in host cells, preferably in mammalian cells. Also described herein are host cells comprising such vectors for recombinantly expressing MERTK agonistic antibodies or antigen-binding fragments thereof described herein (e.g., human or humanized antibody).

Recombinant expression of an antibody described herein (e.g., a full-length antibody, heavy and/or light chain of an antibody, or a single chain antibody described herein) that specifically binds to MERTK (e.g., human MERTK, or both human and mouse MERTK) involves construction of an expression vector containing a polynucleotide that encodes the antibody. Once a polynucleotide encoding an antibody molecule, heavy and/or light chain of an antibody, or an antigen-binding fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also described are replicable vectors comprising a nucleotide sequence encoding an antibody molecule described herein, a heavy or light chain of an antibody, a heavy or light chain variable domain of an anti-MERTK antibody or antigen-binding fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or an antigen-binding fragment thereof. Thus, described herein are host cells containing a polynucleotide encoding an antibody described herein or an antigen-binding fragment thereof, or a heavy or light chain thereof, or a fragment thereof, or a single chain antibody described herein, operably linked to a promoter for expression of such sequences in the host cell. As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

A variety of host-expression vector systems can be utilized to express antibody molecules described herein. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., E. coli and B. subtilis) transformed with recombinant bacteriophage DNA, plasmid DNA or cosmid DNA expression vectors containing antibody coding sequences; yeast (e.g., Saccharomyces Pichia) transformed with recombinant yeast expression vectors containing antibody coding sequences; insect cell systems infected with recombinant virus expression vectors (e.g., baculovirus) containing antibody coding sequences; plant cell systems (e.g., green algae such as Chlamydomonas reinhardtii) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as Escherichia coli, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7). In certain embodiments, antibodies described herein are produced by CHO cells or NS0 cells. In a specific embodiment, the expression of nucleotide sequences encoding antibodies described herein which immunospecifically bind MERTK (e.g., human MERTK, or both human and mouse MERTK) and agonizes MERTK signaling of endothelial cells is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV), for example, can be used as a vector to express foreign genes. The virus grows in Spodoptera frugiperda cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain which modulates the expression of the inserted sequences, or modifies and processes the gene product in the specific fashion desired can be chosen. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, MERTK agonistic antibodies described herein are produced in mammalian cells, such as CHO cells.

In a specific embodiment, the antibodies described herein or antigen-binding fragments thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies or antigen-binding fragments thereof with reduced fucose content. The Potelligent® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an MERTK agonistic antibody described herein or an antigen-binding fragment thereof can be engineered. In specific embodiments, a cell described herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an MERTK agonistic antibody described herein or an antigen-binding fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al., (eds.), Current Protocols in Human Genetics, John Wiley & Sons, NY (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such an expression vector, the transcription of both genes can be driven by a common promoter, whereas the translation of the mRNA from the first gene can be by a cap-dependent scanning mechanism and the translation of the mRNA from the second gene can be by a cap-independent mechanism, e.g., by an IRES.

In specific embodiments, the drug moiety is a peptide or protein fused to the N-terminus or C-terminus of one or more chains of the antibody moiety (directly or via a linker that is a peptide or protein). For example, when the antibody moiety is an scFv, the drug moiety can be fused at the N- or C-terminus of the scFv (directly or via a linker that is a peptide or protein). In a specific embodiment, when the antibody moiety is a multi-chain antibody or antigen-binding fragment thereof, the drug moiety can be fused to one of the chains of the antibody moiety (directly or via a linker that is a peptide or protein). In the case of an antibody that is an immunoglobulin, in a specific embodiment, both heavy chains can be fused to the drug moiety (directly or via a linker that is a peptide or protein), and/or both light chains can be fused to the drug moiety (directly or via a linker that is a peptide or protein). In such specific embodiments, provided herein are vectors (e.g., expression vectors) comprising polynucleotides comprising a nucleotide sequence encoding a fusion protein composed of the drug moiety and the antibody moiety or a chain thereof, and the linker (if there is one) between the drug moiety and the antibody moiety, for recombinant expression in host cells, preferably in mammalian cells. Also provided herein are ex vivo host cells comprising such vectors for recombinantly expressing the fusion protein composed of the drug moiety and the antibody moiety or a chain thereof, and the linker (if there is one) between the drug moiety and the antibody moiety. Characteristcis of and methods for generating such vectors and ex vivo host cells can be the same as described above for anti-MERTK antibodies. Also provided herein are methods of producing the fusion protein composed of the drug moiety and the antibody moiety or a chain thereof, and the linker (if there is one) between the drug moiety and the antibody moiety, comprising culturing such an ex vivo host cell under conditions such that the polynucleotide comprising a nucleotide sequence encoding the fusion protein is expressed by the ex vivo host cell to produce the fusion protein.

5.3. Functional Characteristics of the Antibody-Drug Conjugates

In certain embodiments, an antibody-drug conjugate provided herein causes cell death of MERTK-expressing endothelial cells in vitro. In some specific embodiments, at least 10%, 20%, 30%, 35%, 40%, 50%, or 60% of MERTK-expressing endothelial cells cultured for a period of time in the presence of an antibody-drug conjugate described herein are dead at the end of the period of time, as assessed by methods known to one of skill in the art for measuring cell death in vitro. In other specific embodiments, the percentage of MERTK-expressing endothelial cells that undergo cell death is at least 50%, 100%, 2-fold, 3-fold, 5-fold, 10-fold, 20-fold, 50-fold, 100-fold, 200-fold, 500-fold, or 1000-fold higher when cultured for a period of time in the presence of an antibody-drug conjugate described herein, relative to when cultured without the antibody-drug conjugate (e.g., cultured without any antibody-drug conjugate or cultured with an antibody-drug conjugate comprising an unrelated antibody (e.g., an antibody that does not immunospecifically bind to MERTK) or cultured with an unconjugated anti-MERTK antibody or unconjugated anti-MERTK antigen-binding fragment described herein). The period of time can be, for example, about 1 hr, 2 hrs, 4 hrs, 8 hrs, 12 hrs, 16 hrs, 1 day, 2 days, 3 days, 4 days, 5 days, 6 days, or a week.

In specific embodiments, an antibody-drug conjugate described herein inhibits angiogenesis within tumors. In some embodiments, the inhibition of angiogenesis is by at least 10%, 20%, 30%, 40%, 50%, 55, 60%, 65%, 70%, or 75%. In a specific embodiment, the inhibition of angiogenesis is at least 50%, 55%, 60%, 65%, or 70%. Inhibition of angiogenesis can be assessed by methods described herein and/or known to one of skill in the art. The inhibition can be relative to the level of angiogenesis without the antibody-drug conjugate (e.g., cultured without any antibody-drug conjugate or cultured with an antibody-drug conjugate comprising an unrelated antibody (e.g., an antibody that does not immunospecifically bind to MERTK) or cultured with an unconjugated anti-MERTK antibody or unconjugated anti-MERTK antigen-binding fragment described herein). In a specific embodiment, the assay that is used to assess angiogenesis in vivo is as described in Example 6, infra.

In certain embodiments, an antibody-drug conjugate described herein inhibits tumor (e.g., human breast cancer tumor) progression. The inhibition of tumor progression by at least 10%, 20%, 30%, 40%, 50%, 60%, 70%, or 80%. Tumor progression can be assessed by methods described herein and/or known to one of skill in the art. The tumor progression can be relative to the cancer status without the antibody-drug conjugate (e.g., cultured without any antibody-drug conjugate or cultured with an antibody-drug conjugate comprising an unrelated antibody (e.g., an antibody that does not immunospecifically bind to MERTK) or cultured with an unconjugated anti-MERTK antibody or unconjugated anti-MERTK antigen-binding fragment described herein). In a specific embodiment, the assay that is used to assess tumor progression is a murine tumor transplantation model as described in Examples 5 and 8, infra.

5.4. The Drug Moiety and the Linker

The cytotoxic agent used in antibody-drug conjugates is also often called a payload or warhead. Most of the cytotoxic agents used in antibody-drug conjugates target DNA or microtubules and have high potency of cytotoxicity (with an $IC_{50}$ range of approximately $10^{-10}$-$10^{-12}$ M) (see Beck A et al., (2017) Nat Rev Drug Discov 16: 315-337). The cytotoxic agent can be a small molecule, a nucleotide, a peptide, or a non-antibody protein. In a specific embodiment, the cytotoxic agent is a small molecule. In another specific embodiment, the cytotoxic agent is a non-antibody protein. Non-limiting exemplary cytotoxic agents that can be used in the antibody-drug conjugates according to the invention are described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley. In specific embodiments, the cytotoxic agent used in the antibody-drug conjugate is an auristatin (such as monomethyl auristatin E (MMAE), monomethyl auristatin F (MMAF), Aur0101, PF06380101, Auristatin W, or auristatin F) or derivative thereof, a maytansinoid (such as DM1 or DM4), a pyrrolobenzodiazepine (PBD) (such as SGD1882 or SG3199), an indolinobenzodiazepine (such as DGN462 or DGN549), a calicheamicin (ozogamicin) (such as CM1), a camptothecin analogue (such as SN38, DX-8951f, or DX-8951f derivative), a duocarmycin (such as seco-duocarmycin-hydroxy-benzamide-azaindole (seco-DUBA), minor groove-binding alkylating agent (MGBA), or MED-2460), a tubulin inhibitor (such as cryptophycin), a tubulysin or tubulysin analogue (such as AZ13599185), amberstatin269, doxorubicin, an antibiotic (such as rifalogue), an anthracycline (such as PNU-159682), a microtubule inhibitor (such as rhizoxin), a spliceostatin, or a thailanstatin. In a specific embodiment, the cytotoxic agent used in the antibody-drug conjugate is MMAE or MMAF. In another specific embodiment, the cytotoxic agent used in the antibody-drug conjugate is DM1 or DM4.

As used herein, the term "small molecule" refers to an organic or inorganic compound (which can be, for example, a heteroorganic or organometallic compound) having a molecular weight of less than about 10,000 grams per mole. In specific embodiments, the small molecule has a molecular weight of less than about 5,000 grams per mole, or less than about 2,000 grams per mole, or less than about 1,000 grams per mole, or less than about 500 grams per mole, or less than about 100 grams per mole.

In some embodiments, the cytotoxic agent is conjugated directly to the antibody moiety. In other embodiments, the cytotoxic agent is conjugated to the antibody moiety via a linker. Appropriate linkers to be used according to the invention preferably are stable in the blood stream to limit off-target toxicity and labile at the cancer site to allow for release of the cytotoxic agent (see Peters C and Brown S, (2015) Biosci Rep 35: art:e00225). Non-limiting exemplary linkers that can be used according to the invention are described in Beck A et al., (2017) Nat Rev Drug Discov 16:

315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley. In some embodiments, the linker is a cleavable linker, for example, having a motif sensitive to a lysosomal protease (for example, cathepsin B), a motif sensitive to an acidic pH (for example, hydrazone), or a motif containing a disulfide bridge that can be reduced by glutathione. In other embodiments, the linker is a non-cleavable linker. By way of example but not limitation, the linker can be a small molecule, a nucleotide, a peptide, or a non-antibody protein. In a specific embodiment, the linker is a small molecule. In a specific embodiment, the linker used in the antibody-drug conjugate is cathepsin B, hydrazone, succinimidyl-4-(N-maleimidomethyl)cyclohexane-1-carboxylate (SMCC), maleimidocaproic acid (mc), valine-citrulline (vc), N-hydroxysuccinimidyl 4-(2-pyridyldithio)-2-sulfobutanoate (sulfo-SPDB), N-hydroxysuccinimidyl 4-(2-pyridydithio)butanoate (SPDB), N-succinimidyl 4-(2-pyridyldithio)pentanoate (SPP), valine-alanine (va), polyethylene glycol 8-valine-citrulline (PEG8-va), mb-vc, CL2A, cleavable vc-based linker, or fleximer polymer linker.

Non-limiting exemplary linker-drug moiety pairs that can be used according to the invention are described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; and Olivier K J and Hurvitz S A ed., (2016) Antibody-Drug Conjugates: Fundamentals, Drug Development, and Clinical, Wiley. In specific embodiments, the linker-drug moiety pair in the antibody-drug conjugate is vc-MMAE, mc-MMAF, SMCC-DM1, sulfo-SPDB-DM4, SPDB-DM4, SPP-DM1, va-SGD1882, polyethylene glycol 8 (PEG8)-va-SG3199, sulfo-SPDB-DGN462, hydrazone-CM1, vc-seco-DUBA, mb-vc-MGBA, CL2A-SN38, peptide linker with DX-8951 derivative, hydrazone-doxorubicin, cleavable vc-based linker with Aur0101, vc-PF06380101, fleximer polymer linker with auristatin F, cleavable linker-tubulin inhibitor, or vc-rifalogue.

5.5. Production of the Antibody-Drug Conjugates

In another aspect, provided herein are methods of producing an antibody-drug conjugate described herein wherein the linker is not present, the method comprising: (a) conjugating the cytotoxic agent directly to the antibody moiety to produce the antibody-drug conjugate; and (b) purifying the antibody-drug conjugate.

In another aspect, provided herein are methods of producing an antibody-drug conjugate described herein wherein the antibody-drug conjugate comprises the linker, the method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

In another aspect, provided herein are methods of producing an antibody-drug conjugate described herein wherein the antibody-drug conjugate comprises the linker, the method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

The conjugating and purifying steps can be performed by methods known in the art used for producing antibody-drug conjugates, such as the methods described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; or Olivier K J and Hurvitz S A ed., (2016) Antibody-Drug Conjugates: Fundamentals, Drug Development, and Clinical, Wiley. In some embodiments, the drug moiety is conjugated to one chain of the antibody moiety (for example, when the antibody moiety is a scFv, or when the antibody moiety is a multi-chain antibody, such as an immunoglobulin (which is a tetramer), or antigen-binding fragment thereof). In other embodiments, the drug moiety is conjugated to two or more chains of the antibody moiety (when the antibody moiety is a multi-chain antibody, such as an immunoglobulin, or antigen-binding fragment thereof). In a specific embodiment, the drug moiety is conjugated to two identical chains of an immunoglobulin, e.g., the heavy chains or the light chains. In other embodiments, the drug moiety is conjugated to all chains of the antibody moiety (when the antibody moiety is a multi-chain antibody, such as an immunoglobulin or antigen-binding fragment thereof). In a specific embodiment, the antibody-drug conjugate described herein is purified by chromatograph. In another specific embodiment, the antibody-drug conjugate described herein is purified by centrifugation. By way of example but not limitation, the conjugation chemistry that can be used for generating the antibody-drug conjugate can be thiol plus maleimide, thiol plus self-hydrolyzing maleimide, thiol plus phenyloxadiazole sulfone, oxime ligation, alkoxyamine-to-keto-group reaction, strain-promoted azide-alkyne cycloaddition (SPAAC), copper-free click chemistry, cysteine oxidized to formylglycine, hydrazino-iso-Pictet-Spengler (HIPS) ligation, ligation of γ-carboxyamide group from glutamine residues plus primary amines, ligation LPETG plus primary amine of polyglycine motif, maleimide plus 6-thiofucose, fucose-specific conjugation of hydrazide, periodate oxidation (aldehyde) plus amino-oxy-payload, strain-promoted alkyn-azide cycloaddition, C2-keto-gal oxi-mation, site selective aldehyde oxidation plus oxime ligation, oxime ligation NH2 plus indole-based 5-difluoro-2,4-dinitrobenzene derivatives, thiol plus bis-sulfone, thiol plus dibromomaleimide, thiol plus maleimide followed by pH 9.2 treatment (45° C., 48 hours), or thiol plus arylpropionitrile (see Beck A et al., (2017) Nat Rev Drug Discov 16: 315-337).

The anti-MERTK antibody or an antigen-binding fragment thereof described herein can be generated as described in Section 5.2. In specific embodiments, the anti-MERTK antibody or an antigen-binding fragment thereof described herein is engineered or modified by a method known in the art to facilitate conjugation with the drug moiety(ies), in particular to facilitate site-specific conjugation with the drug moiety(ies), for example, by a method described in Beck A et al., (2017) Nat Rev Drug Discov 16: 315-337; Peters C and Brown S, (2015) Biosci Rep 35: art:e00225; McCombs J R and Owen S C (2015) The AAPS Journal 17: 339-351; Jackson D Y (2016) Org Process Res Dev 20: 852-866; or Olivier K J and Hurvitz S A ed., (2016) Antibody-Drug Conjugates: Fundamentals, Drug Development, and Clinical, Wiley. Non-limiting exemplary methods that can be used (see Beck A et al., (2017) Nat Rev Drug Discov 16:

315-337) to engineer or modify an anti-MERTK antibody or an antigen-binding fragment thereof to facilitate conjugation with the drug moiety(ies) include adding one or more adinol cysteines or selenocysteines, unnatural amino acid engineering, adding one or more amino acid tags recognizable by certain enzymes that can assist with the conjugation, glycan remodeling, adding an amino-terminal serine, and native cysteine bridging.

The linker and the cytotoxic agent can be generated by any method known in the art for producing the linker and the cytotoxic agent, respectively.

5.6. Pharmaceutical Compositions

Provided herein are pharmaceutical compositions comprising an antibody-drug conjugate described herein and a pharmaceutically acceptable carrier. In a specific embodiment, the antibody-drug conjugate is purified. In a specific embodiment, the antibody-drug conjugate is present in the pharmaceutical composition in a therapeutically effective amount.

In a specific embodiment, the population of antibody-drug conjugates contained in the pharmaceutical composition have a drug-to-antibody ratio (DAR) between 1 to 20. DAR is the average number of cytotoxic agents conjugated to the antibodies. In another specific embodiment, the population of antibody-drug conjugates contained in the pharmaceutical composition have a DAR between 1 to 15. In another specific embodiment, the population of antibody-drug conjugates contained in the pharmaceutical composition have a DAR between 1 to 12. In another specific embodiment, the population of antibody-drug conjugates contained in the pharmaceutical composition have a DAR between 1 to 8. In another specific embodiment, the population of antibody-drug conjugates contained in the pharmaceutical composition have a DAR between 3 to 5. In another specific embodiment, the population of antibody-drug conjugates contained in the pharmaceutical composition have a DAR between 3.5 to 4.

Acceptable carriers, which can be excipients or stabilizers, are nontoxic to recipients at the dosages and concentrations employed, and include but are not limited to buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an antibody-drug conjugate described herein, and optionally one or more additional prophylactic or therapeutic agents, in a pharmaceutically acceptable carrier. In a specific embodiment, pharmaceutical compositions comprise an effective amount of an antibody-drug conjugate described herein, and optionally one or more additional prophylactic or therapeutic agents, in a pharmaceutically acceptable carrier. In a specific embodiment, the pharmaceutical compositions and/or antibody-drug conjugate described herein, can be combined with a therapeutically effective amount of any of the additional therapeutic agents described herein (See Section 5.7.2, infra).

In some embodiments, the antibody-drug conjugate is the only active ingredient included in the pharmaceutical composition.

Pharmaceutical compositions described herein can be used to treat cancer.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody-drug conjugate include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody-drug conjugate are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody-drug conjugate described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody-drug conjugate described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody-drug conjugate alone or in combination with other pharmaceutically acceptable excipients can also be administered.

Transdermal patches, including iontophoretic and electrophoretic devices, are well known to those of skill in the art, and can be used to administer an antibody-drug conjugate. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody-drug conjugate described herein is a lyophilized powder, which can be reconstituted for administration as solutions, emulsions and other mixtures. It may also be reconstituted and formulated as solids or gels. The lyophilized powder is prepared by dissolving an antibody-drug conjugate described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibody-drug conjugates described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, an antibody-drug conjugate described herein is targeted to a tumor.

The compositions to be used for in vivo administration can be sterile. This is readily accomplished by filtration through, e.g., sterile filtration membranes.

5.7. Uses and Methods

5.7.1. Therapeutic Uses and Methods
5.7.1.1. Cancer

In one aspect, presented herein are methods for treating cancer in a subject, comprising administering to a subject in need thereof an antibody-drug conjugate described herein, or a pharmaceutical composition comprising an antibody-drug conjugate described herein. In a specific embodiment, presented herein are methods for treating cancer in a subject, comprising administering to a subject in need thereof a pharmaceutical composition comprising an antibody-drug conjugate described herein. In a particular embodiment, presented herein are methods for treating cancer in which it is desirable to agonize MERTK signaling of endothelial cells, for example to inhibit angiogenesis, comprising administering to a subject in need thereof a pharmaceutical composition comprising an antibody-drug conjugate described herein.

In specific embodiments, the administration of an antibody-drug conjugate described herein, or a pharmaceutical composition described herein to a subject with cancer achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxi) an increase in the length of remission in patients.

In some embodiments, the cancer treated in accordance with the methods described herein is a cancer of the lung, breast, bone, ovary, stomach, pancreas, larynx, esophagus, testes, liver, parotid, biliary tract, colon, rectum, cervix, uterus, endometrium, kidney, bladder, prostate or thyroid. In some embodiments, the cancer is a sarcoma, squamous cell carcinoma, melanoma, glioma, glioblastoma, neuroblastoma or Kaposi's sarcomas. In some embodiments, the cancer treated in accordance with the methods is metastatic.

In a specific embodiment, the cancer treated in accordance with the methods described herein is breast cancer. In a particular embodiment, the cancer treated in accordance with the methods described herein is triple-negative breast cancer. Triple-negative breast cancer refers to any tumor or cell derived from or growing in breast tissue that does not express the genes Her2 (also known as Neu), Estrogen Receptor (also known as ER) or Progesterone Receptor (also known as PR).

As used herein, the terms "subject" and "patient" are used interchangeably. In some embodiments, the subject is a mammal such as a primate (e.g., monkey or human), most preferably a human.

In a specific embodiment, an antibody-drug conjugate described herein is administered to a subject. In certain embodiments, two or more different antibody-drug conjugates described herein are administered to a subject. In some embodiments, an antibody-drug conjugate described herein is administered to a subject in combination with one or more other therapies (See Section 5.7.2, Infra.).

5.7.1.2. Routes of Administration and Dosage

An antibody-drug conjugate, or composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, an antibody-drug conjugate, or a composition described herein is administered parenterally to a subject. In a specific embodiment, said parenteral administration is intravenous, intramuscular, or subcutaneous. In a specific embodiment, an antibody-drug conjugate is administered intravenously to a subject.

The amount of an antibody-drug conjugate, or composition which will be effective in the treatment and/or prevention of a condition will depend on the nature of the disease, and can be determined by standard clinical techniques. The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For an antibody-drug conjugate, the dosage can range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 1 mg/kg to about 20 mg/kg of the patient's body weight. Generally, human antibodies have a longer half-life within the human body than antibodies from other species due to the immune response to the foreign polypeptides. Thus, lower dosages of antibody-drug conjugates comprising human antibodies and less frequent administration is often possible.

An exemplary treatment regime entails administration once per every two weeks or once a month or once every 3 to 6 months for a period of one year or over several years, or over several year-intervals. In some methods, two or more antibody-drug conjugates are administered simultaneously to a subject. An antibody-drug conjugate is usually administered on multiple occasions. Intervals between single dosages can be weekly, monthly, every 3 months, every 6 months or yearly.

5.7.2. Combination Therapies

In a specific embodiment, the methods provided herein for treating cancer in a subject, comprising administering to a subject in need thereof a pharmaceutical composition comprising an antibody-drug conjugate described herein, further comprise administering to the subject one or more additional therapeutic agents. In a specific embodiment, the additional therapeutic agent is for treating the cancer. In a specific embodiment, the additional therapeutic agent is for treating any side effects of treatment with an antibody-drug conjugate described herein.

In specific embodiments, the additional agent is an agent used to treat breast cancer, an agent used to treat melanoma, an immunotherapy, or an angiogenesis inhibitor.

In a specific embodiment, the additional therapeutic agent is an agent used to treat breast cancer that is selected from the group consisting of Tamoxifen, Raloxifene, Paclitaxel (TAXOL®), Cyclophosphamide, Docetaxel, Vinblastine, Fluorouracil, Everolimus, Trastuzumab, Trastuzumab-Emtansine, Pertuzumab, and Lapatinib Ditosylate.

In a specific embodiment, the additional therapeutic agent is an agent used to treat melanoma that is selected from the group consisting of a BRAF inhibitor, a MEK inhibitor, and Dacarbazine.

In a specific embodiment, the additional therapeutic agent is an antibody that is a CTLA-4 inhibitor, a PD-1 inhibitor, or a PD-L1 inhibitor.

In a specific embodiment, the additional therapeutic agent is an angiogenesis inhibitor that is selected from the group consisting of a VEGF inhibitor, a VEGFR2 inhibitor, Sunitinib, and Sorafenib.

In other embodiments, the additional therapeutic agent is an agent listed in Table 10.

TABLE 10

Additional Therapeutic Agents for Use in Combination Therapy with MERTK Antibodies or Antigen-Binding Fragments Thereof

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | Raltitrexed | Capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | Topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | Doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | Paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |

TABLE 10-continued

Additional Therapeutic Agents for Use in Combination Therapy with MERTK
Antibodies or Antigen-Binding Fragments Thereof

| Category | Agents | Agents |
|---|---|---|
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenies) | ISF-154 (Tragen) |
| | adenocarcinoma vaccine (Biomira) | cancer vaccine (Intercell) |
| | CTP-37 (AVI BioPharma) | norelin (Biostar) |
| | IRX-2 (Immuno-Rx) | BLP-25 (Biomira) |
| | PEP-005 (Peplin Biotech) | MGV (Progenies) |
| | synchrovax vaccines (CTL Immuno) | ß-alethine (Dovetail) |
| | melanoma vaccine (CTL Immuno) | CLL therapy (Vasogen) |
| | p21 RAS vaccine (GemVax) | Ipilimumab (BMS), |
| | MAGE-A3 (GSK) | CM-10 (cCam Biotherapeutics) |
| | nivolumab (BMS) | MPDL3280A (Genentech) |
| | abatacept (BMS) | pidilizumab (CureTech) |
| | lambrolizumab (Merck) | AMP-224 (GSK) |
| | MEDI-4736 (AstraZeneca) | |
| Hormonal and antihormonal agents | estrogens | dexamethasone |
| | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; fluoxymesterone | P-04 (Novogen) |
| | methyltestosterone | 2-methoxyestradiol (EntreMed) |
| | diethylstilbestrol | arzoxifene (Eli Lilly) |
| | megestrol | tamoxifen |
| | bicalutamide | toremofine |
| | flutamide | goserelin |
| | nilutamide | Leuporelin |
| | | bicalutamide |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |

TABLE 10-continued

Additional Therapeutic Agents for Use in Combination Therapy with MERTK Antibodies or Antigen-Binding Fragments Thereof

| | | |
|---|---|---|
| | trastuzumab (Genentech) | Tyrphostins |
| | OSI-774 (Tarceva ™) | Gefitinib (Iressa) |
| | CI-1033 (Pfizer) | PTK787 (Novartis) |
| | SU11248 (Pharmacia) | EMD 72000 (Merck) |
| | RH3 (York Medical) | Emodin |
| | Genistein | Radicinol |
| | Radicinol | Vemurafenib (B-Raf enzyme inhibitor, Daiichi Sankyo) |
| | Met-MAb (Roche) | |
| | trametinib (GSK) | |
| Additional Agents | SR-27897 (CCK A inhibitor, Sanofi-Synthelabo) | ceflatonin (apoptosis promotor, ChemGenex) |
| | tocladesine (cyclic AMP agonist, Ribapharm) | BCX-1777 (PNP inhibitor, BioCryst) |
| | alvocidib (CDK inhibitor, Aventis) | ranpirnase (ribonuclease stimulant, Alfacell) |
| | CV-247 (COX-2 inhibitor, Ivy Medical) | galarubicin (RNA synthesis inhibitor, Dong-A) |
| | P54 (COX-2 inhibitor, Phytopharm) | tirapazamine (reducing agent, SRI International) |
| | CapCell ™ (CYP450 stimulant, Bavarian Nordic) | N-acetylcysteine (reducing agent, Zambon) |
| | GCS-100 (gal3 antagonist, GlycoGenesys) | R-flurbiprofen (NF-kappaB inhibitor, Encore) |
| | G17DT immunogen (gastrin inhibitor, Aphton) | 3CPA (NF-kappaB inhibitor, Active Biotech) |
| | efaproxiral (oxygenator, Allos Therapeutics) | seocalcitol (vitamin D receptor agonist, Leo) |
| | PI-88 (heparanase inhibitor, Progen) | 131-I-TM-601 (DNA antagonist, TransMolecular) |
| | tesmilifene (histamine antagonist, YM BioSciences) | eflornithine (ODC inhibitor, ILEX Oncology) |
| | histamine (histamine H2 receptor agonist, Maxim) | minodronic acid (osteoclast inhibitor, Yamanouchi) |
| | tiazofurin (IMPDH inhibitor, Ribapharm) | indisulam (p53 stimulant, Eisai) |
| | cilengitide (integrin antagonist, Merck KGaA) | aplidine (PPT inhibitor, PharmaMar) |
| | SR-31747 (IL-1 antagonist, Sanofi-Synthelabo) | gemtuzumab (CD33 antibody, Wyeth Ayerst) |
| | CCI-779 (mTOR kinase inhibitor, Wyeth) | PG2 (hematopoiesis enhancer, Pharmagenesis) |
| | exisulind (PDE V inhibitor, Cell Pathways) | Immunol ™ (triclosan oral rinse, Endo) |
| | CP-461 (PDE V inhibitor, Cell Pathways) | triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promotor, Procyon) |
| | bortezomib (proteasome inhibitor, Millennium) | doranidazole (apoptosis promotor, Pola) |
| | SRL-172 (T cell stimulant, SR Pharma) | CHS-828 (cytotoxic agent, Leo) |
| | TLK-286 (glutathione S transferase inhibitor, Telik) | trans-retinoic acid (differentiator, NIH) |
| | PT-100 (growth factor agonist, Point Therapeutics) | MX6 (apoptosis promotor, MAXIA) |
| | midostaurin (PKC inhibitor, Novartis) | apomine (apoptosis promotor, ILEX Oncology) |
| | bryostatin-1 (PKC stimulant, GPC Biotech) | urocidin (apoptosis promotor, Bioniche) |
| | CDA-II (apoptosis promotor, Everlife) | Ro-31-7453 (apoptosis promotor, La Roche) |
| | SDX-101 (apoptosis promotor, Salmedix) | brostallicin (apoptosis promotor, Pharmacia) |
| | rituximab (CD20 antibody, Genentech) | β-lapachone |
| | carmustine | gelonin |
| | Mitoxantrone | cafestol |
| | Bleomycin | kahweol |
| | Absinthin | caffeic acid |
| | Chrysophanic acid | Tyrphostin AG |
| | Cesium oxides | PD-1 inhibitors |
| | BRAF inhibitors, | CTLA-4 inhibitors |

TABLE 10-continued

Additional Therapeutic Agents for Use in Combination Therapy with MERTK
Antibodies or Antigen-Binding Fragments Thereof

| | |
|---|---|
| PDL1 inhibitors | sorafenib |
| MEK inhibitors | BRAF inhibitors |
| bevacizumab | |
| angiogenesis inhibitors | |
| dabrafenib | |

An antibody-drug conjugate described herein can be administered with an additional therapeutic agent concurrently or sequentially (before and/or after). The antibody-drug conjugate and the additional therapeutic agent can be administered in the same or different compositions, and by the same or different routes of administration. A first therapy (which is an antibody-drug conjugate described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the antibody-drug conjugate described herein, or the additional therapeutic agent) to a subject with cancer. In certain embodiments, an additional therapeutic agent administered to a subject in combination with an antibody-drug conjugate is administered in the same composition (pharmaceutical composition). In other embodiments, an additional therapeutic agent administered in combination with an antibody-drug conjugate is administered to a subject in a different composition than the antibody-drug conjugate (e.g., two or more pharmaceutical compositions are used).

5.8. Kits

Also provided herein are kits comprising one or more antibody-drug conjugates described herein. In a specific embodiment, provided herein is a pharmaceutical pack or kit comprising one or more containers filled with one or more of the ingredients of the pharmaceutical compositions described herein, such as one or more antibody-drug conjugates described herein. In some embodiments, the kits contain a pharmaceutical composition described herein and a prophylactic or therapeutic agent.

Optionally associated with such container(s) can be a notice in the form prescribed by a governmental agency regulating the manufacture, use or sale of pharmaceuticals or biological products, a dosage form, and/or instructions for use thereof. In certain embodiments, the instructions included with the kit provide guidance with respect to the dosage amounts and/or dosing regimens for administration of the pharmaceutical composition(s).

Examples of pharmaceutical packaging materials include, but are not limited to, blister packs, bottles, packets, sachets, tubes, inhalers, pumps, bags, vials, containers, syringes and any packaging material suitable for a selected pharmaceutical composition and intended mode of administration and treatment.

Kits provided herein can further include devices that are used to administer the active ingredients. Examples of such devices include, but are not limited to, syringes, needle-less injectors, drip bags, patches and inhalers.

Kits provided herein can further include pharmaceutically acceptable vehicles that can be used to administer the ingredients. For example, if an ingredient is provided in a solid form that must be reconstituted for parenteral administration, the kit can comprise a sealed container of a suitable vehicle in which the ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

The following examples are offered by way of illustration and not by way of limitation.

6. EXAMPLES 6.1. Example 1: Generation of High Affinity MERTK-Binding Monoclonal Antibodies This example describes monoclonal antibodies that inhibit endothelial recruitment by metastatic breast cancer cells by binding to MERTK and activating its phosphorylation. The peptide antigen used to immunize mice in order to generate the antibodies described in this example was purchased from R&D systems (Recombinant Human Mer Fc Chimera, #CF891-MR-100). This is a chimeric peptide comprised of a large portion of the extracellular domain of MERTK (Arg26 to Ala499; SEQ ID NO: 58) fused to a portion of the Fc region of the human $IgG_1$ protein (Pro100-Lys330) with a small linking peptide in between (IEGRMD). See FIG. 1A for a schematic of the chimeric peptide. After mice were immunized with the chimeric peptide, hybridoma libraries were generated by fusion of B cells isolated from the immunized mice to myeloma cell lines. Supernatant from these hybridomas were then isolated in order to identify those hybridoma cells generating antibodies that bind MERTK, using antibody capture competitive ELISA assays (FIG. 2), as described in Section 6.1.1, infra. Once identified, hybridomas generating antibodies with high affinity to MERTK were screened in order to identify those that generated antibodies capable of inhibiting MERTK from binding Gas-6, using antibody capture competitive ELISA assays (FIG. 2), as described in Section 6.1.2, infra. To isolate single clones (monoclonal) hybridoma cells, separation and screening was performed on the hybridoma library. 960 single hybridoma clones (monoclonal) were screened from this library to identify those that generated monoclonal antibodies that bound to MERTK with high affinity to neutralize Gas-6 binding.

6.1.1. ELISA Capture Assay for MERTK Binding:

In order to identify monoclonal antibodies that bind to MERTK, an ELISA antibody capture assay was used to screen secreted antibodies generated from each hybridoma clone generated from mice immunized with recombinant MERTK protein. First, polystyrene plates were coated with coating antibody (Goat anti Mouse IgG (Fc); Lot #: Jackson 98959; antibody concentration of 10 ug/mL). Then, supernatant containing primary antibody from each monoclonal hybridoma clone was added to each well in the plate. Next, tagged antigen (recombinant human Mer-Fc; RnD systems #891-MR; Lot #: CXK0211051; concentration 300 ng/mL) was added to each well. Then, detection antibody (horse radish peroxidase [HRP] conjugated Goat anti-Human IgG (Fc); Lot #: Jackson 86954; dilution: 1/5000) was added to each well. This was followed by addition of HRP substrate and subsequent addition of stop solution to complete the reaction. The signal (O.D.) from each well was read using a spectrophotometer. Of all 960 hybridoma clones tested, twenty demonstrated O.D. values >1, indicating significant binding affinity to human MERTK. An O.D. reading of 1 indicates at least 4 times the signal that was observed with the negative control (empty media without antibody), which had an O.D. value of 0.22. These twenty clones were named arbitrarily M1 to M20 and are listed in FIG. 2. The second column (with the heading "Mer") in FIG. 2 indicates the O.D. reading (indicative of binding affinity) for each clone.

6.1.2. Competitive Gas-6 Binding ELISA Assay

In order to then identify antibodies that inhibit Gas-6 binding to MERTK, a Gas-6 competitive binding ELISA assay was performed on the twenty MERTK-binding antibodies (M1-M20). First, polystyrene plates were coated with recombinant human GAS-6 (RnD systems rhGas6 #885-GS-050; concentration 7 ug/mL). Next, supernatant containing primary antibody from each monoclonal hybridoma clone was added to each well in the plate. Simultaneously, recombinant human MERTK (Mer-Fc RnD systems #891-MR; Lot #: CXK0211051; concentration 300 ng/mL) was added to each well. Then, detection antibody (horse radish peroxidase [HRP] conjugated Goat anti-Human IgG (Fc); Lot #: Jackson 86954; dilution: 1/5000) was added to each well. This was followed by the addition of HRP substrate and stop solution to complete the reaction. The signal (O.D.) was measured from each plate using a spectrophotometer. Of all the hybridoma clones tested in this assay, 11 demonstrated O.D. values <2.4, which indicated they inhibited Gas-6 binding to MERTK. An O.D. reading of 2.4 indicates inhibition of Gas-6 binding to MERTK, as the signal that was observed with the negative control (empty media without antibody) was 2.43. These twenty clones are listed in FIG. 2. The third column (with the heading "(Mer+Clone)") in FIG. 2 indicates the O.D. reading (indicative of amount of inhibition of Gas-6 binding) for each clone.

The two monoclonal antibodies M6 and M19 were selected for further study, including whether they could inhibit endothelial recruitment by metastatic cells using trans-well endothelial migration assays.

6.2. Example 2: M19 and M6 Antibodies are Capable of Inhibiting Endothelial Cell Recruitment by Triple Negative Breast Cancer Cells In Vitro To identify monoclonal antibodies that could inhibit endothelial recruitment by activation of MERTK, the high-affinity Gas-6-competing monoclonal antibodies generated in the screen described in Example 1, supra, were tested in an in vitro endothelial recruitment assay using transwells. Metastatic MDA-MB-231 human breast cancer cells were placed in the bottom of a Boyden chamber, where their ability to recruit HUVECS through a porous trans-well insert could be assayed. MERTK binding antibodies from our screen (including both high and low affinity antibodies) were added to the transwells individually in physiologic concentrations. Of all antibodies tested, M19 and M6 were most able to significantly inhibit the recruitment (migrated cells/field) of HUVEC cells (50% reduction in migrated cells) versus the negative control antibody IgG (FIG. 3). This demonstrates the ability of the monoclonal antibodies M19 and M6 to inhibit human endothelial cell recruitment by human metastatic cancer cells (FIG. 3).

6.3. Example 3: M19 and M6 Antibodies Activate MERTK Phosphorylation on Endothelial Cells To confirm that M19 and M6 are indeed MERTK activating antibodies, western blot analysis was performed to quantify the levels of phosphorylated (activated) MERTK expressed by endothelial cells (HUVECs) in the presence or absence of M19 or M6 antibody treatment. (FIG. 4, FIG. 5).

To perform Western blot analysis, HUVEC cells (or LM2 breast cancer cells) were grown to 80% confluence in EGM-2 media (Lonza, cat #CC-3162) containing 10% FBS. After a 16 hour incubation under the given conditions the cells were washed in PBS and lysed in 1 mL RIPA buffer (G-Biosceince, Cat #786-490) containing protease and phosphatase inhibitors (Roche, Cat #11 836 170 001 and 04 906 845 001, respectively). Proteins from the cell lysates were then separated on a SDS-PAGE and transferred to a PVDF membrane. For detection of proteins the following primary antibodies were used: Phosphorylated-MERTK (FabGennix, cat #PMKT-140AP), MERTK (Abcam, cat #ab52968), Phosphorylated-Akt (Santa Cruz Biotechnology, cat #sc-7985R), and Akt (Santa Cruz Biotechnology, cat #sc-1618). The primary antibodies were detected using the appropriate HRP conjugated secondary antibodies (Life Technologies).

Cultured cells treated with the specified antibodies resulted in an increase in activation of MERTK on endothelial cells, in a dose dependent manner during both chronic (16 hour) and acute (30 minute) antibody treatment (FIG. 4, FIG. 5). Interestingly, M19 antibody treatment did not increase activation of MERTK on LM2 breast cancer cells (FIG. 6).

6.4. Example 4: M19 Binds with High Affinity to Both Human and Mouse MERTK

This example demonstrates that M19 antibody binds with high affinity ($K_D$ of ~0.3 nM) to both human and murine MERTK. To characterize the binding affinity of M19 antibody against recombinant human and mouse MERTK, biomolecular interaction analysis was performed using biolayer interferometry (FIG. 7 and FIG. 8). Binding was observed between M19 and both mouse and human MERTK. The overall global fit calculated binding affinity ($K_D$) for M19 binding to human and mouse MERTK were similar ($K_D$=~0.3 nM) (FIG. 7, FIG. 8).

6.5. Example 5: Therapeutic Administration of M19 Inhibits Tumor Progression of Human Breast Cancer In Vivo This example demonstrates that the MERTK activating antibody M19 is capable of inhibiting tumor progression and tumor metastasis in vivo in a mouse model of human breast cancer. To test whether monoclonal antibody M19 was able to reduce tumor burden and inhibit tumor progression in vivo, 2000 MDA-MB-231 or 5000 Lm1a1 cells were mixed in a 1:1 ratio with growth factor reduced matrigel and injected bilaterally in the mammary fat pads of NOD-SCID mice. Intraperitoneal injections of 250 μg of either M19 antibody or control IgG antibody was injected after the surgery and subsequently twice a week. Tumor size of palpable tumors was measured weekly using a caliber. Treatment with M19 antibody did demonstrate a significant therapeutic inhibition of both primary tumor growth (FIG. 9A) and metastasis (FIG. 9B) of triple-negative breast cancer in vivo.

6.6. Example 6: M19 Inhibits Tumor Angiogenesis In Vivo

To investigate whether therapeutic treatment with M19 antibody results in an inhibition of angiogenesis in vivo, blood vessel density within tumors of M19 treated and untreated mice were quantified. 2000 MDA-MB-231 were injected bilaterally into the mammary fad pad of NOD-SCID mice. After 58 days of treatment with 250 μg of either M19 antibody or control IgG antibody the tumors were excised and blood vessel density was quantified (FIG. 10). Indeed, therapeutic treatment with M19 antibody did result in a significant inhibition (>50%) of angiogenesis in vivo (FIG. 10).

6.7. Example 7: M6 Binds with High Affinity to Both Human MERTK

This example demonstrates that M6 antibody binds with high affinity ($K_D$ of ~4.6 picomolar) to recombinant human MERTK. To characterize the binding affinity of M6 antibody, biomolecular interation analysis was performed using biolayer interferometry (FIG. 11). Binding was observed between M6 and human MERTK. The overall global fit calculated binding affinity ($K_D$) for M6 binding to human MERTK was ~4.6 picomolar (FIG. 11).

6.8. Example 8: Therapeutic Administration of M6 Inhibits Tumor Progression of Human Breast Cancer In Vivo This example demonstrates that the MERTK activating antibody M6 is capable of inhibiting tumor progression in vivo in a mouse model of human breast cancer. To test whether monoclonal antibody M6 was able to reduce tumor burden and inhibit tumor progression in vivo, 2000 MDA-MB-231 breast cancer cells were mixed in a 1:1 ratio with growth factor reduced matrigel (BD Biosciences) and injected bilaterally in the mammary fat pads of NOD-SCID mice. Intraperitoneal injections of 250 μg of either M6 antibody or control IgG antibody was injected after the surgery and subsequently twice a week. Tumor size of palpable tumors was measured weekly using a caliber. Indeed, treatment with M6 antibody twice weekly resulted in a significant reduction in tumor size (FIG. 12).

6.9. Example 9: Antibody Sequences for M6 and M19

To further characterize M19 and M6, the heavy chain and light chain variable regions of these antibodies were sequenced. The amino acid sequences of both the heavy chain and light chain variable regions of M6 are presented in Table 5. The nucleic acid sequences of both the heavy chain and light chain variable regions of M6 are presented in Table 7. The amino acid sequences of the CDRs of M6 are presented in Table 1 (for VH) and Table 2 (for VL).

The amino acid sequences of both the heavy chain and light chain variable regions of M19 are presented in Table 6. The nucleic acid sequences of both the heavy chain and light chain variable regions of M6 is presented in Table 8. The amino acid sequences of the CDRs of M19 are presented in Table 3 (for VH) and Table 4 (for VL).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

6.10. Example 10: Treatment of Metastatic Triple-Negative Breast Cancer with Anti-MERTK Agonistic Antibody-Drug Conjugates The monoclonal antibody M6 described in Example 1 (Section 6.1) is humanized and conjugated to the cytotoxic agent monomethyl auristatin F (MMAF) via maleimidocaproic acid (mc) (i.e., the linker). The anti-MERTK antibody-drug conjugate is purified and administered intravenously to a patient who presents with metastatic triple-negative breast cancer. The patient is monitored before, during, and after the antibody-drug conjugate administration for response by clinical assessments.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

What is claimed:

1. A method of producing an antibody-drug conjugate, said antibody-drug conjugate comprising (a) an antibody moiety that is an antibody or antigen-binding fragment thereof that specifically binds to human MERTK; and (b) one or more drug moieties, each drug moiety being a cytotoxic agent; and (c) a linker; wherein the cytotoxic agent is conjugated to the antibody moiety via the linker;
wherein said antibody or antigen-binding fragment comprises a heavy chain variable region (VH) and a light chain variable region (VL), and wherein
(i) the VH comprises a CDR1 of SEQ ID NO: 25, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46; or
(ii) the VH comprises a CDR1 of SEQ ID NO: 26, a CDR2 of SEQ ID NO: 31, and a CDR3 of SEQ ID NO: 36; and the VL comprises a CDR1 of SEQ ID NO: 40, a CDR2 of SEQ ID NO: 44, and a CDR3 of SEQ ID NO: 47; or
(iii) the VH comprises a CDR1 of SEQ ID NO: 27, a CDR2 of SEQ ID NO: 32, and a CDR3 of SEQ ID NO: 35; and the VL comprises a CDR1 of SEQ ID NO: 39, a CDR2 of SEQ ID NO: 43, and a CDR3 of SEQ ID NO: 46; or
(iv) the VH comprises a CDR1 of SEQ ID NO: 28, a CDR2 of SEQ ID NO: 33, and a CDR3 of SEQ ID NO: 37; and the VL comprises a CDR1 of SEQ ID NO: 41, a CDR2 of SEQ ID NO: 45, and a CDR3 of SEQ ID NO: 48; or
(v) the VH comprises a CDR1 of SEQ ID NO: 29, a CDR2 of SEQ ID NO: 34, and a CDR3 of SEQ ID NO: 38; and the VL comprises a CDR1 of SEQ ID NO: 42, a CDR2 of SEQ ID NO: 44, and a CDR3 of SEQ ID NO: 46; or
(vi) the VH comprises a CDR1 of SEQ ID NO: 27, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46,
said method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

2. A method of producing an antibody-drug conjugate, said antibody-drug conjugate comprising (a) an antibody moiety that is an antibody or antigen-binding fragment thereof that specifically binds to human MERTK; (b) one or more drug moieties, each drug moiety being a cytotoxic agent; and (c) a linker; wherein the cytotoxic agent is conjugated to the antibody moiety via the linker;

wherein said antibody or antigen-binding fragment comprises a heavy chain variable region (VH) and a light chain variable region (VL), and wherein (i) the VH comprises a CDR 1 of SEQ ID NO: 1, a CDR2 of SEQ ID NO: 6, and a CDR3 of SEQ ID NO: 11; and the VL comprises a CDR1 of SEQ ID NO: 15, a CDR2 of SEQ ID NO: 19, and a CDR3 of SEQ ID NO: 22; or (ii) the VH comprises a CDR1 of SEQ ID NO: 2, a CDR2 of SEQ ID NO: 7, and a CDR3 of SEQ ID NO: 12; and the VL comprises a CDR1 of SEQ ID NO: 16, a CDR2 of SEQ ID NO: 20, and a CDR3 of SEQ ID NO: 23; or (iii) the VH comprises a CDR1 of SEQ ID NO: 3, a CDR2 of SEQ ID NO: 8, and a CDR3 of SEQ ID NO: 11; and the VL comprises a CDR1 of SEQ ID NO: 15, a CDR2 of SEQ ID NO: 19 and a CDR3 of SEQ ID NO: 22; or (iv) the VH comprises a CDR1 of SEQ ID NO: 4, a CDR2 of SEQ ID NO: 9, and a CDR3 of SEQ ID NO: 13; and the VL comprises a CDR1 of SEQ ID NO: 17, a CDR2 of SEQ ID NO: 21, and a CDR3 of SEQ ID NO: 24; or (v) the VH comprises a CDR1 of SEQ ID NO: 5, a CDR2 of SEQ ID NO: 10, and a CDR3 of SEQ ID NO: 14; and the VL comprises CDR1 of SEQ ID NO: 18, a CDR2 of SEQ ID NO: 20, and a CDR3 of SEQ ID NO: 22; or (vi) the VH comprises a CDR1 of SEQ ID NO: 3, a CDR2 of SEQ ID NO: 6, and a CDR3 of SEQ ID NO: 11; and the VL comprises a CDR1 of SEQ ID NO: 15, a CDR2 of SEQ ID NO: 19 and a CDR3 of SEQ ID NO: 22; or (vii) the VH comprises a CDR1 of SEQ ID NO: 25, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46; or (viii) the VH comprises a CDR1 of SEQ ID NO: 26, a CDR2 of SEQ ID NO: 31, and a CDR3 of SEQ ID NO: 36; and the VL comprises a CDR1 of SEQ ID NO: 40, a CDR2 of SEQ ID NO: 44, and a CDR3 of SEQ ID NO: 47; or (ix) the VH comprises a CDR1 of SEQ ID NO: 27, a CDR2 of SEQ ID NO: 32, and a CDR3 of SEQ ID NO: 35; and the VL comprises a CDR1 of SEQ ID NO: 39, a CDR2 of SEQ ID NO: 43, and a CDR3 of SEQ ID NO: 46; or (x) the VH comprises a CDR1 of SEQ ID NO: 28, a CDR2 of SEQ ID NO: 33, and a CDR3 of SEQ ID NO: 37; and the VL comprises a CDR1 of SEQ ID NO: 41, a CDR2 of SEQ ID NO: 45, and a CDR3 of SEQ ID NO: 48; or (xi) the VH comprises a CDR1 of SEQ ID NO: 29, a CDR2 of SEQ ID NO: 34, and a CDR3 of SEQ ID NO: 38; and the VL comprises a CDR1 of SEQ ID NO: 42, a CDR2 of SEQ ID NO: 44, and a CDR3 of SEQ ID NO: 46; or (xii) the VH comprises a CDR1 of SEQ ID NO: 27, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46, said method comprising the following steps in the order stated: (a) conjugating the linker directly to the antibody moiety to produce a linker-antibody moiety; (b) conjugating the linker of the linker-antibody moiety directly to the cytotoxic agent to produce the antibody-drug conjugate; and (c) purifying the antibody-drug conjugate.

3. A method of treating cancer in a subject in need thereof, comprising administering to said subject an antibody-drug conjugate and an additional therapeutic agent, wherein the antibody-drug conjugate comprises (a) an antibody moiety that is an antibody or antigen-binding fragment thereof that specifically binds to human MERTK; (b) one or more drug moieties, each drug moiety being a cytotoxic agent; and (c) optionally a linker; wherein the cytotoxic agent is conjugated to the antibody moiety via the linker; wherein said antibody or antigen-binding fragment comprises a heavy chain variable region (VH) and a light chain variable region (VL), wherein (i) the VH comprises a CDR 1 of SEQ ID NO: 1, a CDR2 of SEQ ID NO: 6, and a CDR3 of SEQ ID NO: 11; and the VL comprises a CDR1 of SEQ ID NO: 15, a CDR2 of SEQ ID NO: 19, and a CDR3 of SEQ ID NO: 22; or (ii) the VH comprises a CDR1 of SEQ ID NO: 2, a CDR2 of SEQ ID NO: 7, and a CDR3 of SEQ ID NO: 12; and the VL comprises a CDR1 of SEQ ID NO: 16, a CDR2 of SEQ ID NO: 20, and a CDR3 of SEQ ID NO: 23; or (iii) the VH comprises a CDR1 of SEQ ID NO: 3, a CDR2 of SEQ ID NO: 8, and a CDR3 of SEQ ID NO: 11; and the VL comprises a CDR1 of SEQ ID NO: 15, a CDR2 of SEQ ID NO: 19 and a CDR3 of SEQ ID NO: 22; or (iv) the VH comprises a CDR1 of SEQ ID NO: 4, a CDR2 of SEQ ID NO: 9, and a CDR3 of SEQ ID NO: 13; and the VL comprises a CDR1 of SEQ ID NO: 17, a CDR2 of SEQ ID NO: 21, and a CDR3 of SEQ ID NO: 24; or (v) the VH comprises a CDR1 of SEQ ID NO: 5, a CDR2 of SEQ ID NO: 10, and a CDR3 of SEQ ID NO: 14; and the VL comprises CDR1 of SEQ ID NO: 18, a CDR2 of SEQ ID NO: 20, and a CDR3 of SEQ ID NO: 22; or (vi) the VH comprises a CDR1 of SEQ ID NO: 3, a CDR2 of SEQ ID NO: 6, and a CDR3 of SEQ ID NO: 11; and the VL comprises a CDR1 of SEQ ID NO: 15, a CDR2 of SEQ ID NO: 19 and a CDR3 of SEQ ID NO: 22; or (vii) the VH comprises a CDR1 of SEQ ID NO: 25, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46; or (viii) the VH comprises a CDR1 of SEQ ID NO: 26, a CDR2 of SEQ ID NO: 31, and a CDR3 of SEQ ID NO: 36; and the VL comprises a CDR1 of SEQ ID NO: 40, a CDR2 of SEQ ID NO: 44, and a CDR3 of SEQ ID NO: 47; or (ix) the VH comprises a CDR1 of SEQ ID NO: 27, a CDR2 of SEQ ID NO: 32, and a CDR3 of SEQ ID NO: 35; and the VL comprises a CDR1 of SEQ ID NO: 39, a CDR2 of SEQ ID NO: 43, and a CDR3 of SEQ ID NO: 46; or (x) the VH comprises a CDR1 of SEQ ID NO: 28, a CDR2 of SEQ ID NO: 33, and a CDR3 of SEQ ID NO:

37; and the VL comprises a CDR1 of SEQ ID NO: 41, a CDR2 of SEQ ID NO: 45, and a CDR3 of SEQ ID NO: 48; or (xi) the VH comprises a CDR1 of SEQ ID NO: 29, a CDR2 of SEQ ID NO: 34, and a CDR3 of SEQ ID NO: 38; and the VL comprises a CDR1 of SEQ ID NO: 42, a CDR2 of SEQ ID NO: 44, and a CDR3 of SEQ ID NO: 46; or (xii) the VH comprises a CDR1 of SEQ ID NO: 27, a CDR2 of SEQ ID NO: 30, and a CDR3 of SEQ ID NO: 35; and the VL comprises a CDR1 of SEQ ID NO: 39, a CDR2 of SEQ ID NO: 43, and a CDR3 of SEQ ID NO: 46.

4. The method of claim 3, wherein said cancer is a cancer of the lung, breast, bone, ovary, stomach, pancreas, larynx, esophagus, testes, liver, parotid, biliary tract, colon, rectum, cervix, uterus, endometrium, kidney, bladder, prostate or thyroid.

5. The method of claim 3, wherein said cancer is a sarcoma, squamous cell carcinoma, melanoma, glioma, glioblastoma, neuroblastoma or Kaposi's sarcomas.

6. The method of claim 4, wherein said cancer is breast cancer.

7. The method of claim 6, wherein said cancer is triple-negative breast cancer.

8. The method of claim 3, wherein the additional therapeutic agent is for treating the cancer.

9. The method of claim 8, wherein the additional therapeutic agent is an immunotherapy or an angiogenesis inhibitor.

10. The method of claim 6, wherein the additional therapeutic agent is an agent used to treat breast cancer that is selected from the group consisting of Tamoxifen, Raloxifene, Paclitaxel, Cyclophosphamide, Docetaxel, Vinblastine, Fluorouracil, Everolimus, Trastuzumab, Trastuzumab-Emtansine, Pertuzumab, and Lapatinib Ditosylate.

11. The method of claim 8, wherein said cancer is melanoma, and wherein the additional therapeutic agent is an agent used to treat melanoma that is selected from the group consisting of a BRAF inhibitor, a MEK inhibitor, and Dacarbazine.

12. The method of claim 9, wherein the additional therapeutic agent is an immunotherapy that is an antibody that is a CTLA-4 inhibitor, a PD-1 inhibitor, or a PD-L1 inhibitor.

13. The method of claim 9, wherein the additional therapeutic agent is an angiogenesis inhibitor that is selected from the group consisting of a VEGF inhibitor, a VEGFR2 inhibitor, Sunitinib, and Sorafenib.

14. The method of claim 3, wherein said subject is a human.

15. The method of claim 1, wherein the VH comprises the sequence of SEQ ID NO: 51, and the VL comprises the sequence of SEQ ID NO: 52.

16. The method of claim 2, wherein (A) the VH comprises the sequence of SEQ ID NO: 51, and the VL comprises the sequence of SEQ ID NO: 52; or (B) the VH comprises the sequence of SEQ ID NO: 49, and the VL comprises the sequence of SEQ ID NO: 50.

17. The method of claim 3, wherein (A) the VH comprises the sequence of SEQ ID NO: 51, and the VL comprises the sequence of SEQ ID NO: 52; or (B) the VH comprises the sequence of SEQ ID NO: 49, and the VL comprises the sequence of SEQ ID NO: 50.

18. The method of claim 3, wherein the antibody moiety is an immunoglobulin.

19. The method of claim 3, wherein the antibody moiety is humanized.

20. The method of claim 3, wherein the antibody-drug conjugate has a molar ratio of the antibody moiety to the drug moiety that is between 1:1 and 1:12.

21. The method of claim 3, wherein the cytotoxic agent is an auristatin, a maytansinoid, a pyrrolobenzodiazepine, an indolinobenzodiazepine, a calicheamicin, a camptothecin analogue, a duocarmycin, a tubulin inhibitor, tubulysin, a tubulysin analogue, amberstatin269, doxorubicin, an antibiotic, an anthracycline, a microtubule inhibitor, a spliceostatin, or a thailanstatin.

22. The method of claim 3, wherein the cytotoxic agent is monomethyl auristatin E (MMAE) or monomethyl auristatin F (MMAF).

23. The method of claim 22, wherein the cytotoxic agent in MMAE.

24. The method of claim 3, wherein the cytotoxic agent is SN38.

25. The method of claim 5, wherein said cancer is a melanoma.

26. A method of producing an antibody-drug conjugate, said antibody-drug conjugate comprising (a) an antibody moiety that is an antibody or antigen-binding fragment thereof that specifically binds to human MERTK; and (b) one or more drug moieties, each drug moiety being a cytotoxic agent; and (c) a linker; wherein the cytotoxic agent is conjugated to the antibody moiety via the linker;

wherein said antibody or antigen-binding fragment comprises a heavy chain variable region (VH) and a light chain variable region (VL), and wherein (i) the VH comprises a CDR 1 of SEQ ID NO: 1, a CDR2 of SEQ ID NO: 6, and a CDR3 of SEQ ID NO: 11; and the VL comprises a CDR1 of SEQ ID NO: 15, a CDR2 of SEQ ID NO: 19, and a CDR3 of SEQ ID NO: 22; or (ii) the VH comprises a CDR1 of SEQ ID NO: 2, a CDR2 of SEQ ID NO: 7, and a CDR3 of SEQ ID NO: 12; and the VL comprises a CDR1 of SEQ ID NO: 16, a CDR2 of SEQ ID NO: 20, and a CDR3 of SEQ ID NO: 23; or (iii) the VH comprises a CDR1 of SEQ ID NO: 3, a CDR2 of SEQ ID NO: 8, and a CDR3 of SEQ ID NO: 11; and the VL comprises a CDR1 of SEQ ID NO: 15, a CDR2 of SEQ ID NO: 19 and a CDR3 of SEQ ID NO: 22; or (iv) the VH comprises a CDR1 of SEQ ID NO: 4, a CDR2 of SEQ ID NO: 9, and a CDR3 of SEQ ID NO: 13; and the VL comprises a CDR1 of SEQ ID NO: 17, a CDR2 of SEQ ID NO: 21, and a CDR3 of SEQ ID NO: 24; or (v) the VH comprises a CDR1 of SEQ ID NO: 5, a CDR2 of SEQ ID NO: 10, and a CDR3 of SEQ ID NO: 14; and the VL comprises CDR1 of SEQ ID NO: 18, a CDR2 of SEQ ID NO: 20, and a CDR3 of SEQ ID NO: 22; or (vi) the VH comprises a CDR1 of SEQ ID NO: 3, a CDR2 of SEQ ID NO: 6, and a CDR3 of SEQ ID NO: 11; and the VL comprises a CDR1 of SEQ ID NO: 15, a CDR2 of SEQ ID NO: 19 and a CDR3 of SEQ ID NO: 22, said method comprising the following steps in the order stated: (a) conjugating the linker directly to the cytotoxic agent to produce a linker-cytotoxic agent moiety; (b) conjugating the linker of the linker-cytotoxic agent moiety directly to the antibody moiety to produce the antibody-drug conjugate; and (c) purifying the antibody-drug conjugate.

27. The method of claim 2, wherein
(i) the VH comprises a CDR 1 of SEQ ID NO: 1, a CDR2 of SEQ ID NO: 6, and a CDR3 of SEQ ID NO: 11; and the VL comprises a CDR1 of SEQ ID NO: 15, a CDR2 of SEQ ID NO: 19, and a CDR3 of SEQ ID NO: 22; or
(ii) the VH comprises a CDR1 of SEQ ID NO: 2, a CDR2 of SEQ ID NO: 7, and a CDR3 of SEQ ID NO: 12; and the VL comprises a CDR1 of SEQ ID NO: 16, a CDR2 of SEQ ID NO: 20, and a CDR3 of SEQ ID NO: 23; or
(iii) the VH comprises a CDR1 of SEQ ID NO: 3, a CDR2 of SEQ ID NO: 8, and a CDR3 of SEQ ID NO: 11; and the VL comprises a CDR1 of SEQ ID NO: 15, a CDR2 of SEQ ID NO: 19 and a CDR3 of SEQ ID NO: 22; or
(iv) the VH comprises a CDR1 of SEQ ID NO: 4, a CDR2 of SEQ ID NO: 9, and a CDR3 of SEQ ID NO: 13; and the VL comprises a CDR1 of SEQ ID NO: 17, a CDR2 of SEQ ID NO: 21, and a CDR3 of SEQ ID NO: 24; or
(v) the VH comprises a CDR1 of SEQ ID NO: 5, a CDR2 of SEQ ID NO: 10, and a CDR3 of SEQ ID NO: 14; and the VL comprises CDR1 of SEQ ID NO: 18, a CDR2 of SEQ ID NO: 20, and a CDR3 of SEQ ID NO: 22; or
(vi) the VH comprises a CDR1 of SEQ ID NO: 3, a CDR2 of SEQ ID NO: 6, and a CDR3 of SEQ ID NO: 11; and the VL comprises a CDR1 of SEQ ID NO: 15, a CDR2 of SEQ ID NO: 19 and a CDR3 of SEQ ID NO: 22.

28. The method of claim 3, wherein
(i) the VH comprises a CDR 1 of SEQ ID NO: 1, a CDR2 of SEQ ID NO: 6, and a CDR3 of SEQ ID NO: 11; and the VL comprises a CDR1 of SEQ ID NO: 15, a CDR2 of SEQ ID NO: 19, and a CDR3 of SEQ ID NO: 22; or
(ii) the VH comprises a CDR1 of SEQ ID NO: 2, a CDR2 of SEQ ID NO: 7, and a CDR3 of SEQ ID NO: 12; and the VL comprises a CDR1 of SEQ ID NO: 16, a CDR2 of SEQ ID NO: 20, and a CDR3 of SEQ ID NO: 23; or
(iii) the VH comprises a CDR1 of SEQ ID NO: 3, a CDR2 of SEQ ID NO: 8, and a CDR3 of SEQ ID NO: 11; and the VL comprises a CDR1 of SEQ ID NO: 15, a CDR2 of SEQ ID NO: 19 and a CDR3 of SEQ ID NO: 22; or
(iv) the VH comprises a CDR1 of SEQ ID NO: 4, a CDR2 of SEQ ID NO: 9, and a CDR3 of SEQ ID NO: 13; and the VL comprises a CDR1 of SEQ ID NO: 17, a CDR2 of SEQ ID NO: 21, and a CDR3 of SEQ ID NO: 24; or
(v) the VH comprises a CDR1 of SEQ ID NO: 5, a CDR2 of SEQ ID NO: 10, and a CDR3 of SEQ ID NO: 14; and the VL comprises CDR1 of SEQ ID NO: 18, a CDR2 of SEQ ID NO: 20, and a CDR3 of SEQ ID NO: 22; or
(vi) the VH comprises a CDR1 of SEQ ID NO: 3, a CDR2 of SEQ ID NO: 6, and a CDR3 of SEQ ID NO: 11; and the VL comprises a CDR1 of SEQ ID NO: 15, a CDR2 of SEQ ID NO: 19 and a CDR3 of SEQ ID NO: 22.

29. The method of claim 26, wherein the VH comprises the sequence of SEQ ID NO: 49, and the VL comprises the sequence of SEQ ID NO: 50.

* * * * *

SEQUENCE LISTING

```
Sequence total quantity: 58
SEQ ID NO: 1            moltype = AA  length = 5
FEATURE                 Location/Qualifiers
REGION                  1..5
                        note = Antibody M6 VH CDR1 according to Kabat
source                  1..5
                        mol_type = protein
                        organism = synthetic construct
SEQUENCE: 1
NYGMN                                                                   5
```

```
SEQ ID NO: 2              moltype = AA  length = 7
FEATURE                   Location/Qualifiers
REGION                    1..7
                          note = Antibody M6 VH CDR1 according to Chothia
source                    1..7
                          mol_type = protein
                          organism = synthetic construct
SEQUENCE: 2
GYTFTNY                                                                    7

SEQ ID NO: 3              moltype = AA  length = 10
FEATURE                   Location/Qualifiers
REGION                    1..10
                          note = Antibody M6 VH CDR1 according to AbM
source                    1..10
                          mol_type = protein
                          organism = synthetic construct
SEQUENCE: 3
GYTFTNYGMN                                                                10

SEQ ID NO: 4              moltype = AA  length = 6
FEATURE                   Location/Qualifiers
REGION                    1..6
                          note = Antibody M6 VH CDR1 according to Contact
source                    1..6
                          mol_type = protein
                          organism = synthetic construct
SEQUENCE: 4
TNYGMN                                                                     6

SEQ ID NO: 5              moltype = AA  length = 8
FEATURE                   Location/Qualifiers
REGION                    1..8
                          note = Antibody M6 VH CDR1 according to IMGT
source                    1..8
                          mol_type = protein
                          organism = synthetic construct
SEQUENCE: 5
GYTFTNYG                                                                   8

SEQ ID NO: 6              moltype = AA  length = 17
FEATURE                   Location/Qualifiers
REGION                    1..17
                          note = Antibody M6 VH CDR2 according to Kabat
source                    1..17
                          mol_type = protein
                          organism = synthetic construct
SEQUENCE: 6
WINTYTGEPT YADDFKG                                                        17

SEQ ID NO: 7              moltype = AA  length = 4
FEATURE                   Location/Qualifiers
REGION                    1..4
                          note = Antibody M6 VH CDR2 according to Chothia
source                    1..4
                          mol_type = protein
                          organism = synthetic construct
SEQUENCE: 7
TYTG                                                                       4

SEQ ID NO: 8              moltype = AA  length = 10
FEATURE                   Location/Qualifiers
REGION                    1..10
                          note = Antibody M6 VH CDR2 according to AbM
source                    1..10
                          mol_type = protein
                          organism = synthetic construct
SEQUENCE: 8
WINTYTGEPT                                                                10

SEQ ID NO: 9              moltype = AA  length = 13
FEATURE                   Location/Qualifiers
REGION                    1..13
                          note = Antibody M6 VH CDR2 according to Contact
source                    1..13
                          mol_type = protein
                          organism = synthetic construct
SEQUENCE: 9
WMGWINTYTG EPT                                                            13
```

```
SEQ ID NO: 10              moltype = AA   length = 8
FEATURE                    Location/Qualifiers
REGION                     1..8
                           note = Antibody M6 VH CDR2 according to IMGT
source                     1..8
                           mol_type = protein
                           organism = synthetic construct
SEQUENCE: 10
INTYTGEP                                                               8

SEQ ID NO: 11              moltype = AA   length = 11
FEATURE                    Location/Qualifiers
REGION                     1..11
                           note = Antibody M6 VH CDR3 according to Kabat
source                     1..11
                           mol_type = protein
                           organism = synthetic construct
SEQUENCE: 11
KSTVVSRYFD V                                                          11

SEQ ID NO: 12              moltype = AA   length = 9
FEATURE                    Location/Qualifiers
REGION                     1..9
                           note = Antibody M6 VH CDR3 according to Chothia
source                     1..9
                           mol_type = protein
                           organism = synthetic construct
SEQUENCE: 12
STVVSRYFD                                                              9

SEQ ID NO: 13              moltype = AA   length = 12
FEATURE                    Location/Qualifiers
REGION                     1..12
                           note = Antibody M6 VH CDR3 according to Contact
source                     1..12
                           mol_type = protein
                           organism = synthetic construct
SEQUENCE: 13
ARKSTVVSRY FD                                                         12

SEQ ID NO: 14              moltype = AA   length = 13
FEATURE                    Location/Qualifiers
REGION                     1..13
                           note = Antibody M6 VH CDR3 according to IMGT
source                     1..13
                           mol_type = protein
                           organism = synthetic construct
SEQUENCE: 14
ARKSTVVSRY FDV                                                        13

SEQ ID NO: 15              moltype = AA   length = 11
FEATURE                    Location/Qualifiers
REGION                     1..11
                           note = Antibody M6 VL CDR1 according to Kabat
source                     1..11
                           mol_type = protein
                           organism = synthetic construct
SEQUENCE: 15
KASQDVGDAV T                                                          11

SEQ ID NO: 16              moltype = AA   length = 7
FEATURE                    Location/Qualifiers
REGION                     1..7
                           note = Antibody M6 VL CDR1 according to Chothia
source                     1..7
                           mol_type = protein
                           organism = synthetic construct
SEQUENCE: 16
SQDVGDA                                                                7

SEQ ID NO: 17              moltype = AA   length = 7
FEATURE                    Location/Qualifiers
REGION                     1..7
                           note = Antibody M6 VL CDR1 according to Contact
source                     1..7
                           mol_type = protein
                           organism = synthetic construct
SEQUENCE: 17
```

```
GDAVTWC                                                                            7

SEQ ID NO: 18          moltype = AA  length = 6
FEATURE                Location/Qualifiers
REGION                 1..6
                       note = Antibody M6 VL CDR1 according to IMPT
source                 1..6
                       mol_type = protein
                       organism = synthetic construct
SEQUENCE: 18
QDVGDA                                                                             6

SEQ ID NO: 19          moltype = AA  length = 7
FEATURE                Location/Qualifiers
REGION                 1..7
                       note = Antibody M6 VL CDR2 according to Kabat
source                 1..7
                       mol_type = protein
                       organism = synthetic construct
SEQUENCE: 19
WASTRHT                                                                            7

SEQ ID NO: 20          moltype =     length =
SEQUENCE: 20
000

SEQ ID NO: 21          moltype = AA  length = 10
FEATURE                Location/Qualifiers
REGION                 1..10
                       note = Antibody M6 VL CDR2 according to Contact
source                 1..10
                       mol_type = protein
                       organism = synthetic construct
SEQUENCE: 21
LLIYWASTRH                                                                         10

SEQ ID NO: 22          moltype = AA  length = 9
FEATURE                Location/Qualifiers
REGION                 1..9
                       note = Antibody M6 VL CDR3 according to Kabat
source                 1..9
                       mol_type = protein
                       organism = synthetic construct
SEQUENCE: 22
QQYRSYPLT                                                                          9

SEQ ID NO: 23          moltype = AA  length = 6
FEATURE                Location/Qualifiers
REGION                 1..6
                       note = Antibody M6 VL CDR3 according to Chothia
source                 1..6
                       mol_type = protein
                       organism = synthetic construct
SEQUENCE: 23
YRSYPL                                                                             6

SEQ ID NO: 24          moltype = AA  length = 8
FEATURE                Location/Qualifiers
REGION                 1..8
                       note = Antibody M6 VL CDR3 according to Contact
source                 1..8
                       mol_type = protein
                       organism = synthetic construct
SEQUENCE: 24
QQYRSYPL                                                                           8

SEQ ID NO: 25          moltype = AA  length = 5
FEATURE                Location/Qualifiers
REGION                 1..5
                       note = Antibody M19 VH CDR1 according to Kabat
source                 1..5
                       mol_type = protein
                       organism = synthetic construct
SEQUENCE: 25
DYSMH                                                                              5

SEQ ID NO: 26          moltype = AA  length = 7
FEATURE                Location/Qualifiers
REGION                 1..7
```

```
                        note = Antibody M19 VH CDR1 according to Chothia
source                  1..7
                        mol_type = protein
                        organism = synthetic construct
SEQUENCE: 26
NYTFTDY                                                                 7

SEQ ID NO: 27           moltype = AA  length = 10
FEATURE                 Location/Qualifiers
REGION                  1..10
                        note = Antibody M19 VH CDR1 according to AbM
source                  1..10
                        mol_type = protein
                        organism = synthetic construct
SEQUENCE: 27
NYTFTDYSMH                                                             10

SEQ ID NO: 28           moltype = AA  length = 6
FEATURE                 Location/Qualifiers
REGION                  1..6
                        note = Antibody M19 VH CDR1 according to Contact
source                  1..6
                        mol_type = protein
                        organism = synthetic construct
SEQUENCE: 28
TDYSMH                                                                  6

SEQ ID NO: 29           moltype = AA  length = 8
FEATURE                 Location/Qualifiers
REGION                  1..8
                        note = Antibody M19 VH CDR1 according to IMGT
source                  1..8
                        mol_type = protein
                        organism = synthetic construct
SEQUENCE: 29
NYTFTDYS                                                                8

SEQ ID NO: 30           moltype = AA  length = 17
FEATURE                 Location/Qualifiers
REGION                  1..17
                        note = Antibody M19 VH CDR2 according to Kabat
source                  1..17
                        mol_type = protein
                        organism = synthetic construct
SEQUENCE: 30
WINTDTGEPT YADDFKG                                                     17

SEQ ID NO: 31           moltype = AA  length = 4
FEATURE                 Location/Qualifiers
REGION                  1..4
                        note = Antibody M19 VH CDR2 according to Chothia
source                  1..4
                        mol_type = protein
                        organism = synthetic construct
SEQUENCE: 31
TDTG                                                                    4

SEQ ID NO: 32           moltype = AA  length = 10
FEATURE                 Location/Qualifiers
REGION                  1..10
                        note = Antibody M19 VH CDR2 according to AbM
source                  1..10
                        mol_type = protein
                        organism = synthetic construct
SEQUENCE: 32
WINTDTGEPT                                                             10

SEQ ID NO: 33           moltype = AA  length = 13
FEATURE                 Location/Qualifiers
REGION                  1..13
                        note = Antibody M19 VH CDR2 according to Contact
source                  1..13
                        mol_type = protein
                        organism = synthetic construct
SEQUENCE: 33
WVGWINTDTG EPT                                                         13

SEQ ID NO: 34           moltype = AA  length = 8
FEATURE                 Location/Qualifiers
```

```
                        REGION              1..8
                                            note = Antibody M19 VH CDR2 according to IMGT
                        source              1..8
                                            mol_type = protein
                                            organism = synthetic construct
SEQUENCE: 34
INTDTGEP                                                                              8

SEQ ID NO: 35           moltype = AA   length = 7
FEATURE                 Location/Qualifiers
REGION                  1..7
                        note = Antibody M19 VH CDR3 according to Kabat
source                  1..7
                        mol_type = protein
                        organism = synthetic construct
SEQUENCE: 35
WFGAMDY                                                                               7

SEQ ID NO: 36           moltype = AA   length = 5
FEATURE                 Location/Qualifiers
REGION                  1..5
                        note = Antibody M19 VH CDR3 according to Chothia
source                  1..5
                        mol_type = protein
                        organism = synthetic construct
SEQUENCE: 36
FGAMD                                                                                 5

SEQ ID NO: 37           moltype = AA   length = 8
FEATURE                 Location/Qualifiers
REGION                  1..8
                        note = Antibody M19 VH CDR3 according to Contact
source                  1..8
                        mol_type = protein
                        organism = synthetic construct
SEQUENCE: 37
ARWFGAMD                                                                              8

SEQ ID NO: 38           moltype = AA   length = 9
FEATURE                 Location/Qualifiers
REGION                  1..9
                        note = Antibody M19 VH CDR3 according to IMGT
source                  1..9
                        mol_type = protein
                        organism = synthetic construct
SEQUENCE: 38
ARWFGAMDY                                                                             9

SEQ ID NO: 39           moltype = AA   length = 11
FEATURE                 Location/Qualifiers
REGION                  1..11
                        note = Antibody M19 VL CDR1 according to Kabat
source                  1..11
                        mol_type = protein
                        organism = synthetic construct
SEQUENCE: 39
KASQDVTNVV A                                                                         11

SEQ ID NO: 40           moltype = AA   length = 7
FEATURE                 Location/Qualifiers
REGION                  1..7
                        note = Antibody M19 VL CDR1 according to Chothia
source                  1..7
                        mol_type = protein
                        organism = synthetic construct
SEQUENCE: 40
SQDVTNV                                                                               7

SEQ ID NO: 41           moltype = AA   length = 7
FEATURE                 Location/Qualifiers
REGION                  1..7
                        note = Antibody M19 VL CDR1 according to Contact
source                  1..7
                        mol_type = protein
                        organism = synthetic construct
SEQUENCE: 41
TNVVAWY                                                                               7

SEQ ID NO: 42           moltype = AA   length = 6
```

```
FEATURE                  Location/Qualifiers
REGION                   1..6
                         note = Antibody M19 VL CDR1 according to IMGT
source                   1..6
                         mol_type = protein
                         organism = synthetic construct
SEQUENCE: 42
QDVTNV                                                                        6

SEQ ID NO: 43            moltype = AA  length = 7
FEATURE                  Location/Qualifiers
REGION                   1..7
                         note = Antibody M19 VL CDR2 according to Kabat
source                   1..7
                         mol_type = protein
                         organism = synthetic construct
SEQUENCE: 43
SASYRYT                                                                       7

SEQ ID NO: 44            moltype =   length =
SEQUENCE: 44
000

SEQ ID NO: 45            moltype = AA  length = 10
FEATURE                  Location/Qualifiers
REGION                   1..10
                         note = Antibody M19 VL CDR2 according to Contact
source                   1..10
                         mol_type = protein
                         organism = synthetic construct
SEQUENCE: 45
LLIYSASYRY                                                                   10

SEQ ID NO: 46            moltype = AA  length = 9
FEATURE                  Location/Qualifiers
REGION                   1..9
                         note = Antibody M19 VL CDR3 according to Kabat
source                   1..9
                         mol_type = protein
                         organism = synthetic construct
SEQUENCE: 46
QQYYRTPRT                                                                     9

SEQ ID NO: 47            moltype = AA  length = 6
FEATURE                  Location/Qualifiers
REGION                   1..6
                         note = Antibody M19 VL CDR3 according to Chothia
source                   1..6
                         mol_type = protein
                         organism = synthetic construct
SEQUENCE: 47
YYRTPR                                                                        6

SEQ ID NO: 48            moltype = AA  length = 8
FEATURE                  Location/Qualifiers
REGION                   1..8
                         note = Antibody M19 VL CDR3 according to Contact
source                   1..8
                         mol_type = protein
                         organism = synthetic construct
SEQUENCE: 48
QQYYRTPR                                                                      8

SEQ ID NO: 49            moltype = AA  length = 120
FEATURE                  Location/Qualifiers
REGION                   1..120
                         note = Antibody M6 VH Variable Region
source                   1..120
                         mol_type = protein
                         organism = synthetic construct
SEQUENCE: 49
QVKLEESGPE LKKPGETVKI SCKASGYTFT NYGMNWVKQA PGKGLKWMGW INTYTGEPTY             60
ADDFKGRFVF SLETSASTAY LQINNLKNED MATYFCARKS TVVSRYFDVW GAGTTVTVSS            120

SEQ ID NO: 50            moltype = AA  length = 108
FEATURE                  Location/Qualifiers
REGION                   1..108
                         note = Antibody M6 VL Variable Region
source                   1..108
```

```
                        mol_type = protein
                        organism = synthetic construct
SEQUENCE: 50
DIVLTQTHKF MSTSVGDRVS ITCKASQDVG DAVTWCQQKP GQPPKLLIYW ASTRHTGVPD    60
RFTGSGSGTD FTLTINNVQS EDLADYFCQQ YRSYPLTFGA GTKLELKR                108

SEQ ID NO: 51           moltype = AA   length = 116
FEATURE                 Location/Qualifiers
REGION                  1..116
                        note = Antibody M19 VH Variable Region
source                  1..116
                        mol_type = protein
                        organism = synthetic construct
SEQUENCE: 51
EVQLEESGPD LKKPGETVKI SCKASNYTFT DYSMHWVKQA PGKGLKWVGW INTDTGEPTY    60
ADDFKGRFAF SLETSASTAY LQINNLKNED TATYFCARWF GAMDYWGQGT SVTVSS       116

SEQ ID NO: 52           moltype = AA   length = 108
FEATURE                 Location/Qualifiers
REGION                  1..108
                        note = Antibody M19 VL Variable Region
source                  1..108
                        mol_type = protein
                        organism = synthetic construct
SEQUENCE: 52
DIVITQSHKF MSTSVGDRVS ITCKASQDVT NVVAWYQQKP GQSPKLLIYS ASYRYTGVPD    60
RFTGSGSGTD FTFTISSVQA EDLAVYYCQQ YYRTPRTFGG GTKLEIKR                108

SEQ ID NO: 53           moltype = DNA   length = 360
FEATURE                 Location/Qualifiers
misc_feature            1..360
                        note = Antibody M6 VH Variable Region
source                  1..360
                        mol_type = other DNA
                        organism = synthetic construct
SEQUENCE: 53
caggttaagc tggaggagtc tggacctgag ctgaagaagc tggagagac agtcaagatc     60
tcctgcaagg cttctggata taccttcaca aactatggaa tgaactgggt gaagcaggct   120
ccaggaaagg gtttaaagtg gatgggctgg ataaacacct acactggaga gccaacatat   180
gctgatgact tcaagggacg gtttgtcttc tctttggaaa cctctgccag cactgcctac   240
ttgcagatca acaacctcaa aaatgaggac atggccacat atttctgtgc aagaaaaagt   300
acggtagtaa gtaggtactt cgatgtctgg ggcgcaggga ccacggtcac cgtctcctca   360

SEQ ID NO: 54           moltype = DNA   length = 320
FEATURE                 Location/Qualifiers
misc_feature            1..320
                        note = Antibody M6 VL Variable Region
source                  1..320
                        mol_type = other DNA
                        organism = synthetic construct
SEQUENCE: 54
gggatattgt gctgacacag actcacaaat tcatgtccac atcagtagga gacagggtca    60
gcatcacctg caaggccagt caggatgtgg gtgatgctgt aacctggtgt caacagaaac   120
caggtcaacc tcctaaacta ctgatttact gggcatccac ccggcacact ggagtccctg   180
atcgcttcac aggcagtggg tctgggacag atttcactct caccattaac aatgtgcagt   240
ctgaagactt ggcagattat ttctgtcagc aatatcgcag ctatcctctc acgttcggtg   300
ctgggaccaa gctggagctg                                               320

SEQ ID NO: 55           moltype = DNA   length = 378
FEATURE                 Location/Qualifiers
misc_feature            1..378
                        note = Antibody M19 VH Variable Region
source                  1..378
                        mol_type = other DNA
                        organism = synthetic construct
SEQUENCE: 55
gaggtccagc tggaggagtc tggacctgac ctgaagaagc tggagagac agtcaagatc     60
tcctgcaagg cttctaatta taccttcaca gactattgca tgcactgggt gaagcaggct   120
ccaggaaagg gtttaaagtg ggtgggctgg ataaacactg acactggtga gccaacatat   180
gcagatgact tcaagggacg ctttgccttc tctttggaaa cctctgccag cactgcctat   240
ttacagatca acaacctcaa aaatgaggac acggctacat atttctgtgc tagatggttt   300
ggtgctatgg actactgggg tcaaggaacc tcagtcaccg tctcctcagc caaaacgaca   360
ccccccatctg tctattcc                                                378

SEQ ID NO: 56           moltype = DNA   length = 326
FEATURE                 Location/Qualifiers
misc_feature            1..326
                        note = Antibody M19 VL Variable Region
source                  1..326
```

```
                        mol_type = other DNA
                        organism = synthetic construct
SEQUENCE: 56
gggatattgt gatcacacag tctcacaaat tcatgtccac atcagtagga gacagggtca    60
gcatcacctg caaggccagt caggatgtga ctaatgttgt agcctggtat caacagaaac   120
caggacaatc tcctaaacta ctgatttatt cggcatccta ccggtacact ggagtccctg   180
atcgcttcac tggcagtgga tctgggacgg atttcacttt caccatcagc agtgtgcagg   240
ctgaagacct ggcagtttat tactgtcagc aatattatcg tactcctcgg acgttcggtg   300
gaggcaccaa gctggaaatc aaacgg                                         326

SEQ ID NO: 57           moltype = AA  length = 999
FEATURE                 Location/Qualifiers
REGION                  1..999
                        note = Full-Length Human MERTK (Swuss-Prot ID Q12866.2)
source                  1..999
                        mol_type = protein
                        organism = Homo sapiens
SEQUENCE: 57
MGPAPLPLLL GLFLPALWRR AITEAREEAK PYPLFPGPFP GSLQTDHTPL LSLPHASGYQ    60
PALMFSPTQP GRPHTGNVAI PQVTSVESKP LPPLAFKHTV GHIILSEHKG VKFNCSISVP   120
NIYQDTTISW WKDGKELLGA HHAITQFYPD DEVTAIIASF SITSVQRSDN GSYICKMKIN   180
NEEIVSDPIY IEVQGLPHFT KQPESMNVTR NTAFNLTCQA VGPPEPVNIF WVQNSSRVNE   240
QPEKSPSVLT VPGLTEMAVF SCEAHNDKGL TVSKGVQINI KAIPSPPTEV SIRNSTAHSI   300
LISWVPGFDG YSPFRNCSIQ VKEADPLSNG SVMIFNTSAL PHLYQIKQLQ ALANYSIGVS   360
CMNEIGWSAV SPWILASTTE GAPSVAPLNV TVFLNESSDN VDIRWMKPPT KQQDGELVGY   420
RISHVWQSAG ISKELLEEVG QNGSRARISV QVHNATCTVR IAAVTRGGVG PFSDPVKIFI   480
PAHGWVDYAP SSTPAPGNAD PVLIIFGCFC GFILIGLILY ISLAIRKRVQ ETKFGNAFTE   540
EDSELVVNYI AKKSFCRRAI ELTLHSLGVS EELQNKLEDV VIDRNLLILG KILGEGEFGS   600
VMEGNLKQED GTSLKVAVKT MKLDNSSQRE IEEFLSEAAC MKDFSHPNVI RLLGVCIEMS   660
SQGIPKPMVI LPFMKYGDLH TYLLYSRLET GPKHIPLQTL LKFMVDIALG MEYLSNRNFL   720
HRDLAARNCM LRDDMTVCVA DFGLSKKIYS GDYYRQGRIA KMPVKWIAIE SLADRVYTSK   780
SDVWAFGVTM WEIATRGMTP YPGVQNHEMY DYLLHGHRLK QPEDCLDELY EIMYSCWRTD   840
PLDRPTFSVL RLQLEKLLES LPDVRNQADV IYVNTQLLES SEGLAQGSTL APLDLNIDPD   900
SIIASCTPRA AISVVTAEVH DSKPHEGRYI LNGGSEEWED LTSAPSAAVT AEKNSVLPGE   960
RLVRNGVSWS HSSMLPLGSS LPDELLFADD SSEGSEVLM                          999

SEQ ID NO: 58           moltype = AA  length = 474
FEATURE                 Location/Qualifiers
REGION                  1..474
                        note = Extracellular Doman of MERTK Used for Immunization
source                  1..474
                        mol_type = protein
                        organism = Homo sapiens
SEQUENCE: 58
REEAKPYPLF PGPFPGSLQT DHTPLLSLPH ASGYQPALMF SPTQPGRPHT GNVAIPQVTS    60
VESKPLPPLA FKHTVGHIIL SEHKGVKFNC SISVPNIYQD TTISWWKDGK ELLGAHHAIT   120
QFYPDDEVTA IIASFSITSV QRSDNGSYIC KMKINNEEIV SDPIYIEVQG LPHFTKQPES   180
MNVTRNTAFN LTCQAVGPPE PVNIFWVQNS SRVNEQPEKS PSVLTVPGLT EMAVFSCEAH   240
NDKGLTVSKG VQINIKAIPS PPTEVSIRNS TAHSILISWV PGFDGYSPFR NCSIQVKEAD   300
PLSNGSVMIF NTSALPHLYQ IKQLQALANY SIGVSCMNEI GWSAVSPWIL ASTTEGAPSV   360
APLNVTVFLN ESSDNVDIRW MKPPTKQQDG ELVGYRISHV WQSAGISKEL LEEVGQNGSR   420
ARISVQVHNA TCTVRIAAVT RGGVGPFSDP VKIFIPAHGW VDYAPSSTPA PGNA          474
```